United States Patent [19]
Gerspacher et al.

[11] Patent Number: 5,929,067
[45] Date of Patent: Jul. 27, 1999

[54] 1-ARYL-2-ACYLAMINO-ETHANE COMPOUNDS AND THEIR USE AS NEUROKININ ESPECIALLY NEUROKININ 1 ANTAGONISTS

[75] Inventors: Marc Gerspacher, Gipf-Oberfrick; Andreas Von Sprecher, Oberwil; Silvio Roggo, Muttenz; Robert Mah, Allschwil; Silvio Ofner, Münchenstein; Siem Jacob Veenstra, Basel, all of Switzerland; Claudia Betschart, Takarazuka, Japan; Yves Auberson, Allschwil; Walter Schilling, Himmelried, both of Switzerland

[73] Assignee: Novartis AG, Basel, Switzerland

[21] Appl. No.: 08/913,352

[22] PCT Filed: Feb. 9, 1996

[86] PCT No.: PCT/EP96/00555

§ 371 Date: Aug. 21, 1997

§ 102(e) Date: Aug. 21, 1997

[87] PCT Pub. No.: WO96/26183

PCT Pub. Date: Aug. 29, 1996

[30] Foreign Application Priority Data

Feb. 22, 1995 [EP] European Pat. Off. ............... 95810117

[51] Int. Cl.⁶ .................. A61K 31/55; C07D 223/10; C07D 223/12
[52] U.S. Cl. .................. 514/212; 540/485; 540/527
[58] Field of Search .................. 540/485, 527; 514/212

[56] References Cited

U.S. PATENT DOCUMENTS 5,217,996   6/1993   Ksander .................. 514/533

FOREIGN PATENT DOCUMENTS

| 0 532 456 A1 | 3/1993 | European Pat. Off. |
| 532546 | 3/1993 | European Pat. Off. |
| 93/01169 | 1/1993 | WIPO |
| 9301169 | 1/1993 | WIPO |

OTHER PUBLICATIONS

Angus M. MacLeod, et al., J. Med. Chem. vol. 36, 1993, pp. 2044–2045.
Cs. Somlai and L. Baláspiri, J. Prakt. Chem., vol. 336, 1994, pp. 525–529.
S. Natarajan, et al., "Nonhydrolyzable Tripeptide Analogs as Angiotensin–Converting Enzyme Inhibitors," The Squibb Institute for Medical Research, Princeton, NJ, pp. 429–433.
Macleod et al., (J. Med. Chem., vol. 36, No. 14 1993, pp. 2044–2045).
Somlai et al., (CVA 122:291495, J. Prakt. Chem./Chem.–Ztg. (1994), vol. 336(6), 525–9.

*Primary Examiner*—Jose' G. Dees
*Assistant Examiner*—Sabiha N. Qazi
*Attorney, Agent, or Firm*—Carol A. Loeschorn

[57] ABSTRACT

1-Aryl-2-acylaminoethane compounds of formula I

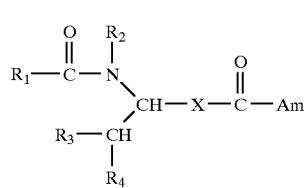

(I)

wherein $R_1$–$R_4$, X and Am are as defined in the description, have valuable pharmaceutical properties and are especially effective as NK-1 antagonists.

10 Claims, No Drawings

1-ARYL-2-ACYLAMINO-ETHANE COMPOUNDS AND THEIR USE AS NEUROKININ ESPECIALLY NEUROKININ 1 ANTAGONISTS

This is a 371 of PCT NO. EP96/00555, filed Feb. 9, 1996. The invention relates to compounds of formula I

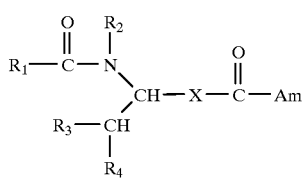

wherein
$R_1$ is aryl or heteroaryl;
$R_2$ is hydrogen, lower alkyl or aryl-lower alkyl;
$R_3$ is hydrogen, lower alkyl, aryl or heteroaryl;
$R_4$ is aryl or heteroaryl;
X is $C_1$–$C_7$alkylene, $C_2$–$C_7$alkenylene or $C_4$–$C_7$alkanedienylene, and
Am is an unsubstituted or mono- or di-substituted amino group, a disubstituted amino group being understood as including also an amino group in which the amino nitrogen is bonded into a ring, and salts thereof, to processes for the preparation of those compounds, to pharmaceutical compositions comprising those compounds, and to the use of those compounds in the therapeutic treatment of the human or animal body or in the manufacture of pharmaceutical compositions.

The general terms used hereinabove and hereinbelow preferably have the following meanings within the scope of this Application:

As already mentioned, a disubstituted amino group Am is to be understood as being also an amino group in which the amino nitrogen is bonded into a ring. That ring may be, for example, a saturated, partially unsaturated or aromatic ring. Such a ring contains—including the amino nitrogen—preferably from 3 to 8 ring members. In addition to the amino nitrogen, the ring may contain further hetero atoms, for example nitrogen, oxygen and/or sulfur atoms, and is unsubstituted or substituted.

Am is especially an amino group —$NR_5R_6$ wherein $R_5$ is hydrogen, unsubstituted or substituted lower alkyl, unsubstituted or substituted lower alkenyl, unsubstituted or substituted lower alkynyl, unsubstituted or substituted cycloalkyl, unsubstituted or substituted (aza, oxa or thia)-cycloalkyl, unsubstituted or substituted benzo-(aza, oxa or thia)-cycloalkyl, aryl, partially hydrated heteroaryl, heteroaryl or (unsubstituted or substituted lower alkyl, unsubstituted or substituted lower alkenyl, aryl or heteroaryl)-sulfonyl; and $R_6$ is hydrogen, unsubstituted or substituted lower alkyl, unsubstituted or substituted lower alkenyl, unsubstituted or substituted lower alkynyl, aryl, heteroaryl or acyl; or when the radicals $R_5$ and $R_6$ together with the amino nitrogen form a ring—Am may also be an aza-(cycloalkyl, cycloalkenyl, cycloalkynyl, partially hydrated heteroaryl or heteroaryl) radical, bonded via a ring nitrogen atom, which in addition to the amino nitrogen may contain further hetero atoms selected from nitrogen, oxygen and sulfur atoms and which is unsubstituted or substituted.

The term "lower" denotes a radical having up to and including 7 and especially up to and including 4 carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl or methyl.

Substituted lower alkyl is to be understood as being lower alkyl that is substituted one or more times, especially from 1 to 3 times, by any desired substituent(s). Substituents that may be mentioned by way of example are: aryl, partially hydrated heteroaryl, heteroaryl, cycloalkyl, (aza, oxa or thia)-cycloalkyl, benzo-(aza, oxa or thia)-cycloalkyl, carboxy, lower alkoxycarbonyl, carbamoyl, lower alkylcarbamoyl, di-lower alkylcarbamoyl, cyano, amino, lower alkylamino, di-lower alkylamino, piperidino, morpholino, thiomorpholino, hydroxy, lower alkoxy, halogen, lower alkanoyl and benzoyl.

Substituted lower alkenyl is to be understood as being lower alkenyl that is substituted one or more times, especially once, by any desired substituent(s). Substituents that may be mentioned by way of example are: aryl, heteroaryl, carboxy and lower alkoxycarbonyl.

Substituted lower alkynyl is to be understood as being lower alkynyl that is substituted one or more times, especially once, by any desired substituent(s). Substituents that may be mentioned by way of example are: aryl, heteroaryl, carboxy and lower alkoxycarbonyl.

Halogen is, for example, chlorine, bromine or fluorine, but may also be iodine.

Acyl is, for example, lower alkanoyl, substituted lower alkanoyl, e.g. halo-lower alkanoyl, aryl-carbonyl, aryl-lower alkanoyl, heteroaryl-carbonyl or heteroaryl-lower alkanoyl. In particular, acyl is lower alkanoyl.

Lower alkanoyl is, for example, acetyl, propionyl or pivaloyl, but may also be, for example, formyl.

Carbamoyl is —$CONH_2$. Oxo is a group =O.

Aryl is, for example, phenyl or naphthyl, each of which is unsubstituted or substituted, for example as indicated below for phenyl. Aryl is preferably phenyl that is unsubstituted or substituted by one or more, especially from 1 to 3, substituents from the group consisting of halogen, lower alkyl, halo-lower alkyl, (hydroxy or lower alkanoyloxy)-lower alkyl, lower alkoxy-lower alkyl, (amino or lower alkanoylamino)-lower alkyl, lower alkylamino-lower alkyl, di-lower alkylamino-lower alkyl, (piperidinyl, piperazinyl, morpholinyl or thiomorpholinyl)-lower alkyl, (imidazolyl or pyridyl)-lower alkyl, mercapto-lower alkyl, lower alkyl-(thio, sulfinyl or sulfonyl)-lower alkyl, carboxy-lower alkyl, lower alkoxycarbonyl-lower alkyl, carbamoyl-lower alkyl, lower alkylcarbamoyl-lower alkyl, di-lower alkylcarbamoyl-lower alkyl, lower alkenyl, lower alkynyl, cycloalkyl, (hydroxy or lower alkyl)-cycloalkyl, cycloalkyl-lower alkyl, phenyl, hydroxy, lower alkoxy, phenyl-lower alkoxy, lower alkanoyloxy, $C_1$–$C_3$alkylenedioxy, phenyl-lower alkoxy, carboxy-lower alkoxy, lower alkoxycarbonyl-lower alkoxy, carbamoyl-lower alkoxy, lower alkylcarbamoyl-lower alkoxy, di-lower alkylcarbamoyl-lower alkoxy, lower alkenyloxy, amino, lower alkylamino, di-lower alkylamino, lower alkanoylamino, piperidinyl, piperazinyl, morpholinyl, thiomorpholinyl, mercapto, lower alkyl-(thio, sulfinyl or sulfonyl), carboxy-lower alkylthio, lower alkoxycarbonyl-lower alkylthio, phenylthio, phenyl-lower alkylthio, carboxy, lower alkoxycarbonyl, carbamoyl, lower alkylcarbamoyl, di-lower alkyl-carbamoyl, cyano, nitro, lower alkanoyl, halo-lower alkanoyl and benzoyl. The phenyl and benzoyl groups contained in the above list of phenyl substituents are preferably unsubstituted, but may themselves likewise be substituted, for example by 1 or 2 substituents selected from the group lower alkyl, trifluoromethyl, halogen, hydroxy and lower alkoxy. The piperazinyl groups contained in the above list of phenyl substituents are preferably unsubstituted, but may themselves likewise be substituted, for example at the nitrogen by lower alkyl, phenyl-lower alkyl, phenyl or lower alkanoyl. In particular, aryl is phenyl that is unsubstituted or substituted by 1 or 2 substituents selected from lower alkyl, trifluoromethyl, halogen, hydroxy and lower alkoxy.

Heteroaryl is, for example, a 5- or 6-membered, monocyclic aromatic heterocycle or a bicycle that is composed of a 5- or 6-membered, monocyclic aromatic heterocycle and a fused-on benzene ring, and is, for example, pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzotriazolyl, benzofuranyl, benzothienyl, benzoxazolyl, benzothiazolyl, quinolinyl or isoquinolinyl. Heteroaryl radicals are unsubstituted or substituted, for example by one or more, especially from 1 to 3, substituents selected from the group consisting of lower alkyl, halo-lower alkyl, halogen, hydroxy, lower alkoxy, amino, lower alkylamino, di-lower alkylamino, nitro, lower alkanoyl, halo-lower alkanoyl, carboxy, lower alkoxycarbonyl, carbamoyl, lower alkylcarbamoyl, di-lower alkylcarbamoyl and cyano.

Partially hydrated heteroaryl is, for example, a heteroaryl radical as defined above that contains at least one hydrated double bond. It represents, for example, dihydropyrrolyl, dihydropyrazolyl, dihydroimidazolyl, dihydrofuranyl, dihydrothienyl, dihydrooxazolyl, dihydrothiazolyl, dihydropyridyl or dihydropyrimidinyl. A partially hydrated heteroaryl radical may be unsubstituted or substituted by e.g. from 1 to 5, especially 1 to 3, radicals selected from e.g. lower alkyl, halo-lower alkyl, halogen, hydroxy, lower alkoxy, amino, lower alkylamino, di-lower alkylamino, nitro, lower alkanoyl, halo-lower alkanoyl, carboxy, lower alkoxycarbonyl, carbamoyl, lower alkylcarbamoyl, di-lower alkylcarbamoyl, cyano, phenyl, (lower alkyl, trifluoromethyl, halogen, hydroxy or lower alkoxy)-phenyl and oxo.

$C_1$–$C_7$Alkylene is e.g. unbranched $C_1$–$C_7$alkylene, for example 1,2-ethylene, 1,3-propylene or 1,4-butylene, but it may also be branched, for example 1,1-ethylene, 1,2-propylene or 1,2-or 1,3-butylene. $C_1$–$C_7$Alkylene is especially 1,2-ethylene, 1,3-propylene or 1,2-propylene.

$C_2$–$C_7$Alkenylene is e.g. unbranched $C_2$–$C_7$alkenylene, for example 1,2-ethenylene, 1,3-propenylene or 1,4-butenylene, but it may also be branched, for example 1,2-propenylene or 1,3-butenylene. $C_2$–$C_7$Alkenylene is especially 1,2-ethenylene or 1,2-propenylene, and in particular 1,2-ethenylene.

$C_4$–$C_7$Alkanedienylene is preferably unbranched $C_4$–$C_7$alkanedienylene, for example 1,4-butadienylene or 1,5-pentadienylene; but it may also be branched, for example 1,4-pentadienylene. $C_4$–$C_7$Alkanedienylene is especially 1,4-butadienylene.

Halo-lower alkyl is, for example, halomethyl, for example chloromethyl, or, for example, trifluoromethyl. Halo-lower alkyl is especially trifluoromethyl.

Halo-lower alkanoyl is, for example, trifluoroacetyl.

Lower alkenyl is, for example, ethenyl(=vinyl), allyl, 1-propenyl, isopropenyl, 2- or 3-methylallyl or 3-butenyl.

Lower alkynyl is, for example, ethynyl, propargyl or 2-butynyl.

$C_3$–$C_7$Alkenyl and $C_3$–$C_7$alkynyl each as a meaning of $R_5$ or $R_6$ are preferably bonded to the amide nitrogen via a sp$^3$-carbon and are then, for example, allyl, 2-methyl-allyl or propargyl, respectively.

Cycloalkyl contains, for example, from 3 to 8, preferably from 3 to 7, ring carbon atoms and is, for example, cyclopropyl, cyclobutyl, cyclopentyl, cyclohexyl or cycloheptyl. "$C_5$–$C_7$-Cycloalkyl", $C_3$–$C_8$-cycloalkyl" etc. mean a cycloalkyl radical having the indicated number of ring carbon atoms. Cycloalkyl preferably is unsubstituted but may also be substituted, for example by the substituents indicated above for lower alkyl, or, more especially, by one or two substituents selected from lower alkyl, trifluoromethyl, halogen, hydroxy and lower alkoxy.

(Aza, oxa or thia)-cycloalkyl may contain e.g. one or two, especially one, ring hetero atom(s). It contains, for example, from 3 to 8, preferably from 5 to 7, ring atoms including the heteroatom(s). (Aza, oxa or thia)-cycloalkyl that is unsubstituted or substituted is, for example, pyrrolidin-(2 oder 3)-yl, tetrahydrofuran-(2 oder 3)-yl, tetrahydrothien-(2 oder 3)-yl, piperidin-(2,3 oder 4)-yl, 1-phenyl-lower alkyl4-lower alkoxycarbonyl-piperidin-4-yl, morpholin-(2 oder 3)-yl, thiomorpholin-(2 oder 3)-yl, piperazin-2-yl, azacycloheptan-2-on-3-yl, tetrahydrofuran-2-on-3-yl or tetrahydrothien-2-on-3-yl (=thiolan-2-on-3-yl). In particular, (Aza, oxa or thia)-cycloalkyl is azacycloheptan-2-on-3-yl(=hexahydro-azepin-2-on-3-yl).

Benzo-(aza, oxa or thia)-cycloalkyl is, for example, an (aza, oxa or thia)-cycloalkyl radical as defined above that contains in addition e.g. one or two, preferably one, anellated(=fused) benzo ring(s) which in turn may be unsubstituted or substituted, e.g. as indicated above for aryl radicals. In particular, benzo-(aza, oxa or thia)-cycloalkyl is 1,3,4,5-tetrahydrobenzoazepin-2-on-3-yl.

Azacycloalkan-1-yl is, for example, aziridino, pyrrolidino, piperidino, hexahydro-1H-azepino (7-membered ring) or azocano (8-membered ring).

Azacycloalkan-1-yl substituted by spiro-indolone that is unsubstituted or substituted by lower alkyl is e.g. 1-methylspiro(indol-2-on-3,4'-piperidino).

An aza-(cycloalkyl, cycloalkenyl or cycloalkynyl) radical bonded via a ring nitrogen atom is especially azacycloalkan-1-yl (see above) or azacycloalken-1-yl, for example 2,5dihydro-1H-pyrrol-1-yl, but may also be azacycloalkyn-1-yl.

Diazacycloalkan-1-yl is, for example, piperazino.

Azaheteroaryl-1-yl is, for example, pyrrol-1-yl, pyrazol-1-yl, imidazol-1-yl, triazol-1-yl, tetrazol-1-yl, indol-1-yl, benzimidazol-1-yl or benzotriazol-1-yl.

Salts of compounds of formula I are especially pharmaceutically acceptable salts. Compounds of formula I having a basic group, for example amino, can form, for example, acid addition salts with suitable mineral acids, such as hydrohalic acids, sulfuric acid or phosphoric acid, for example hydrochlorides, hydrobromides, sulfates, hydrogen sulfates or phosphates; salts with suitable aliphatic or aromatic sulfonic acids or N-substituted sulfamic acids, for example methanesulfonates, benzenesulfonates, p-toluenesulfonates or N-cyclohexylsulfamates (cyclamates); or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citrates.

Where the compounds of formula I contain an acid group, corresponding salts with bases are also possible, for example corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-lower alkylamines, such as hydroxy-lower alkyl-amines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. There come into consideration as mono-lower alkylamines, for example, ethylamine and tert-butylamine; as di-lower alkylamines, for example, diethylamine and diisopropylamine; and as tri-lower alkylamines, for example, trimethylamine and triethylamine. Corresponding hydroxy-lower alkylamines are, for example, mono-, di- and tri-ethanolamine; and hydroxy-lower alkyl-lower alkylamines are, for example, N,N-dimethylamino- and N,N-diethylamino-ethanol. Compounds of formula I having an acid group, for example carboxy, and a basic group, for example amino, can be present, for example, also in the form of internal salts, that is to say in zwitterionic form, or one part of the molecule may be in the form of an internal salt and another part may be in the form of a normal salt. Also included are salts that are unsuitable for pharmaceutical uses, since they can be used, for example, in the isolation and purification of free compounds I and the pharmaceutically acceptable salts thereof.

The compounds of formula I—including their pharmaceutically acceptable salts which are also included below—have valuable pharmacological properties. In particular, they act as neurokinin-1 antagonists (NK1 antagonists) and are therefore capable of preventing disease symptoms that are caused inter alia by the secretion of substance P and neurokinin A[=NKA].

The respiratory tract is equipped with sensory nerves that contain a number of neuropeptides, especially tachykinins and CGRP(=calcitonin gene-related peptide). The activation of the sensory nerves results in a local release of neuropeptides inside the lungs. More especially substance P and neurokinin A are secreted, which trigger an acute inflammatory reaction termed neurogenic inflammation. That inflammatory reaction proceeds mainly via NK1 receptor activation and includes especially vasodilatation, microvascular leakage, recruitment of inflammatory leukocytes and excessive secretion of mucus, and also bronchoconstriction [mainly via activation of the neurokinin 2 receptor (NK2 receptor)]. Those tachykinin effects are typical features of asthma.

The pharmacological action of the compounds of formula I is based especially on the antagonisation of the NK1 receptor, and in the case of some compounds of formula I additionally also on the antagonisation of the NK2 receptor. The compounds of formula I are therefore capable of inhibiting neurogenic inflammation and tachykinin-induced bronchoconstriction.

The advantageous effects of the compounds of formula I can be demonstrated by various in vitro or in vivo test methods. For example, in vitro they inhibit the [beta-Ala8]NKA(4–10)-induced $Ca^{2+}$ influx into ovarian cells of transfected Chinese hamsters, which express recombinant human neurokinin 2 receptors, with $IC_{50}$ values of about 1 μM. In addition, they are effective, for example, in vivo in the NK1 bronchospasm test in guinea pigs with $ED_{50}$ values of about 0.05–1 mg/kg p.o., the test compounds being given 2, 4 or 24 hours prior to the intravenous administration of 3.0 μg/kg of [Sar9,Met(O2)11]-substance P[=SarSP]. The challenge by SarSP induces an increase in intratracheal pressure in the guinea pigs. Furthermore, some of the compounds of formula I are effective also in the in vivo NK2 bronchospasm test in guinea pigs with $ED_{50}$ values of about 1 mg/kg p.o. In that case the increase in intratracheal pressure is induced by intravenous administration of 0.8 μg/kg of [beta-Ala8]NKA(4–10), the test compounds being administered, for example, 2 hours prior to the challenge.

The compounds of formula I are effective especially as antagonists of NK1 receptors. Their action on that class of receptors, their action on related receptor systems, for example NK2, and other actions not associated with the NK receptors render the compounds of formula I therapeutically useful in the prevention, the treatment or the diagnosis of a number of diseases, for example diseases of the upper and lower respiratory tract, for example bronchial asthma, allergic asthma, non-allergic asthma, allergic hypersensitivity and hypersecretion conditions, such as chronic bronchitis and cystic fibrosis; pulmonary fibrosis of various aetiologies; diseases of the pulmonary and bronchial circulation, such as pulmonary high blood pressure, angiogenesis, metastases; diseases of the gastrointestinal tract, such as Crohn's disease, Hirsprung's disease, diarrhoea, malabsorption conditions, inflammatory conditions; in affective, traumatic or inflammatory disorders of the central and peripheral nervous system, such as depression, anxiety states, migraine and other forms of cranial pain, strokes, emesis; diseases of the blood vessels, such as the cranial vessels; diseases relating to the microcirculation in various tissues, such as the skin and eyes; diseases of the immune system and of the reticulohistiocytary system, such as in the splenic and lymphatic tissues; pain and other disorders in which the action of neurokinins, tachykinins or other related substances are involved in the pathogenesis, pathology and aetiology.

As already mentioned, the compounds of formula I also act as antagonists of substance P. Substance P plays an important role in various disorders, for example in conditions of pain, in migraine and in certain disorders of the central nervous system, such as in anxiety states, emesis, schizophrenia and depression, and in certain motor disorders, such as in Parkinson's disease, and also in inflammatory diseases, such as in rheumatoid athritis, iritis and conjunctivitis, in diseases of the respiratory organs, such as in asthma and chronic bronchitis, in disorders of the gastrointestinal system, such as in ulcerative colitis and Crohn's disease, and in hypertension.

The substance-P-antagonising effects can be demonstrated, for example, as follows: in vitro, for example, the binding of $^3H$-substance P to the bovine retina in the radio receptor assay according to H. Bittiger, Ciba Foundation Symposium 91 (1982) 196–199, is inhibited with $IC_{50}$ values of from about 1 nM.

A change of behaviour is produced in gerbils by i.c.v. administration of substance P methyl ester. That effect can be inhibited in vivo after peroral administration of compounds of formula I. The test method used is the procedure according to A. Vassout et al. which was presented at the "Substance P and Related Peptides: Cellular and Molecular Physiology" congress in Worchester, Mass., 1990. In that procedure $ED_{50}$ values of about 1–5 mg/kg p.o. are obtained, thus pointing to the possibility of using compounds of formula I in the treatment of diseases of the central nervous system.

The invention relates very especially to compounds of formula I wherein
$R_1$ is phenyl or pyridyl each of which is unsubstituted or substituted by 1 or 2 substituents selected from the group lower alkyl, trifluoromethyl, halogen, hydroxy, lower alkoxy and nitro;
$R_2$ is hydrogen, lower alkyl or phenyl-lower alkyl wherein the phenyl group is unsubstituted or substituted by 1 or 2 substituents selected from the group lower alkyl, trifluoromethyl, halogen, hydroxy and lower alkoxy;

$R_3$ is hydrogen, lower alkyl, phenyl, naphthyl or indolyl, with phenyl, naphthyl and indolyl each being unsubstituted or substituted by 1 or 2 substituents selected from the group lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group lower alkyl, trifluoromethyl, halogen, hydroxy and lower alkoxy;

X is $C_1$–$C_7$alkylene, $C_2$–$C_7$alkenylene or $C_4$–$C_7$alkanedienylene; and Am is an amino group —$NR_5R_6$ wherein $R_5$ is an aryl radical selected from the group phenyl and naphthyl, that aryl radical being unsubstituted or substituted by from 1 to 3 radicals selected from lower alkyl, halo-lower alkyl, cycloalkyl, halogen, hydroxy, lower alkoxy, amino, lower alkylamino, di-lower alkylamino, piperidino, morpholino, thiomorpholino, nitro, lower alkanoyl, halo-lower alkanoyl, carboxy, lower alkoxycarbonyl, carbamoyl, lower alkylcarbamoyl, di-lower alkylcarbamoyl, cyano, N-lower alkyl-N-phenyl-lower alkylcarbamoyl; and (phenyl or pyridyl)-lower alkylcarbamoyl wherein the phenyl or pyridyl group is unsubstituted or substituted by lower alkyl, trifluoromethyl, hydroxy, lower alkoxy or halogen;

aryl-lower alkyl in which the aryl group is defined in the same manner as an aryl radical $R_5$ and which is unsubstituted or substituted by hydroxy in the lower alkyl moiety;

a heteroaryl radical selected from the group pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzotriazolyl, benzofuranyl, benzothienyl, benzoxazolyl, benzothiazolyl, benzopyranyl, quinolinyl and isoquinolinyl, that heteroaryl radical being unsubstituted or substituted by from 1 to 3 radicals selected from lower alkyl, halo-lower alkyl, halogen, hydroxy, lower alkoxy, amino, lower alkylamino, di-lower alkylamino, nitro, lower alkanoyl, halo-lower alkanoyl, carboxy, lower alkoxycarbonyl, carbamoyl, lower alkylcarbamoyl, di-lower alkylcarbamoyl, cyano, phenyl, (lower alkyl, trifluoromethyl, halogen, hydroxy or lower alkoxy)-phenyl and oxo;

heteroaryl-lower alkyl wherein the heteroaryl group is defined in the same manner as a heteroaryl radical $R_5$;

a partially hydrated heteroaryl radical selected from the group dihydropyrrolyl, dihydropyrazolyl, dihydroimidazolyl, dihydrofuranyl, dihydrothienyl, dihydrooxazolyl, dihydrothiazolyl, dihydropyridyl and dihydropyrimidinyl, that partially hydrated heteroaryl radical being unsubstituted or substituted by from 1 to 3 radicals selected from lower alkyl, halo-lower alkyl, halogen, hydroxy, lower alkoxy, amino, lower alkylamino, di-lower alkylamino, nitro, lower alkanoyl, halo-lower alkanoyl, carboxy, lower alkoxycarbonyl, carbamoyl, lower alkylcarbamoyl, di-lower alkylcarbamoyl, cyano, phenyl, (lower alkyl, trifluoromethyl, halogen, hydroxy or lower alkoxy)-phenyl and oxo;

partially hydrated heteroaryl-lower alkyl wherein the partially hydrated heteroaryl group is defined in the same manner as a partially hydrated heteroaryl radical $R_5$;

lower alkyl that is unsubstituted or substituted by from 1 to 3 radicals selected from carboxy, lower alkoxycarbonyl, carbamoyl, lower alkylcarbamoyl, di-lower alkylcarbamoyl, cyano, amino, lower alkylamino, di-lower alkylamino, piperidino, morpholino, thiomorpholino, hydroxy, lower alkoxy, halogen, lower alkanoyl and benzoyl;

$C_3$–$C_7$alkenyl that is unsubstituted or substituted by carboxy or by lower alkoxycarbonyl;

$C_3$–$C_7$alkynyl that is unsubstituted or substituted by carboxy or by lower alkoxycarbonyl;

cycloalkyl that is unsubstituted or substituted by lower alkyl, hydroxy, carboxy or by lower alkoxycarbonyl;

cycloalkyl-lower alkyl wherein the cycloalkyl group is defined in the same manner as cycloalkyl $R_5$;

(aza, oxa or thia)-cycloalkyl that is unsubstituted or substituted by oxo, lower alkyl, phenyl-lower alkyl, (lower alkyl, trifluoromethyl, halogen, hydroxy or lower alkoxy)-phenyl-lower alkyl, carboxy or lower alkoxycarbonyl;

benzo-(aza, oxa or thia)-cycloalkyl that is unsubstituted or substituted by oxo in the cycloaliphatic ring and is unsubstituted or substituted by lower alkyl, trifluoromethyl, halogen, hydroxy or lower alkoxy in the benzo ring;

lower alkylsulfonyl;

arylsulfonyl wherein the aryl group is defined in the same manner as an aryl radical $R_5$;

aryl-lower alkylsulfonyl wherein the aryl group is defined in the same manner as an aryl radical $R_5$;

lower alkenylsulfonyl;

aryl-lower alkenylsulfonyl wherein the aryl group is defined in the same manner as an aryl radical $R_5$;

pyridylsulfonyl that is unsubstituted or substituted by lower alkyl, trifluoromethyl, halogen, hydroxy, lower alkoxy, phenyl-lower alkoxy, (lower alkyl, trifluoromethyl, halogen, hydroxy or lower alkoxy)-phenyl-lower alkoxy, phenyloxy or (lower alkyl, trifluoromethyl, halogen, hydroxy or lower alkoxy)-phenyloxy;

$R_6$ is hydrogen, lower alkyl, hydroxy-lower alkyl, (carboxy, lower alkoxycarbonyl, carbamoyl, lower alkylcarbamoyl, di-lower alkylcarbamoyl or cyano)-lower alkyl, $C_3$–$C_7$alkenyl, $C_3$–$C_7$alkynyl, lower alkanoyl, halo-lower alkanoyl, phenyl-lower alkanoyl that is unsubstituted or substituted by lower alkyl, trifluoromethyl, halogen, hydroxy or lower alkoxy in the phenyl ring, or benzoyl that is unsubstituted or substituted by lower alkyl, trifluoromethyl, halogen, hydroxy or lower alkoxy;

or wherein —$NR_5R_6$ is a cyclic amino group selected from azacycloalkan-1-yl that is unsubstituted or substituted by 1 or 2 substituents selected from lower alkyl, hydroxy-lower alkyl, cyano-lower alkyl, lower alkyl-(sulfinyl or sulfonyl)-lower alkyl, phenyl-lower alkyl-(sulfinyl or sulfonyl)-lower alkyl, (lower alkyl, trifluoromethyl, halogen, hydroxy or lower alkoxy)-phenyl-lower alkyl-(sulfinyl or sulfonyl)-lower alkyl, phenyl-(sulfinyl or sulfonyl)-lower alkyl, (lower alkyl, trifluoromethyl, halogen, hydroxy or lower alkoxy)-phenyl-(sulfinyl or sulfonyl)-lower alkyl, di-lower alkylamino, lower alkanoylamino, hydroxy, lower alkoxy, carboxy, lower alkoxycarbonyl, carbamoyl, lower alkylcarbamoyl, di-lower alkylcarbamoyl, cyano, phenyl, (lower alkyl, trifluoromethyl, halogen, hydroxy or lower alkoxy)-phenyl and spiro-indolone that is unsubstituted or substituted by lower alkyl;

diazacycloalkan-1-yl that is unsubstituted or substituted by phenyl, (lower alkyl, trifluoromethyl, halogen, hydroxy or lower alkoxy)-phenyl, pyrimidinyl, (phenyl, lower alkyl-phenyl, trifluoromethyl-phenyl, halo-phenyl, hydroxy-phenyl or lower alkoxy-phenyl)-lower alkyl, (carboxy, lower alkoxycarbonyl, carbamoyl, lower alkylcarbamoyl, di-lower alkylcarbamoyl or cyano)-lower alkyl or by (azacycloalkan-1-yl)-carbonyl-lower alkyl;

morpholino;

thiomorpholino; and azaheteroaryl-1-yl selected from the group pyrrol-1-yl, pyrazol-1-yl, imidazol-1-yl, triazol-1-yl, tetrazol-1-yl, indol-1-yl, benzimidazol-1-yl and benzotriazol-1-yl, that azaheteroaryl-1-yl radical being unsubstituted or substituted by lower alkyl, di-lower alkylamino-lower alkyl, cyano-lower alkyl, hydroxy, lower alkoxy, phenyl-lower alkyloxy, lower alkylthio, lower alkanoyl or by halogen;

and salts thereof.

The invention relates in particular to compounds of formula I wherein $R_1$ is phenyl that is unsubstituted or substituted by 1 or 2 substituents selected from the group lower alkyl, trifluoromethyl, halogen, hydroxy and lower alkoxy;

$R_2$ is hydrogen, lower alkyl or phenyl-lower alkyl wherein the phenyl group is unsubstituted or substituted by 1 or 2 substituents selected from the group lower alkyl, trifluoromethyl, halogen, hydroxy and lower alkoxy;

$R_3$ is hydrogen, lower alkyl, phenyl, naphthyl or indolyl, with phenyl, naphthyl and indolyl each being unsubstituted or substituted by 1 or 2 substituents selected from the group lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group lower alkyl, trifluoromethyl, halogen, hydroxy and lower alkoxy;

X is $C_1$–$C_7$alkylene or $C_2$–$C_7$alkenylene; and

Am is an amino group —$NR_5R_6$ wherein $R_5$ is an aryl radical selected from the group phenyl and naphthyl, that aryl radical being unsubstituted or substituted by from 1 to 3 radicals selected from lower alkyl, halo-lower alkyl, halogen, hydroxy, lower alkoxy, amino, lower alkylamino, di-lower alkylamino, piperidino, morpholino, thiomorpholino, nitro, lower alkanoyl, halo-lower alkanoyl, carboxy, lower alkoxycarbonyl, carbamoyl, lower alkylcarbamoyl, di-lower alkylcarbamoyl and cyano;

aryl-lower alkyl in which the aryl group is defined in the same manner as an aryl radical $R_5$ and which is unsubstituted or substituted by hydroxy in the lower alkyl moiety;

a heteroaryl radical selected from the group pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzotriazolyl, benzofuranyl, benzothienyl, benzoxazolyl, benzothiazolyl, quinolinyl and isoquinolinyl, that heteroaryl radical being unsubstituted or substituted by from 1 to 3 radicals selected from lower alkyl, halo-lower alkyl, halogen, hydroxy, lower alkoxy, amino, lower alkylamino, di-lower alkylamino, nitro, lower alkanoyl, halo-lower alkanoyl, carboxy, lower alkoxycarbonyl, carbamoyl, lower alkylcarbamoyl, di-lower alkylcarbamoyl and cyano;

heteroaryl-lower alkyl wherein the heteroaryl group is defined in the same manner as a heteroaryl radical $R_5$;

lower alkyl that is unsubstituted or substituted by from 1 to 3 radicals selected from carboxy, lower alkoxycarbonyl, carbamoyl, lower alkylcarbamoyl, di-lower alkylcarbamoyl, cyano, amino, lower alkylamino, di-lower alkylamino, piperidino, morpholino, thiomorpholino, hydroxy, lower alkoxy, halogen, lower alkanoyl and benzoyl;

$C_3$–$C_7$alkenyl that is unsubstituted or substituted by carboxy or by lower alkoxycarbonyl;

$C_3$–$C_7$alkynyl that is unsubstituted or substituted by carboxy or by lower alkoxycarbonyl;

cycloalkyl that is unsubstituted or substituted by lower alkyl, hydroxy, carboxy or by lower alkoxycarbonyl;

cycloalkyl-lower alkyl wherein the cycloalkyl group is defined in the same manner as cycloalkyl $R_5$;

(aza, oxa or thia)-cycloalkyl that is unsubstituted or substituted by oxo; or arylsulfonyl wherein the aryl group is defined in the same manner as an aryl radical $R_5$;

$R_6$ is hydrogen, lower alkyl, hydroxy-lower alkyl, (carboxy, lower alkoxycarbonyl, carbamoyl, lower alkylcarbamoyl, di-lower alkylcarbamoyl or cyano)-lower alkyl, $C_3$–$C_7$alkenyl or $C_3$–$C_7$alkynyl;

or wherein —$NR_5R_6$ is a cyclic amino group selected from azacycloalkan-1-yl that is unsubstituted or substituted by 1 or 2 substituents selected from lower alkyl, hydroxy-lower alkyl, cyano-lower alkyl, di-lower alkylamino, lower alkanoylamino, hydroxy, lower alkoxy, phenyl and (lower alkyl, trifluoromethyl, halogen, hydroxy or lower alkoxy)-phenyl;

diazacycloalkan-1-yl that is unsubstituted or substituted by phenyl, (lower alkyl, trifluoromethyl, halogen, hydroxy or lower alkoxy)-phenyl, (phenyl, lower alkyl-phenyl, trifluoromethyl-phenyl, halo-phenyl, hydroxy-phenyl or lower alkoxy-phenyl)-lower alkyl, (carboxy, lower alkoxycarbonyl, carbamoyl, lower alkylcarbamoyl, di-lower alkylcarbamoyl or cyano)-lower alkyl or by (azacycloalkan-1-yl)-carbonyl-lower alkyl;

morpholino;

thiomorpholino; and azaheteroaryl-1-yl selected from the group pyrrol-1-yl, pyrazol-1-yl, imidazol-1-yl, triazol-1-yl, tetrazol-1-yl, indol-1-yl, benzimidazol-1-yl and benzotriazol-1-yl, that azaheteroaryl-1-yl radical being unsubstituted or substituted by lower alkyl, di-lower alkylamino-lower alkyl, cyano-lower alkyl, hydroxy, lower alkoxy, phenyl-lower alkyloxy, lower alkylthio, lower alkanoyl or by halogen;

and salts thereof.

The invention relates more especially to compounds of formula I wherein $R_1$ is phenyl that is unsubstituted or substituted by 1 or 2 substituents selected from the group lower alkyl, trifluoromethyl, halogen, hydroxy, lower alkoxy and nitro, or $R_1$ is pyridyl;

$R_2$ is hydrogen or lower alkyl;

$R_3$ is hydrogen, lower alkyl, phenyl or naphthyl, with phenyl and naphthyl each being unsubstituted or substituted by 1 or 2 substituents selected from the group lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group lower alkyl, trifluoromethyl, halogen, hydroxy and lower alkoxy;

X is $C_1$–$C_4$alkylene or $C_2$–$C_4$alkenylene, and

Am is an amino group —$NR_5R_6$ wherein $R_5$ is an aryl radical selected from the group phenyl and naphthyl, that aryl radical being unsubstituted or substituted by from 1 to 3 radicals selected from lower alkyl, cycloalkyl, halogen, hydroxy, lower alkoxy, di-lower alkylamino, morpholino, nitro and lower alkoxycarbonyl;

aryl-lower alkyl in which aryl is selected from the group phenyl, naphthyl and indolyl and which is unsubstituted or substituted in the aryl moiety by 1 or 2 radicals selected from hydroxy, lower alkoxy, halogen and amino, and is unsubstituted or substituted in the lower alkyl moiety by hydroxy;

a heteroaryl radical selected from the group pyridyl, quinolinyl, pyrimidinyl, thiazolyl, thiadiazolyl, isothiazolyl and indolyl, that heteroaryl radical being unsubstituted or substituted by 1 or 2 radicals selected from lower alkyl, halogen and halo-lower alkanoyl;

dihydropyrazolyl which is substituted by oxo and which is further unsubstituted or substituted by 1, 2 or 3 substituents selected from lower alkyl and phenyl;

heteroaryl-lower alkyl wherein heteroaryl is selected from the group pyridyl, quinolinyl, pyrimidinyl, thiazolyl, thiadiazolyl, isothiazolyl and indolyl;

benzopyranon-lower alkyl;

lower alkyl that is unsubstituted or substituted by lower alkoxycarbonyl, carbamoyl, lower alkylcarbamoyl, cyano, di-lower alkylamino, piperidino, morpholino, hydroxy or by benzoyl;

$C_3$–$C_7$alkenyl;

$C_3$–$C_7$alkynyl;

cycloalkyl that is unsubstituted or substituted by hydroxy;

cycloalkyl-lower alkyl that is unsubstituted or substituted by lower alkoxycarbonyl in the cycloalkyl moiety;

(aza, oxa or thia)-cycloalkyl that is unsubstituted or substituted by oxo, lower alkyl, phenyl-lower alkyl or lower alkoxycarbonyl;

benzo-(aza, oxa or thia)-cycloalkyl that is unsubstituted or substituted by oxo;

lower alkylsulfonyl;

phenyl-lower alkylsulfonyl wherein the phenyl ring is unsubstituted or substituted by lower alkoxycarbonyl;

lower alkenylsulfonyl that is unsubstituted or substituted by phenyl or halogen-phenyl;

phenylsulfonyl that is unsubstituted or substituted by lower alkyl, lower alkoxy, lower alkoxycarbonyl, carbamoyl, lower alkylcarbamoyl, di-lower alkylcarbamoyl, N-lower alkyl-N-phenyl-lower alkylcarbamoyl, (phenyl or lower alkoxy-phenyl)-lower alkylcarbamoyl or pyridyl-lower alkylcarbamoyl; or pyridylsulfonyl that is unsubstituted or substituted by phenyloxy;

$R_6$ is hydrogen, lower alkyl, hydroxy-lower alkyl, cyano-lower alkyl or $C_3$–$C_7$alkenyl;

or wherein —$NR_5R_6$ is a cyclic amino group selected from piperidino that is unsubstituted or substituted by 1 or 2 substituents selected from lower alkanoylamino, phenyl, lower alkyl, hydroxy-lower alkyl, di-lower alkylamino, hydroxy, lower alkoxy, carbamoyl, phenylsulfinyl-lower alkyl or spiro-indolone which is unsubstituted or substituted by lower alkyl;

azocano;

aziridino that is unsubstituted or substituted by lower alkyl;

piperazino that is unsubstituted or substituted by phenyl, lower alkoxy-phenyl, pyrimidinyl, halophenyllower alkyl or by (azacycloalkan-1-yl)-carbonyl-lower alkyl;

morpholino;

indol-1-yl that is unsubstituted or substituted by lower alkyl, lower alkanoyl, di-lower alkylamino-lower alkyl or by phenyl-lower alkyloxy;

benzimidazol-1-yl that is unsubstituted or substituted by lower alkylthio or by cyano-lower alkyl;

imidazol-1-yl that is unsubstituted or substituted by lower alkyl;

1,2,4-triazol-1-yl; and benzotriazol-1-yl;

and pharmaceutically acceptable salts thereof.

The invention relates most especially to compounds of formula I wherein $R_1$ is phenyl that is unsubstituted or substituted by 1 or 2 substituents selected from the group lower alkyl, trifluoromethyl, halogen, hydroxy and lower alkoxy;

$R_2$ is hydrogen or lower alkyl;

$R_3$ is hydrogen, lower alkyl, phenyl or naphthyl, with phenyl and naphthyl each being unsubstituted or substituted by 1 or 2 substituents selected from the group lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group lower alkyl, trifluoromethyl, halogen, hydroxy and lower alkoxy;

X is $C_1$–$C_4$alkylene or $C_2$–$C_4$alkenylene, and

Am is an amino group —$NR_5R_6$ wherein $R_5$ is an aryl radical selected from the group phenyl and naphthyl, that aryl radical being unsubstituted or substituted by from 1 to 3 radicals selected from lower alkyl, halogen, hydroxy, lower alkoxy, di-lower alkylamino, morpholino, nitro and lower alkoxycarbonyl;

aryl-lower alkyl in which aryl is selected from the group phenyl, naphthyl and indolyl and which is unsubstituted or substituted in the aryl moiety by 1 or 2 radicals selected from hydroxy, lower alkoxy and halogen, and is unsubstituted or substituted in the lower alkyl moiety by hydroxy;

a heteroaryl radical selected from the group pyridyl, quinolinyl, pyrimidinyl, thiazolyl, thiadiazolyl, isothiazolyl and indolyl, that heteroaryl radical being unsubstituted or substituted by 1 or 2 radicals selected from lower alkyl, halogen and halo-lower alkanoyl;

heteroaryl-lower alkyl wherein heteroaryl is selected from the group pyridyl, quinolinyl, pyrimidinyl, thiazolyl, thiadiazolyl, isothiazolyl and indolyl;

lower alkyl that is unsubstituted or substituted by lower alkoxycarbonyl, carbamoyl, cyano, di-lower alkylamino, piperidino, morpholino, hydroxy or by benzoyl;

$C_3$–$C_7$alkenyl;

$C_3$–$C_7$alkynyl;

cycloalkyl that is unsubstituted or substituted by hydroxy;

cycloalkyl-lower alkyl that is unsubstituted or substituted by lower alkoxycarbonyl in the cycloalkyl moiety;

(aza, oxa or thia)-cycloalkyl that is unsubstituted or substituted by oxo; or (phenyl or lower alkyl-phenyl)-sulfonyl;

$R_6$ is hydrogen, lower alkyl, hydroxy-lower alkyl, cyano-lower alkyl or $C_3$–$C_7$alkenyl;

or wherein —$NR_5R_6$ is a cyclic amino group selected from piperidino that is unsubstituted or substituted by 1 or 2 substituents selected from lower alkanoylamino, phenyl, lower alkyl, hydroxy-lower alkyl, di-lower alkylamino and hydroxy;

azocano;

aziridino that is unsubstituted or substituted by lower alkyl;

piperazino that is unsubstituted or substituted by phenyl, lower alkoxy-phenyl, halophenyl-lower alkyl or by (azacycloalkan-1-yl)-carbonyl-lower alkyl;

morpholino;

indol-1-yl that is unsubstituted or substituted by lower alkyl, lower alkanoyl, di-lower alkylamino-lower alkyl or by phenyl-lower alkyloxy;

benzimidazol-1-yl that is unsubstituted or substituted by lower alkylthio or by cyano-lower alkyl;

imidazol-1-yl that is unsubstituted or substituted by lower alkyl;

1,2,4-triazol-1-yl; and benzotriazol-1-yl;

and pharmaceutically acceptable salts thereof.

Of particular importance are the compounds of formula I wherein $R_1$ is 3,5-bistrifluoromethylphenyl, $R_2$ is methyl, the group —$CHR_3R_4$ is benzyl, 4-chlorobenzyl, 2-naphthylmethyl, diphenylmethyl, 1H-indol-3-ylmethyl or 1-methyl-indol-3-ylmethyl, X is 1,2-ethylene or 1,2-ethenylene, and Am is an amino group —$NR_5R_6$ wherein $R_5$ is pyridyl-$C_1$–$C_4$alkyl; $C_1$–$C_7$alkyl that is unsubstituted or substituted by hydroxy; cycloalkyl having 5 to 7 ring carbon atoms;

(aza, oxa or thia)-cycloalkyl having 5 to 7 ring atoms including the heteroatom(s) and being unsubstituted or substituted by oxo; benzo-(aza, oxa or thia)-cycloalkyl having 5 to 7 ring atoms including the heteroatom(s) in the heterocyclic ring and being unsubstituted or substituted by oxo; and $R_6$ is hydrogen or $C_1$–$C_7$alkyl; and pharmaceutically acceptable salts thereof.

Special mention should be made of each of the following sub-groups of a group of compounds of formula I:

(a) compounds of formula I wherein $R_1$ is phenyl that is disubstituted in the 3- and 5-positions; (b) compounds of formula I wherein $R_1$ is 3,5-bistrifluoromethylphenyl, 3,5-dimethylphenyl or 3,5-dihalophenyl; (c) compounds of formula I wherein $R_1$ is 3,5-bistrifluoromethylphenyl; (d) compounds of formula I wherein $R_2$ is lower alkyl; (e) compounds of formula I wherein $R_2$ is methyl; (f) compounds of formula I wherein the group —$CHR_3R_4$ is benzyl, 4-chlorobenzyl, 2-naphthylmethyl, diphenylmethyl, 1H-indol-3-ylmethyl or 1-methyl-indol-3-ylmethyl; (g) compounds of formula I wherein X is —CH=CH—, —$CH_2$—, —$(CH_2)_2$— or —$(CH_2)_3$—; (h) compounds of formula I wherein X is —CH=CH—, —$CH_2$—, —$(CH_2)_2$—, —$CH_2$—CH(—$CH_3$)— [wherein CH(—$CH_3$)— is bonded to —C(=O)—Am and —$CH_2$— is bonded to >CH in formula I], —CH=C(—$CH_3$)— [wherein C(—$CH_3$)— is bonded to —C(=O)—Am and —CH is bonded to >CH in formula I] or —$(CH_2)_3$—; (i) compounds of formula I wherein Am is an amino group —$NR_5R_6$ wherein $R_5$ is pyridyl-lower alkyl, $C_5$–$C_7$cycloalkyl, azacycloheptan-2-on-3-yl(=hexahydro-azepin-2-on-3-yl), 1-hydroxymethyl-2-methyl-propyl or 1-hydroxymethyl-3-methyl-butyl and $R_6$ is as defined in that group of compounds of formula I; (j) compounds of formula I wherein Am is an amino group —$NR_5R_6$ wherein $R_5$ is azacycloheptan-2-on-3-yl(=hexahydro-azepin-2-on-3-yl) or cyclohexyl and $R_6$ is hydrogen; (k) compounds of formula I wherein X is $C_1$–$C_4$alkylene or $C_2$–$C_4$alkenylene; (l) compounds of formula I wherein Am is a non-cyclic amino group —$NR_5R_6$ wherein $R_5$ is other than hydrogen and $R_6$ is as defined in that group of compounds of formula I.

The invention relates especially to the specific compounds described in the Examples and salts thereof.

The compounds of formula I can be prepared in a manner known per se, for example by (A) N-acylating a compound of formula II

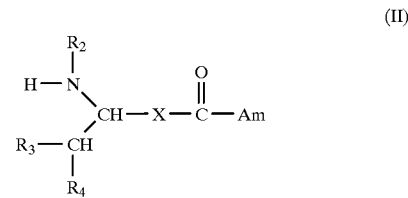

(II)

with a carboxylic acid $R_1$—C(=O)—OH, or with a reactive derivative thereof, or (B) condensing a carboxylic acid of formula III

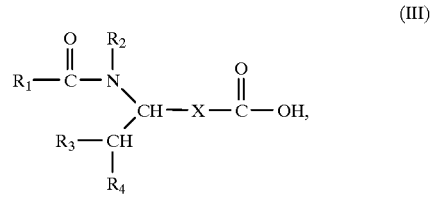

(III)

or a reactive derivative thereof, with ammonia or with a mono- or di-substituted amine, or (C)—for the preparation of a compound of formula I wherein X is $C_2$–$C_7$alkenylene or $C_4$–$C_7$alkanedienylene—as a last step forming the double bond or one of the double bonds by means of a Wittig reaction or a variant thereof, for example Wittig-Horner;

and, if desired, converting a compound of formula I into a different compound of formula I and/or, if desired, converting a resulting salt into the free compound or into a different salt and/or, if desired, converting a resulting free compound of formula I having salt-forming properties into a salt and/or, if desired, separating a resulting mixture of stereoisomers, diastereoisomers or enantiomers into the individual stereoisomers, diastereoisomers or enantiomers.

In the following more detailed description of the processes, unless otherwise indicated the symbols $R_1-R_4$, X and Am are each as defined for formula I.

Process (A)

The reaction according to Process (A) corresponds to the N-acylation known per se of primary and secondary amines, that is to say the formation of (hetero)arylcarboxylic acid amides from the corresponding carboxylic acids, or derivatives thereof, and primary and secondary amines. One of the numerous possible methods that may be mentioned is the acylation of a compound of formula II with a carboxylic acid chloride $R_1$—COCl, for example in the presence of triethylamine and 4-dimethylaminopyridine (DMAP).

A compound of formula II wherein X is $C_2-C_7$alkylene is prepared, for example, as follows: the starting material used is a compound of formula IV

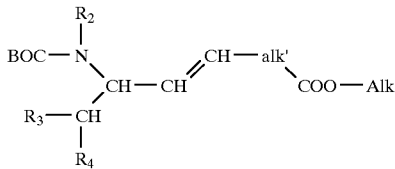

(IV)

wherein BOC is the amino-protecting group tert-butyloxycarbonyl (—COO-tert-butyl), alk' is a direct bond or $C_1-C_5$alkylene and Alk is $C_1-C_7$alkyl. First the double bond is hydrogenated, then the alkyl ester is hydrolysed to form the carboxylic acid, and then the radical —N(—$R_6$)—$R_5$ is introduced by reaction with an amine $HNR_5R_6$ [formation of —C(=O)—N(—$R_6$)—$R_5$] and finally the protecting group —BOC is removed.

A compound of formula IV can be obtained, for example, by using as starting material an alpha-amino acid derivative of formula V

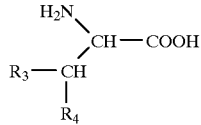

(V)

(for example $R_3$=H, $R_4$=phenyl: phenylalanine), protecting the free amino group by a protecting group "Pr" [for example BOC by reaction with $(BOC)_2O$], optionally introducing the group $R_2$, for example by N-alkylation, and esterifying the carboxylic acid radical (preferably to form a lower alkyl ester, especially the methyl ester). If desired, the introduction of the group $R_2$ and the esterification of the carboxylic acid radical may be effected in one step, for example with methyl iodide and $Ag_2O$ in DMF. The carboxylic acid ester is reduced to the corresponding aldehyde Va

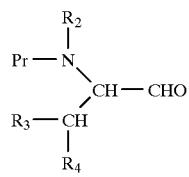

(Va)

(for example with diisobutylaluminium hydride in toluene at −78° C.) and finally reacted to form a compound of formula IV in a Wittig-Horner reaction. That can be effected, for example, by reaction with a phosphonoalkanoic acid trialkyl ester of the formula $(AlkO)_2P(=O)$-alk'-COOAlk.

A compound of formula II wherein X is $C_1$alkylene(=—$CH_2$—) is prepared, for example, as follows: using a compound of formula VI (see below) as starting material, the alkyl ester is hydrolysed to form the carboxylic acid and the radical —N(—$R_6$)—$R_5$ is introduced by reaction with an amine $HNR_5R_6$ [formation of —C(=O)—N(—$R_6$)—$R_5$].

A compound of formula II wherein X is $C_2-C_7$alkenylene is prepared, for example, as follows: using a compound of formula IV as starting material, the alkyl ester is hydrolysed to form the carboxylic acid and the radical —N(—$R_6$)—$R_5$ is introduced by reaction with an amine $HNR_5R_6$ [formation of —C(=O)—N(—$R_6$)—$R_5$] and finally the protecting group —BOC is removed.

Process (B)

The reaction in accordance with Process (B) corresponds to the formation known per se of carboxylic acid amides from the corresponding carboxylic acids, or derivatives thereof, and ammonia or primary and secondary amines. Of the large number of possible methods the following may be mentioned: (1) the reaction of a carboxylic acid of formula III with ammonia or a primary or secondary amine $HNR_5R_6$, for example in the presence of N-ethyl-N'-(3-dimethylaminopropyl)-carbodiimide hydrochloride (EDC) and 4-dimethylaminopyridine (DMAP); (2) the reaction of a carboxylic acid of formula III first with N-hydroxysuccinimide and N-ethyl-N'-(3-dimethylaminopropyl)-carbodiimide hydrochloride in the presence of DMAP to form the corresponding N-hydroxysuccinimide ester and then with the corresponding amine $HNR_5R_6$; (3) the reaction of a carboxylic acid of formula III with an amine $HNR_5R_6$, especially an aniline, in the presence of 1-propanephosphonic acid anhydride.

A compound of formula III wherein X is $C_2-C_7$alkylene is prepared, for example, as follows: using a compound of formula IV as starting material, the amino-protecting group is removed, for example in the case of BOC by reaction with trifluoroacetic acid, the amino group is acylated with a carboxylic acid $R_1$—COOH, or with a reactive derivative thereof, [analogously to Process (A)], the double bond is reduced, for example with $H_2$/palladium-on-carbon in THF and 1,2-dichlorobenzene, and finally the alkyl ester group is hydrolysed, for example with LiOH in methanol and THF.

Another method of preparing a compound of formula III wherein X is $C_2-C_7$alkylene comprises reacting an aldehyde of formula Va with a 1,3-dioxan-2-yl-alkyltriphenylphosphonium halide, for example 2-(1,3-dioxan-2-yl)-ethyltriphenylphosphonium bromide, in a Wittig reaction, hydrogenating the resulting double bond, for example with Raney nickel, oxidising the terminal 1,3-dioxan-2-yl group to the 3-hydroxypropyl ester of the corresponding carboxylic acid, for example with ozone, removing the amino-protecting group, acylating the amino group with a carboxylic acid R₁—COOH, or with a reactive derivative thereof, [analogously to Process (A)], and finally hydrolysing the 3-hydroxypropyl ester to form the carboxylic acid.

The compounds of formula III wherein X is C₂-C₇alkenylene are prepared, for example, analogously to those wherein X is C₂-C₇alkylene, that is to say likewise from compounds of formula IV, the only difference being that the double bond is not reduced.

A compound of formula III wherein X is C₁alkylene (=—CH₂—) is prepared, for example, as follows: using as starting material a compound of formula VI

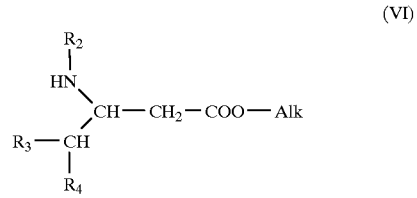

wherein Alk is lower alkyl, the amino group is acylated with a carboxylic acid R₁—COOH, or with a reactive derivative thereof, [analogously to Process (A)], and the ester group is hydrolysed to form the carboxylic acid III.

A compound of formula VI is in turn prepared, for example, as follows: a carboxylic acid R₃R₄CH—COOH is used as starting material and is reacted with a malonic acid derivative, for example bis(malonic acid monoethyl ester) magnesium salt [for example in the presence of carbonyidiimidazole]. The resulting keto ester of the formula R₃R₄CH—C(=O)—CH₂—COO—Alk is converted, for example by reaction with an amine R₂NH₂ and then with sodium cyanoborohydride, into the desired compound of formula VI.

For the preparation of a compound of formula VI it is also possible, for example, to employ the following procedure: using a compound of formula V as starting material, the amino group is protected by an amino-protecting group, for example BOC, the carboxylic acid is esterified to the methyl ester, the methyl ester is reduced to hydroxymethyl, (for example with LiBH₄), the hydroxymethyl group is mesylated and, by reaction with tetraethyl-ammonium cyanide, the corresponding cyanomethyl compound is obtained. The latter can be hydrolysed to form the carboxylic acid and converted by esterification into a compound of formula VI.

A compound of formula III wherein X is C₃alkylene [—(CH₂)₃—] is prepared, for example, as follows: using as starting material a compound of formula IVa

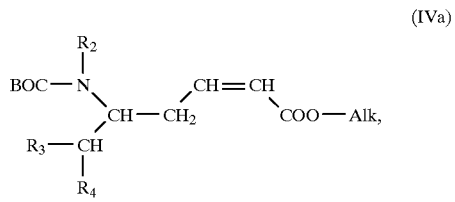

the double bond is reduced, for example with H₂/palladium-on-carbon, the amino-protecting group is removed, for example in the case of BOC by reaction with trifluoroacetic acid, the amino group is acylated with a carboxylic acid R₁—COOH, or with a reactive derivative thereof, [analogously to Process (A)], and finally the alkyl ester group is hydrolysed, for example with KOH.

A compound of formula IVa is in turn prepared, for example, starting from a compound of formula VI as follows: the lower alkylamino group is protected by the introduction of a protecting group, for example by reaction with chloroformic acid benzyl ester, the lower alkyl ester is reduced, for example with diisobutylaluminium hydride, to the aldehyde and the latter is then reacted, for example with phosphonoacetic acid triethyl ester in a Wittig-Horner reaction, to form the compound of formula IVa.

Process (C)

A possible starting compound for the Wittig-(Horner) reaction is, for example, an aldehyde of formula Va in which the amino-protecting group is removed and which is then N-acylated with a carboxylic acid R₁—COOH, or with a reactive derivative thereof, [analogously to Process (A)]. Such an aldehyde can, for example, be reacted with a phosphonoalkanoic acid dialkyl ester amide of the formula (AlkO)₂P(=O)-alk'—CO—Am in a Wittig-Horner reaction to form a compound of formula I.

Compounds of formula I can also be converted in a manner known per se into other compounds of formula I.

For example, a compound of formula I wherein R₂ is lower alkyl or aryl-lower alkyl can be obtained by N-alkylating a compound of formula I wherein R₂ is hydrogen with a compound Y₃—R₂ wherein Y₃ is hydroxy or reactive esterified hydroxy. Another possible method comprises reacting a compound of formula I wherein R₂ is hydrogen with a compound Y₄—R₂' wherein Y₄ is formyl and R₂' is a radical R₂ less a CH₂ group [R₂=—CH₂—R₂'] under reductive conditions (reductive amination).

It is also possible, for example, for compounds of formula I wherein X is C₂-C₇alkenylene to be converted by hydrogenation (reduction) into the corresponding compounds of formula I wherein X is C₂-C₇alkylene.

Compounds of formula I having R₆=H can be converted to compounds of formula I wherein R₆ is acyl, e.g. lower alkanoyl, by usual acylation methods, preferably in the presence of a strong base, e.g. sodium hydride.

If any intermediates contain interfering reactive groups, for example carboxy, hydroxy, mercapto or amino groups, those groups can temporarily be protected by readily removable protecting groups. The choice of suitable protecting groups and the manner in which they are introduced and removed are known per se and are described, for example, in J. F. W. McOmie, Protective Groups in Organic Chemistry, Plenum Press, London, New York 1973.

Salts of compounds I can be prepared in a manner known per se. For example, acid addition salts of compounds I are obtained by treatment with a suitable acid or a suitable ion exchange reagent, and salts with bases are obtained by treatment with a suitable base or a suitable ion exchange reagent. Salts of compounds of formula I can be converted into the free compounds I in customary manner: acid addition salts, for example, by treatment with a suitable basic agent or a suitable ion exchange reagent, and salts with bases, for example, by treatment with a suitable acid or a suitable ion exchange reagent.

Salts of compounds I can be converted into other salts of compounds I in a manner known per se: for example acid addition salts can be converted into other acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt being formed, for example silver chloride, is insoluble and is therefore precipitated out the reaction mixture.

Depending upon the procedure and reaction conditions, the compounds I having salt-forming properties may be obtained in free form or in the form of salts.

As a result of the dose relationship between the compounds I in free form and in the form of their salts, hereinabove and hereinbelow any reference to the free compound I or its salts is to be understood as including also the corresponding salts or the free compound I, respectively, as appropriate and expedient.

The compounds I, including the salts of salt-forming compounds, may also be obtained in the form of their hydrates and/or may include other solvents, for example solvents which may have been used for the crystallisation of compounds in solid form.

Depending upon the nature of the variables and the corresponding number of centres of asymmetry and also upon the starting materials and procedures chosen, the compounds of formula I and their salts may be obtained in the form of mixtures of stereoisomers, for example mixtures of diastereoisomers or mixtures of enantiomers, such as racemates, or possibly also in the form of pure stereoisomers. Mixtures of diastereoisomers obtainable in accordance with the process or by some other method can be separated in customary manner into mixtures of enantiomers, for example racemates, or into individual diastereoisomers, for example on the basis of the physico-chemical differences between the constituents in known manner by fractional crystallisation, distillation and/or chromatography. Advantageously the more active isomer is isolated.

Mixture of enantiomers, especially racemates, obtainable in accordance with the process or by some other method can be separated into the individual enantiomers by methods known per se, for example by recrystallisation from an optically active solvent, with the aid of micro-organisms, by chromatography and/or by reaction with an optically active auxiliary compound, for example a base, acid or alcohol, to form mixtures of diastereoisomeric salts or functional derivatives, such as esters, separation thereof and freeing of the desired enantiomer. Advantageously the more active enantiomer is isolated.

The invention relates also to those forms of the process according to which a compound obtainable as intermediate at any stage of the process is used as starting material and the remaining steps are carried out or a starting material is used in the form of a derivative or salt or, especially, is formed under the reaction conditions.

In the process of the present invention it is preferable to use those starting materials and intermediates, in each case in free form or in salt form, which result in the compounds I, or their salts, described at the beginning as being especially valuable. The invention relates also to novel starting materials and intermediates, in each case in free form or in salt form, for the preparation of the compounds I or their salts, to their use and to processes for their preparation, the variable R being as defined for the compounds I.

The invention relates also to the use of the compounds I and their pharmaceutically acceptable salts in the treatment of allergic condition and diseases, preferably in the form of pharmaceutically acceptable compositions, especially in a method for the therapeutic treatment of the animal or human body, and to such a method of treatment.

The invention relates also to pharmaceutical compositions comprising a compound I or a pharmaceutically acceptable salt thereof as active ingredient, and to processes for the manufacture thereof. Those pharmaceutical compositions are compositions for enteral, such as oral and also rectal, administration, for parenteral administration, for local administration and especially for administration by inhalation to warm-blooded animals, especially human beings, the compositions comprising the pharmacological active ingredient alone or together with customary pharmaceutical excipients. The pharmaceutical compositions comprise (in % by weight), for example, from approximately 0.001% to 100%, preferably from approximately 0.1% to approximately 50%, active ingredient.

Pharmaceutical compositions for enteral and parenteral administration are, for example, those in unit dose forms, such as dragees, tablets, capsules or suppositories, and also ampoules. They are prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture and processing the mixture or granules, if desired or necessary after the addition of suitable excipients, to form tablets or dragé cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, and also carboxymethyl starch, cross-linked polyvinylpyrrolidone, agar, or alginic acid or a salt thereof, such as sodium alginate. Excipients are especially flow-conditioners and lubricants, for example silicic acid, talc, stearic acid or salts thereof, such as magnesium or calcium stearate, and/or polyethylene glycol. Dragé cores are provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragé coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and, if desired, stabilisers. In soft capsules the active ingredient is preferably dissolved or suspended in suitable liquids, such as fatty oils, paraffin oil or liquid polyethylene glycols, it likewise being possible to add stabilisers.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilisers.

Pharmaceutical compositions for local administration are, for example, for the topical treatment of the skin: lotions, creams and ointments, that is to say liquid or semi-solid oil-in-water or water-in-oil emulsions; fatty ointments which are anhydrous; pastes, that is to say creams and ointments having secretion-absorbing powder constituents; gels which are aqueous, have a low water content or contain no water and consist of swellable, gel-forming materials; foams, that is to say liquid oil-in-water emulsions in aerosol form which are administered from pressurised containers; and tinctures having an aqueous-ethanolic base; each of which compositions may comprise further customary pharmaceutical excipients, such as preservatives. The pharmaceutical compositions for local administration are manufactured in a manner known per se by mixing the active ingredient with the pharmaceutical excipients, for example by dissolving or suspending the active ingredient in the base material or, if necessary, in a portion thereof. For the preparation of emulsions in which the active ingredient is dissolved in one of the liquid phases, the active ingredient is usually dissolved in that phase prior to emulsification; for the preparation of suspensions in which the active ingredient is suspended in the emulsion, the active ingredient is mixed with a portion of the base material after emulsification and then added to the remainder of the formulation.

The dosage of the active ingredient can depend on various factors, such as the activity and duration of action of the active ingredient, the severity of the disease to be treated and its symptoms, the mode of administration, the species, sex, age and weight of the warm-blooded animal and/or its individual condition. In a normal case the daily dose for administration, for example oral administration, to a warm-blooded animal weighing about 75 kg is estimated to be from approximately 1 mg to approximately 1000 mg, especially from approximately 5 mg to approximately 200 mg. That dose may be administered in a single dose or in several partial doses of, for example, from 10 to 100 mg.

The following Examples illustrate the invention described above. Temperatures are given in degrees Celsius; picolyl=pyridylmethyl; carbamoyl=—$CONH_2$; hexane indicates an isomeric mixture of various hexanes (for example supplied by Fluka); TLC=thin-layer chromatography; RT=room temperature.

With regard to the nomenclature used for the compounds in the Examples section which follows: for the sake of better clarity the end products are in all cases referred to as "carboxylic acid amides" even where the amide nitrogen is bonded into a ring (for example aliphatically or aromatically). If the amide nitrogen is mono- or di-substituted (but not bonded into a ring), this is expressed in each case by "N- . . . N- . . . ", for example ". . . -pentanoic acid N-(1-methyl-indol-5-yl)-amide" or " . . . -pentanoic acid N-benzyl-N-methyl-amide". If, however, the amide nitrogen is part of a ring, the "N- . . . N- . . . " and the "yl" are omitted for the substituents and the name of the ring is placed in brackets together with "amide", for example " . . . -pentanoic acid (3-acetyl-indole-1-amide)" or " . . . -pentanoic acid (4-phenyl-4-acetylamino-piperidine-amide)".

EXAMPLE 1

4-[N'-Methyl-N'-(3,5-bistrifluoromethyl-benzoyl)-amino]-5-(4-chlorophenyl)-pent-2-enoic acid N-(2-methoxy-benzyl)-amide A solution of 1.25 g of 4-(N'-methyl)-amino-5-(4-chlorophenyl)-pent-2-enoic acid N-(2-methoxy-benzyl)-amide, 1.06 g of 3,5-bistrifluoro-methyl-benzoyl chloride, 1.41 g of triethylamine and 50 mg of 4-N,N-dimethylaminopyridine in 80 ml of methylene chloride is stirred under argon at 0° for 18 hours. The reaction mixture is then diluted with 300 ml of ethyl acetate. The mixture is washed in a separating funnel with 0.1N sodium hydroxide solution, water, 0.1N hydrochloric acid and saturated NaCl solution, dried (magnesium sulfate) and concentrated by evaporation. Recrystallisation of the residue from n-pentane/ethyl acetate yields the title compound in the form of white crystals having a melting point of 163–168°. $^1$H-NMR, 400 MHz, DMSO, 120°, delta (ppm): 8.02(s, 1H), 7.87(s, 1H), 7.56(s, 2H), 7.3–7.18 (m, 6H), 6.98(d, 1H), 6.90(t, 1H), 6.70(dd, 1H), 6.21(dd, 1H), 4.9(bs, 1H), 4.37(d, 2H), 3.81(s, 3H), 3.06(m, 2H), 2.82(s, 3H).

The starting materials can be prepared as follows:

a) 4-(N'-Methyl)-amino-5-(4-chlorophenyl)-pent-2-enoic acid N-(2-methoxy-benzyl)-amide A solution of 1.8 g of 4-(N'-methyl-N'-tert-butyloxycarbonyl)-amino-5-(4-chlorophenyl)-pent-2-enoic acid N-(2-methoxy-benzyl)-amide and 10 ml of trifluoro-acetic acid in 30 ml of methylene chloride is stirred under argon at room temperature for 5 hours. The reaction mixture is then concentrated by evaporation and dissolved in 200 ml of ethyl acetate. The ethyl acetate solution is washed with 0.05N sodium hydroxide solution and saturated NaCl solution, dried (sodium sulfate), concentrated by evaporation to give a light-yellow oil and immediately reacted further.

b) 4-(N'-Methyl-N'-tert-butyloxycarbonyl)-amino-5(4-chlorophenyl)-pent-2-enoic acid N-(2-methoxy-benzyl)-amide A mixture of 2.1 g of 4-(N'-methyl-N'-tert-butyloxycarbonyl)-amino-5-(4-chlorophenyl)-pent-2-enoic acid, 0.85 g of 2-methoxy-benzylamine, 1.31 g of N-ethyl-N'-(3-dimethylaminopropyl)-carbodiimide hydrochloride, 0.83 g of 4-dimethylaminopyridine and 80 ml of methylene chloride is stirred under argon at room temperature for 16 hours and then concentrated by evaporation. The residue is chromatographed (silica gel, hexane/ethyl acetate 1:1). In this way the title compound is obtained in the form of a colourless amorphous solid. $^1$H-NMR, 200 MHz, $CDCl_3$, delta (ppm): 7.3–7.0(m, 4H), 6.95–6.7(m, 5H), 6.0(s,1H), 5.77(d, 1H), 5.0(b, 1H), 4.5(d, 2H), 3.85(s, 3H), 2.9–2.6(m, 5H), 1.3(bs, 9H).

c) 4-(N'-Methyl-N'-tert-butyloxycarbonyl)-amino-5-(4-chlorophenyl)-pent-2-enoic acid A solution of 4.0 g of 4-(N'-methyl-N'-tert-butyloxycarbonyl)-amino-5-(4-chlorophenyl)-pent-2-enoic acid ethyl ester and 2.3 g of lithium hydroxide in tetrahydrofuran/methanol/water=2/2/1 is stirred at room temperature for 18 hours and then concentrated by evaporation. The residue is dissolved in 50 ml of water, acidified to pH=2 with 0.1N hydrochloric acid and extracted twice with ethyl acetate. The combined organic phases are washed with water and saturated NaCl solution, dried (magnesium sulfate) and concentrated by evaporation to give a light-yellow oil. $^1$H-NMR, 400 MHz, DMSO,120°, delta (ppm): 7.30(d, 2H), 7.20(d, 2H), 6.80(dd, 1H), 5.81(d, 1H), 4.85(m, 1H), 2.75(d, 2H), 2.63(s, 3H), 1.35(s, 9H).

d) 4-(N'-Methyl-N'-tert-butyloxycarbonyl)-amino-5-(4-chlorophenyl)-pent-2-enoic acid ethyl ester 1.44 g of sodium hydride (approx. 55% in oil) are added in portions at 0° to a solution of 6.72 g of phosphonoacetic acid triethyl ester in 120 ml of absolute tetrahydrofuran and the mixture is stirred at that temperature for 30 minutes. A solution of 5.0 g of N'-methyl-N'-tert-butyloxycarbonyl-(4-chlorophenyl)-alaninal (in 20 ml of THF) is then added dropwise. When the dropwise addition is complete, the mixture is stirred for a further 1 hour at 0°. The reaction mixture is then poured into water and extracted twice using 150 ml of ethyl acetate each time. The combined organic phases are washed three times with water and once with saturated NaCl solution, dried (magnesium sulfate) and concentrated by evaporation. The residue is purified by chromatography (silica gel, hexane/ethyl acetate 3:1). In this way the title compound is obtained in the form of a colourless oil. $^1$H-NMR, 200 MHz, CDCl$_3$, delta (ppm): 7.35–7.05 (m, 4H), 6.90(dd, 1H), 5.85(d, 1H), 5.15(m, 0.5H), 4.90(m, 0.5H), 4.17(q, 2H), 2.90(m, 2H), 2.68(s, 3H), 1.30(m, 12H).

e) N'-Methyl-N'-tert-butyloxycarbonyl-(4-chlorophenyl)-alaninal

A solution of 10 g of N'-methyl-N'-tert-butyloxycarbonyl-(4-chlorophenyl)-alanine methyl ester in 25 ml of toluene is cooled to −78° under argon. At that temperature 7 ml of a 1M diisobutylaluminium hydride solution (in toluene) are slowly added dropwise. When the dropwise addition is complete, the mixture is stirred at that temperature for 2 hours. 1 ml of methanol and 22 ml (6 g) of a sodium potassium tartrate solution are then added to the reaction mixture. The mixture is stirred vigorously at 0° for 2 hours. The phases are then separated and the aqueous phase is extracted once more with diethyl ether. The combined organic phases are washed with water and saturated NaCl solution, dried (sodium sulfate) and concentrated by evaporation. The residue is reacted further without being purified. $^1$H-NMR, 200 MHz, CDCl$_3$, delta (ppm): 7.30–7.05(m, 4H), 4.16(m, 0.5H), 3.93(m, 0.5H), 3.25(dd, 2H), 2.90(m, 1H), 2.70 and 2.62(2s, 3H), 1.40(2s,9H).

f) N'-Methyl-N'-tert-butyloxycarbonyl-(4-chlorophenyl)-alanine methyl ester 80 g of silver(I) oxide are added, with stirring, to a solution of 20 g of tert-butyloxycarbonyl-(4-chlorophenyl) alanine in 300 ml of N,N-dimethylformamide. 10.2 ml of methyl iodide are then added drop-wise. The reaction mixture is stirred at 45° for 2 hours and at room temperature for 3 days, then diluted with 600 ml of ethyl acetate, filtered and concentrated by evaporation. The residue is purified by chromatography (silica gel, hexane/ethyl acetate 5:1). In this way the title compound is obtained in the form of a colourless oil. $^1$H-NMR, 200 MHz, CDCl$_3$, delta (ppm): 7.25(d, 2H), 7.11(d, 2H), 4.90(bs, 0.5H), 4.47(bs, 0.5H), 3.72(s, 3H), 3.25(m, 1H), 3.00(dd, 1H), 2.70(s, 3H), 1.35(s, 9H).

In the same manner as that described in Example 1 a)–f), using the appropriate amines in Step 1b) it is also possible to prepare also the following compounds:

EXAMPLE 1/1
4-[N'-Methyl-N'-(3,5-bistrifluoromethyl-benzoyl)-amino]-5-(4-chlorophenyl)pent-2-enoic acid N,N-dimethylamide: white crystals having a melting point of 152–153°.

EXAMPLE 1/2
4-[N'-Methyl-N'-(3,5-bistrifluoromethyl-benzoyl)-amino]-5-(4-chlorophenyl)pent-2-enoic acid N-[2-(2-pyridyl)-ethyl]-amide A solution of 1.20 g of 4-(N'-methyl)-amino-4-(5-chlorophenyl)-pent-2-enoic acid N-[2-(2-pyridyl)-ethyl]-amide, 1.06 g of 3,5-bistrifluoro-methyl-benzoyl chloride, 1.41 g of triethylamine and 50 mg of 4-N,N-dimethylaminopyridine in 80 ml of methylene chloride is stirred under argon at 0° for 18 hours. The reaction mixture is then diluted with 300 ml of ethyl acetate. The mixture is washed in a separating funnel with 0.1N sodium hydroxide solution, water, and saturated NaCl solution, dried (magnesium sulfate) and concentrated by evaporation. The residue is chromatographed (silica gel, methanol/ethyl acetate 1:10). In this way the title compound is obtained in the form of a white amorphous solid. R$_f$ value=0.17 (ethyl acetate). $^1$H-NMR, 400 MHz, DMSO, 120°, delta (ppm): 8.47(d, 1H), 8.02(s, 1H), 7.68(bs, 1H), 7.62(t, 1H), 7.47(s, 2H), 7.3–7.17(m, 6H), 6.67(dd, 1H), 6.11(d, 1H), 4.9(b,$_1$H), 3.56(m, 2H), 3.06(m, 2H), 2.92(t, 2H), 2.81(s, 3H).

The starting material can be prepared as follows:

a) 4-(N'-Methyl)-amino-4-(5-chlorophenyl)-pent-2-enoic acid N-[2-(2-pyridyl)-ethyl]-amide A solution of 1.8 g of 4-(N'-methyl-N'-tert-butyloxycarbonyl)-amino-4-(5-chlorophenyl)-pent-2-enoic acid N-[2-(2-pyridyl)-ethyl]-amide and 10 ml of trifluoroacetic acid in 30 ml of methylene chloride is stirred at room temperature under argon for 5 hours. The reaction mixture is then concentrated by evaporation and dissolved in 200 ml of ethyl acetate. The ethyl acetate solution is washed with 0.05N sodium hydroxide solution and saturated NaCl solution, dried (sodium sulfate), concentrated by evaporation to give a light-yellow oil and immediately reacted further.

b) 4-(N'-Methyl-N'-tert-butyloxycarbonyl)-amino-4-(5-chlorophenyl)-pent-2-enoic acid N-[2(2-pyridyl)-ethyl]-amide A mixture of 2.1 g of 4-(N'-methyl-N'-tert-butyloxycarbonyl)-amino-4-(5-chlorophenyl)-pent-2-enoic acid (see Example 1c), 0.85 g of 2-(2-pyridyl)-ethylamine, 1.31 g of N-ethyl-N'-(3-dimethylaminopropyl)-carbodiimide hydrochloride, 0.83 g of 4-dimethylaminopyridine and 80 ml of methylene chloride is heated at room temperature for 16 hours and then concentrated by evaporation. The residue is chromatographed (silica gel, ethyl acetate). In this way the title compound is obtained in the form of a colourless oil; R$_f$ value=0.2 (ethyl acetate).

EXAMPLE 1/3
4-[N'-Methyl-N'-(3,5-bistrifluoromethyl-benzoyl)-amino]-5-(4-chlorophenyl)-pent-2-enoic acid N-(1-methyl-3-trifluoroacetyl-indol-5-yl)-amide: white crystals having a melting point of 138–140°.

EXAMPLE 2
4-[N'-Methyl-N'-(3,5-bistrifluoromethyl-benzoyl)-amino]-5-(4-chlorophenyl)-pent-2-enoic acid N-(2-methoxy-benzyl)-amide This is the compound of Example 1. It can be prepared also by the following synthesis method: a mixture of 0.493 g of 4-[N'-methyl-N'-(3,5-bistrifluoromethyl-benzoyl)-amino]-5-(4-chlorophenyl)-pent-2-enoic acid, 0.137 g of 2-methoxy-benzylamine, 0.21 g of N-ethyl-N'-(3-dimethylaminopropyl)-carbodiimide hydrochloride, 0.134 g of 4-dimethylaminopyridine and 10 ml of methylene chloride is stirred at room temperature under argon for 16 hours and then concentrated by evaporation. The residue is chromatographed (silica gel, hexane/ethyl acetate 1:1). In this way the title compound is obtained in the form of a colourless amorphous solid. $^1$H-NMR, 200 MHz, CDCl$_3$, delta (ppm): 7.3–7.0(m, 4H), 6.95–6.7(m, 5H), 6.0(s,1H), 5.77(d, 1H), 5.0(b, 1H), 4.5(d, 2H), 3.85(s, 3H), 2.9–2.6(m, 5H), 1.3(bs, 9H).

The starting materials can be prepared as follows:

a) 4-[N'-Methyl-N'-(3,5-bistrifluoromethyl-benzoyl)-amino]-5-(4-chlorophenyl)-pent-2-enoic acid A solution of 20 g of 4-[N'-methyl-N'-(3,5-bistrifluoromethyl-benzoyl)-amino]-5-(4-chlorophenyl)- pent-2-enoic acid ethyl ester and 15 g of lithium hydroxide monohydrate in 100 ml of THF/methanol/water 3:3:1 is stirred at room temperature for 4 hours, and then 200 ml of water and 1N hydrochloric acid are added (pH value approx. 2). The mixture is extracted twice with ethyl acetate. The combined organic phases are washed with water and saturated NaCl solution, dried (magnesium sulfate) and concentrated by evaporation. The title compound is obtained in the form of a colourless oil which can be used further without being further purified.

b) 4-[N'-Methyl-N'-(3,5-bistrifluoromethyl-benzoyl)-amino]-5-(4-chlorophenyl)-pent-2-enoic acid ethyl ester 22 g of 3,5-bis-trifluoromethyl-benzoyl chloride, 16 g of triethylamine and 1 g of 4-dimethylaminopyridine are added at 0° under argon to a solution of 30 g of 4-(N'-methyl)-amino-5-(4-chlorophenyl)-pent-2-enoic acid ethyl ester trifluoroacetate in 250 ml of methylene chloride. The reaction mixture is stirred at 0° for 18 hours and then poured into water. The organic phase is separated off and the aqueous phase is extracted twice more with methylene chloride. The combined organic phases are washed with 0.01N hydrochloric acid, water and saturated NaCl solution, dried (magnesium sulfate) and concentrated by evaporation. The residue is chromatographed (silica gel, hexane/ethyl acetate 1:1). In this way the title compound is obtained in the form of a colourless oil. $^1$H-NMR, 400 MHz, DMSO, 120°, delta (ppm): 8.01(s, 1H), 7.59(s, 2H), 7.30(td, 2H), 7.22(d, 2H), 6.96(dd, 1H), 6.05(d, 1H), 5.0(b, 1H), 4.20(q, 2H), 3.1(m, 2H), 2.81(s, 3H), 2.35(m, 2H), 1.25(t, 3H).

c) 4-(N'-Methyl)-amino-5-(4-chlorophenyl)-pent-2-enoic acid ethyl ester trifluoroacetate 60 ml of trifluoroacetic acid are added dropwise to a solution of 50 g of 4-(N'-methyl-N'-tert-butyloxycarbonyl)-amino-5-(4-chlorophenyl)-pent-2-enoic acid ethyl ester in 200 ml of methylene chloride. The reaction mixture is stirred at room temperature for 4 hours and then concentrated by evaporation. The residue is dissolved in 300 ml of toluene and again concentrated by evaporation. That step is repeated twice more. The crude product so obtained can be processed further without being further purified.

Analogously to Example 2, using the appropriate amines (instead of 2-methoxy-benzyl-amine) it is also possible to obtain the following compounds:

EXAMPLE 2/1
4-[N'-Methyl-N'-(3,5-bistrifluoromethyl-benzoyl)-amino]-5-(4-chlorophenyl)-pent-2-enoic acid N-(1-methylindol-5-yl)-amide: white crystals having a melting point of 232–234°.

EXAMPLE 2/2
4-[N'-Methyl-N'-(3,5-bistrifluoromethyl-benzoyl)-amino]-5-(4-chlorophenyl)-pent-2-enoic acid N-(2-pyridylmethyl)-amide: amorphous white solid. $^1$H-NMR, 500 MHz, DMSO, 140°, delta (ppm): 8.50(d, 1H), 8.12(bs, 1H), 8.02(s, 1H), 7.72(t, 1H), 7.58(s, 2H), 7.3–7.21(m, 6H), 6.76(dd, 1H), 6.23(dd, 1H), 4.9(bs, 1H), 4.49(d, 2H), 3.08(m, 2H), 2.85(s, 3H).

EXAMPLE 2/3
4-[N'-Methyl-N'-(3,5-bistrifluoromethyl-benzoyl)-amino]-5-(4-chlorophenyl)-pent-2-enoic acid N-[2-ethoxycarbonyl-2-ethyl-butyl]-amide: amorphous white solid

EXAMPLE 2/4
4-[N'-Methyl-N'-(3,5-bistrifluoromethyl-benzoyl)-amino]-5-(4-chlorophenyl)-pent-2-enoic acid N-(3-methoxy-benzyl)-amide: amorphous white solid $R_f$ value=0.25 (hexane/ethyl acetate 1:1).

EXAMPLE 3
4-[N'-Methyl-N'-(3,5-bistrifluoromethyl-benzoyl)-amino]-5-(4-chlorophenyl)-pentanoic acid N-(2-methoxy-benzyl)-amide The title compound is obtained using the methodology described in Example 1 starting from 4-(N'-methyl)-amino-5-(4-chlorophenyl)-pentanoic acid N-(2-methoxy-benzyl)-amide. It is obtained in the form of a colourless amorphous solid. $^1$H-NMR, 400 MHz, DMSO, 150°, delta (ppm): 7.95(s, 1H), 7.50(s, 2H), 7.43(s, 1H), 7.3–7.1(m, 6H), 6.95 (d, 1H), 4.23(d, 2H), 3.80(s, 3H), 2.9–2.7(m, 5H), 2.25(m, 2H), 1.92(m, 2H).

The starting materials can be prepared as follows:

a) 4-(N'-Methyl)-amino-5-(4-chlorophenyl)-pentanoic acid N-(2-methoxy-benzyl)-amide The title compound is prepared in a manner analogous to that described in Example 1a) from 4-(N'-methyl-N'-tert-butyloxycarbonyl)-amino-5-(4-chlorophenyl)-pentanoic acid N-(2-methoxy-benzyl)-amide.

b) 4-(N'-Methyl-N'-tert-butyloxycarbonyl)-amino-5-(4-chlorophenyl)-pentanoic acid N-(2-methoxy-benzyl)-amide The title compound is prepared in a manner analogous to that described in Example 1b) from 4-(N'-methyl-N'-tert-butyloxycarbonyl)-amino-5-(4-chloro-phenyl)-pentanoic acid. $^1$H-NMR, 200 MHz, CDCl$_3$, delta (ppm): 7.25(m, 4H), 7.05(m, 2H), 6.87(m, 2H), 4.40(m, 2H), 3.82(s, 3H), 2.68 and 2.55(2s, 3H), 2.65(m, 2H), 2.2–1.7(m, 4H), 1.35 and 1.22(2s, 9H).

c) 4-(N'-Methyl-N'-tert-butyloxycarbonyl)-amino-5-(4-chlorophenyl)-pentanoic acid The title compound is prepared in a manner analogous to that described in Example 1c) from 4-(N'-methyl-N'-tert-butyloxycarbonyl)-amino-5-(4-chlorophenyl)-pentanoic acid ethyl ester. $^1$H-NMR, 400 MHz, DMSO, 120°, delta (ppm): 7.25(d, 2H), 7.15(d, 2H), 4.19(m, 1H), 2.70(2s, 2H), 2.58(s, 3H), 2.11(t, 2H), 1.72(m, 2H), 1.28(s, 9H).

d) 4-(N'-Methyl-N'-tert-butyloxycarbonyl)-amino-5-(4-chlorophenyl)-pentanoic acid ethyl ester A solution of 1.0 g of 4-(N'-methyl-N'-tert-butyloxycarbonyl)-amino-5-(4-chlorophenyl)-pent-2-enoic acid ethyl ester (see Example 1d) in 30 ml of tetrahydrofuran is hydrogenated for 0.5 hour in the presence of 0.1 g of palladium/activated carbon and 0.2 g of 1,2-dichlorobenzene. The reaction mixture is then filtered and concentrated by evaporation. In this way the title compound is obtained in pure form. $^1$H-NMR, 200 MHz, CDCl$_3$, delta (ppm): 7.25(d, 2H), 7.12(d, 2H), 4.12(q, 2H), 2.72(m, 2H), 2.68 and 2.60(2s, 3H), 2.26(d, 2H), 1.82(m, 2H), 1.35(m, 12H).

In the same manner as that described in Example 3, using the appropriate amines in Step 3b) it is also possible to prepare the following compounds [in the preparation of Example 3/3, 2-methylbenzenesulfonamide is used instead of an amine in Step 3/3b)]:

EXAMPLE 3/1
4-[N'-Methyl-N'-(3,5-bistrifluoromethyl-benzoyl)-amino]-5-(4-chlorophenyl)-pentanoic acid (4-phenyl4-acetylamino-piperidineamide)

$^1$H-NMR, 400 MHz, DMSO, 150°, delta (ppm): 7.98(s, 1H), 7.50(s, 2H), 7.41(s, 1H), 7.38(2s, 2H), 7.25(m, 4H), 7.12(m, 3H), 4.2(b, 1H), 3.15(t, 2H), 2.9(m, 2H), 2.80(s, 3H), 2.4(m, 4H), 2.05(m, 2H), 1.89(s,3H), 1.8(m, 2H).

EXAMPLE 3/2
4-[N'-Methyl-N'-(3,5-bistrifluoromethyl-benzoyl)-amino]-5-(4-chlorophenyl)-pentanoic acid N-benzyl-N-methyl-amide ¹H-NMR, 400 MHz, DMSO, 150°, delta (ppm): 7.98(s, 1H), 7.45(s, 2H), 7.25–7.05(m, 9H), 4.50(s, 2H), 2.9(m, 2H), 2.75(s, 3H), 2.41(m, 2H), 2.02 and 1.91(2m, 2H).

EXAMPLE 3/3
4-[N'-Methyl-N'-(3,5-bistrifluoromethyl-benzoyl)-amino]-5-(4-chlorophenyl)-pentanoic acid N-(2-methyl-phenylsulfon)-amide
¹H-NMR, 400 MHz, DMSO, 150°, delta (ppm): 7.99(s, 1H), 7.45(s, 2H), 7.25–7.08(m, 9H), 4.46(s, 2H), 2.9(m, 2H), 2.50(s, 3H), 2.3(m, 2H), 1.9 and 1.78(2m, 2H).

EXAMPLE 3/4
4-[N'-Methyl-N'-(3,5-bistrifluoromethyl-benzoyl)-amino]-5-(4-chlorophenyl)-pentanoic acid N-(4-quinolinyl)-amide
¹H-NMR, 400 MHz, DMSO, 150°, delta (ppm): 8.74(d, 1H), 8.24(d, 1H), 7.99(2d, 2H), 7.98(s, 1H), 7.71(t, 1H), 7.53(t, 2H), 7.54(s, 2H), 7.30 and 7.20(2d, 4H), 4.5(b, 1H), 2.9(m, 2H), 2.82(s, 3H), 2.65(m, 2H), 2.10(m, 2H).

EXAMPLE 3/5
4-[N'-Methyl-N'-(3,5-bistrifluoromethyl-benzoyl)-amino]-5-(4-chlorophenyl)-pentanoic acid N-(4-ethoxycarbonyl-phenyl)-amide: white crystals having a melting point of 159–160°

EXAMPLE 4
4-[N'-Methyl-N'-(3,5-bistrifluoromethyl-benzoyl)-amino]-5-(4-chlorophenyl)-pentanoic acid N-(2-methoxy-benzyl)-amide This is the compound of Example 3. It can be prepared also by the following synthesis method: a mixture of 0.495 g of 4-[N'-methyl-N'-(3,5-bistrifluoromethyl-benzoyl)-amino]-5-(4-chlorophenyl)-pentanoic acid, 0.137 g of 2-methoxy-benzylamine, 0.21 g of N-ethyl-N'-(3-dimethylaminopropyl)-carbodiimide hydrochloride, 0.134 g of 4-dimethylaminopyridine and 10 ml of methylene chloride is stirred at room temperature for 16 hours and then concentrated by evaporation. The residue is chromatographed (silica gel, hexane/ethyl acetate 1:1). In this way the title compound is obtained in the form of a colourless amorphous solid. ¹H-NMR, 400 MHz, DMSO, 150°, delta (ppm): 7.95(s, 1H), 7.50(s, 2H), 7.43(s, 1H), 7.3–7.1(m, 6H), 6.95(d, 1H), 4.23(d,2H), 3.80(s, 3H), 2.9–2.7(m, 5H), 2.25(m, 2H), 1.92(m, 2H).

The starting materials can be prepared as follows:
a) 4-[N'-Methyl-N'-(3,5-bistrifluoromethyl-benzoyl)-amino]-5-(4-chlorophenyl)-pentanoic acid A solution of 25 g of 4-[N'-methyl-N'-(3,5-bistrifluoromethyl-benzoyl)-amino]-5-(4-chloro-phenyl)-pentanoic acid ethyl ester and 18 g of lithium hydroxide monohydrate in 120 ml of THF/methanol/water 3:3:1 is stirred at room temperature for 4 hours and then 200 ml of water and 1N hydrochloric acid are added (pH value approx. 2). The mixture is extracted twice with ethyl acetate. The combined organic phases are washed with water and saturated NaCl solution, dried (magnesium sulfate) and concentrated by evaporation. The residue is recrystallised from diethyl ether/petroleum ether. In this way the title compound is obtained in the form of white crystals (m.p. 125–127°).
b) 4-[N'-Methyl-N'-(3,5-bistrifluoromethyl-benzoyl)-amino]-5-(4-chlorophenyl)-pentanoic acid ethyl ester A solution of 29 g of 4-[N'-methyl-N'-(3,5-bistrifluoromethyl-benzoyl)-amino]-5-(4-chlorophenyl)-pent-2-enoic acid ethyl ester [see example 2b)] in 300 ml of tetrahydrofuran is hydrogenated for 0.5 hour in the presence of 3 g of palladium/activated carbon (10%) and 6 g of 1,2-dichlorobenzene. The reaction mixture is then filtered and concentrated by evaporation. The residue is chromatographed (silica gel, hexane/ethyl acetate 3:1). In this way the title compound is obtained in the form of a colourless oil.
¹H-NMR, 500 MHz, DMSO, 140°, delta (ppm): 7.99(s, 1H), 7.51(s, 2H), 7.30(td, 2H), 7.18(d, 2H), 4.5(b, 1H), 4.06(q, 2H), 2.9(m, 1H), 2.8(m, 4H), 2.35(m, 2H), 2.02(m, 1H), 1.90(m, 1H), 1.19(t, 3H).

Analogously to Example 4, using the appropriate amines (instead of 2-methoxybenzylamine) it is also possible to obtain the following compound:

EXAMPLE 4/1
4-[N'-Methyl-N'-(3,5-bistrifluoromethyl-benzoyl)-amino]-5-(4-chlorophenyl)-pentanoic acid N-(1-methylindol-5-yl)-amide: amorphous white solid. ¹H-NMR, 500 MHz, DMSO, 140°, delta (ppm): 9.20(bs, 1H), 7.96(s, 1H), 7.73(s, 1H), 7.51(s, 2H), 7.3–7.15(m, 7H), 6.32(d, 1H), 3.73(s, 3H), 2.99–2.76(m, 5H), 2.40(m, 2H), 2.10(m, 1H), 1.99(m, 1H).

EXAMPLE 5
4-[N'-Methyl-N'-(3,5-bistrifluoromethyl-benzoyl)-amino]-5-(4-chlorophenyl)-pentanoic acid N-isopropyl-amide: 13.2 mg of triethylamine are added to a solution of 50 mg of 4-[N'-methyl-N'-(3,5-bistrifluoromethyl-benzoyl)-amino]-5-(4-chlorophenyl)-pentanoic acid hydroxysuccinimide ester and 5.6 mg of isopropylamine in 1.5 ml of methylene chloride. The reaction mixture is left to stand at room temperature for 18 hours. 0.5 ml of 1N potassium carbonate solution is then added and the mixture is shaken vigorously. After separation of the phases, the organic phase is separated off and concentrated by evaporation. In this way the title compound is obtained in the form of a white foam. $R_f$ value=0.36 (ethyl acetate).
(a) 4-[N'-Methyl-N'-(3,5-bistrifluoromethyl-benzoyl)-amino]-5-(4-chlorophenyl)-pentanoic acid hydroxysuccinimide ester A solution of 5 g of 4-[N'-methyl-N'-(3,5-bistrifluoromethyl-benzoyl)-amino]-5-(4-chlorophenyl)-pentanoic acid, 1.255 g of N-hydroxysuccinimide and 2.335 g of N,N'-dicyclohexylcarbodiimide in 250 ml of tetrahydrofuran is stirred at room temperature for 18 hours. The reaction solution is then filtered, taken up in ether, filtered again and concentrated by evaporation. In this way the title compound is obtained in the form of a colourless white foam.

In a manner analogous to that described in Example 5 it is also possible to prepare the following compounds:

EXAMPLE 5/1
4-[N'-Methyl-N'-(3,5-bistrifluoromethyl-benzoyl)-amino]-5-(4-chlorophenyl)-pentanoic acid N,N-dipropyl-amide: Rf value=0.29 (hexane:ethyl acetate 1:1)

EXAMPLE 5/2
4-[N'-Methyl-N'-(3,5-bistrifluoromethyl-benzoyl)-amino]-5-(4-chlorophenyl)-pentanoic acid N-allylamide: $R_f$ value=0.15 (hexane/ethyl acetate 1:1)

EXAMPLE 5/3
4-[N'-Methyl-N'-(3,5-bistrifluoromethyl-benzoyl)-amino]-5-(4-chlorophenyl)-pentanoic acid N-(2-N',N'-diethylamino-ethyl)-amide: $R_f$ value=0.1 (hexane/ethyl acetate 1:1)

EXAMPLE 5/4
4-[N'-Methyl-N'-(3,5-bistrifluoromethyl-benzoyl)-amino]-5-(4-chlorophenyl)-pentanoic acid N-(2-hydroxyethyl)-amide: $R_f$ value=0.11 (methylene chloride:methanol 95:5)

EXAMPLE 5/5
4-[N'-Methyl-N'-(3,5-bistrifluoromethyl-benzoyl)-amino]-5-(4-chlorophenyl)-pentanoic acid (piperidineamide): $R_f$ value=0.27 (methylene chloride:methanol 95:5)

EXAMPLE 5/6
4-[N'-Methyl-N'-(3,5-bistrifluoromethyl-benzoyl)-amino]-5-(4-chlorophenyl)-pentanoic acid N-methyl-N-(3-chlorobenzyl)-amide: $R_f$ value=0.8 (methylene chloride:methanol 95:5)

EXAMPLE 5/7
4-[N'-Methyl-N'-(3,5-bistrifluoromethyl-benzoyl)-amino]-5-(4-chlorophenyl)-pentanoic acid N-(2-chlorobenzyl)-amide: $R_f$ value=0.26 (methylene chloride:methanol 95:5)

EXAMPLE 5/8
4-[N'-Methyl-N'-(3,5-bistrifluoromethyl-benzoyl)-amino]-5-(4-chlorophenyl)-pentanoic acid (azocane-1-amide)

EXAMPLE 5/9
4-[N'-Methyl-N'-(3,5-bistrifluoromethyl-benzoyl)-amino]-5-(4-chlorophenyl)-pentanoic acid N-(1,1-dimethyl-2-hydroxy)-ethyl-amide: $R_f$ value=0.2 (methylene chloride:methanol 95:5)

EXAMPLE 5/10
4-[N'-Methyl-N'-(3,5-bistrifluoromethyl-benzoyl)-amino]-5-(4-chlorophenyl)-pentanoic acid N-(2-pyridylmethyl)-amide: $R_f$ value=0.15 (methylene chloride:methanol 95:5)

EXAMPLE 5/11
4-[N'-Methyl-N'-(3,5-bistrifluoromethyl-benzoyl)-amino]-5-(4-chlorophenyl)-pentanoic acid (4-dimethylamino-piperidineamide): $R_f$ value=0.05 (methylene chloride:methanol 95:5)

EXAMPLE 5/12
4-[N'-Methyl-N'-(3,5-bistrifluoromethyl-benzoyl)-amino]-5-(4-chlorophenyl)-pentanoic acid N-[3-(morpholin-4-yl)-propyl]-amide: $R_f$ value=0.05 (methylene chloride:methanol 95:5)

EXAMPLE 5/13
4-[N'-Methyl-N'-(3,5-bistrifluoromethyl-benzoyl)-amino]-5-(4-chlorophenyl)-pentanoic acid (4-phenyl-piperazine-1-amide): $R_f$ value=0.32 (ethyl acetate)

EXAMPLE 5/14
4-[N'-Methyl-N'-(3,5-bistrifluoromethyl-benzoyl)-amino]-5-(4-chlorophenyl)-pentanoic acid N-(3-diethylamino-propyl)-amide: $R_f$ value=0.05 (methylene chloride:methanol 95:5)

EXAMPLE 5/15
4-[N'-Methyl-N'-(3,5-bistrifluoromethyl-benzoyl)-amino]-5-(4-chlorophenyl)-pentanoic acid N-(3-methoxy-4-hydroxy-benzyl)-amide: $R_f$ value=0.27 (methylene chloride:methanol 95:5)

EXAMPLE 5/16
4-[N'-Methyl-N'-(3,5-bistrifluoromethyl-benzoyl)-amino]-5-(4-chlorophenyl)-pentanoic acid N-[2-(piperidin-1-yl)-ethyl]-amide: $R_f$ value=0.08 (methylene chloride:methanol 95:5)

EXAMPLE 5/17
4-[N'-Methyl-N'-(3,5-bistrifluoromethyl-benzoyl)-amino]-5-(4-chlorophenyl)-pentanoic acid N-(4-hydroxy-cyclohexyl)-amide: $R_f$ value=0.15 (methylene chloride:methanol 95:5)

EXAMPLE 5/18
4-[N'-Methyl-N'-(3,5-bistrifluoromethyl-benzoyl)-amino]-5-(4-chlorophenyl)-pentanoic acid N-methyl-N-(2-hydroxyethyl)-amide: $R_f$ value=0.4 (ethyl acetate:methanol 5:1)

EXAMPLE 5/19
4-[N'-Methyl-N'-(3,5-bistrifluoromethyl-benzoyl)-amino]-5-(4-chlorophenyl)-pentanoic acid N-(2-hydroxyethyl)-N-(1-methyl-2-hydroxy-ethyl)-amide: $R_f$ value=0.35 (ethyl acetate:methanol 5:1)

EXAMPLE 5/20
4-[N'-Methyl-N'-(3,5-bistrifluoromethyl-benzoyl)-amino]-5-(4-chlorophenyl)-pentanoic acid N-[2-(3,4-dihydroxyphenyl)-ethyl]-amide: $R_f$ value=0.25 (ethyl acetate)

EXAMPLE 5/21
4-[N'-Methyl-N'-(3,5-bistrifluoromethyl-benzoyl)-amino]-5-(4-chlorophenyl)-pentanoic acid {4-[2-(4-chlorophenyl)-ethyl]-piperazine-1-amide}: $R_f$ value=0.3 (methylene chloride:methanol 95:5)

EXAMPLE 5/22
4-[N'-Methyl-N'-(3,5-bistrifluoromethyl-benzoyl)-amino]-5-(4-chlorophenyl)-pentanoic acid N-[2-(2-pyridyl)-ethyl]-amide: $R_f$ value=0.21 (ethyl acetate:methanol 95:5)

EXAMPLE 5/23
4-[N'-Methyl-N'-(3,5-bistrifluoromethyl-benzoyl)-amino]-5-(4-chlorophenyl)-pentanoic acid N-(3-methoxybenzyl)-amide: $R_f$ value=0.25 (hexane/ethyl acetate 1:1)

The reaction of anilines with 4-[N'-methyl-N'-(3,5-bistrifluoromethyl-benzoyl)-amino]-5-(4-chlorophenyl)-pentanoic acid to form the corresponding amides is carried out, for example, in the presence of propanephosphonic acid anhydride.

EXAMPLE 6
4-[N'-Methyl-N'-(3,5-bistrifluoromethyl-benzoyl)-amino]-5-(4-chlorophenyl)-pentanoic acid N-(4-isopropylphenyl)-amide A mixture consisting of 41.6 mg of 4-[N'-methyl-N'-(3,5-bistrifluoromethyl-benzoyl)-amino]-5-(4-chlorophenyl)-pentanoic acid, 12.8 mg of 4-isopropylaniline, 36.65 mg of propanephosphonic acid anhydride, 37 mg of triethylamine and 1.5 ml of methylene chloride is left to stand at room temperature for 18 hours. 0.5 ml of 1N potassium carbonate solution is then added and the mixture is shaken vigorously. After separation of the phases, the organic phase is separated off and concentrated by evaporation. In this way the title compound is obtained in the form of a white foam. $R_f$ value=0.26 (ethyl acetate)

In a manner analogous to that described in Example 6 it is also possible to prepare the following compounds:

EXAMPLE 6/1
4-[N'-Methyl-N'-(3,5-bistrifluoromethyl-benzoyl)-amino]-5-(4-chlorophenyl)-pentanoic acid N-ethyl-N-phenyl-amide: $R_f$ value=0.66 (methylene chloride:methanol 95:5)

EXAMPLE 6/2
4-[N'-Methyl-N'-(3,5-bistrifluoromethyl-benzoyl)-amino]-5-(4-chlorophenyl)-pentanoic acid N-(3-methoxyphenyl)-amide: $R_f$ value=0.76 (methylene chloride:methanol 95:5)

EXAMPLE 6/3
4-[N'-Methyl-N'-(3,5-bistrifluoromethyl-benzoyl)-amino]-5-(4-chlorophenyl)-pentanoic acid N-(3-nitrophenyl)-amide: $R_f$ value=0.66 (methylene chloride:methanol 95:5)

EXAMPLE 6/4
4-[N'-Methyl-N'-(3,5-bistrifluoromethyl-benzoyl)-amino]-5-(4-chlorophenyl)-pentanoic acid N-(2-methoxy-4-nitrophenyl)-amide: $R_f$ value=0.60 (methylene chloride:methanol 95:5)

EXAMPLE 6/5
4-[N'-Methyl-N'-(3,5-bistrifluoromethyl-benzoyl)-amino]-5-(4-chlorophenyl)-pentanoic acid (3-acetyl-indole-1-amide) $R_f$ value=0.40 (ethyl acetate)

EXAMPLE 6/6
4-[N'-Methyl-N'-(3,5-bistrifluoromethyl-benzoyl)-amino]-5-(4-chlorophenyl)-pentanoic acid N-(3-bromophenyl)-amide: $R_f$ value=0.58 (ethyl acetate)

EXAMPLE 7
3-[N'-(3,5-Bistrifluoromethyl-benzoyl)-N'-methyl-amino]-4-(1H-indol-3-yl)-butanoic acid N-cyclohexyl-N-isopropyl-amide N-cyclohexyl-isopropylamine (10.4 mg, 1.2 eq) and triethylamine (10.4 µl, 1.2 eq) are dissolved in dichloromethane (1 ml), and the hydroxysuccinimide ester of Example 7(c) (35 mg, 0.06 mmol) is added. The solution is left to stand at room temperature for 2 days. The solution is then washed with 1N potassium carbonate solution (0.5 ml) and the solvent is concentrated by evaporation. $R_f$ (ethyl acetate/methanol 1:1)=0.68.

The reaction of (1H-indol-3-yl)-acetic acid to form 4-(1H-indol-3-yl)-3-methylamino-butanoic acid ethyl ester is described in Example 14(a) and (b).

(a) 3-[N'-(3,5-Bistrifluoromethyl-benzoyl)-N'-methyl-amino]-4-(1H-indol-3-yl)-butanoic acid ethyl ester)

4-(1H-indol-3-yl)-3-methylamino-butanoic acid ethyl ester (24.2 g, 93 mmol) is placed in dichloromethane in an ice bath, and 3,5-bistrifluoromethyl-benzoyl chloride (16.7 ml, 1.0 eq) is added. The mixture is stirred at room temperature for 2 hours and then 1N hydrochloric acid is added; the mixture is extracted with dichloromethane, dried over magnesium sulfate and concentrated by evaporation. Crystallisation of the residue from hexane yields the title compound in the form of light-beige crystals, $R_f$ (ethyl acetate/hexane 1/2)=0.56.

(b) 3-[N'-(3,5-Bistrifluoromethyl-benzoyl)-N'-methyl-amino]-4-(1H-indol-3-yl)-butanoic acid The ester of Example 7(a) (48.2 g, 96 mmol) is placed in tetrahydrofuran (600 ml) and water (440 ml), and 3M lithium hydroxide solution (160 ml, 5 eq) is added. The mixture is stirred at room temperature for 17 hours. 1N hydrochloric acid is then added and extraction is carried out with ethyl acetate. Drying over magnesium sulfate and concentration by evaporation yield the title compound in the form of a light-brown solid foam, $R_f$ (ethyl acetate)=0.64.

(c) 3-[N'-(3,5-Bistrifluoromethyl-benzoyl)-N'-methyl-amino]-4-(1H-indol-3-yl)-butanoic acid (N-hydroxysuccinimide) ester The acid of Example 7(b) (45 g, 95 mmol), N,N-dimethyl-aminopyridine (2.33 g, 0.2 eq) and N-(3-dimethylaminopropyl)-N'-ethylcarbodiimide hydrochloride (20.1 g, 1.1 eq) are placed in dichloromethane, and in an ice bath N-hydroxy-succinimide (11.9 g, 1.05 eq) is added. The mixture is stirred at room temperature over-night. The reaction mixture is poured into 5% citric acid/ice. Extraction with dichloromethane, drying over magnesium sulfate and concentration by evaporation yield a yellow oil which is chromatographed on silica gel with hexane/ethyl acetate 1/9. The title compound is obtained in the form of a solid foam, $R_f$ (ethyl acetate)=0.54.

The following are prepared analogously to Example 7:

EXAMPLE 7/1
3-[N'-(3,5-Bistrifluoromethyl-benzoyl)-N'-methyl-amino]-4-(1H-indol-3-yl)-butanoic acid [2-(2-hydroxyethyl)-piperidineamide]: $R_f$ (ethyl acetate)=0.50

EXAMPLE 7/2
3-[N'-(3,5-Bistrifluoromethyl-benzoyl)-N'-methyl-amino]-4-(1H-indol-3-yl)-butanoic acid N-(carbamoylmethyl)-amide; $R_f$ (ethyl acetate/methanol 1:1)=0.73

EXAMPLE 7/3
3-[N'-(3,5-Bistrifluoromethyl-benzoyl)-N'-methyl-amino]-4-(1H-indol-3-yl)-butanoic acid N-[3-(morpholin-4-yl)-propyl]-amide; $R_f$ (ethyl acetate/methanol 1:1)=0.06

EXAMPLE 7/4
3-[N'-(3,5-Bistrifluoromethyl-benzoyl)-N'-methyl-amino]-4-(1H-indol-3-yl)-butanoic acid (4-dimethylamino-piperidineamide): $R_f$ (ethyl acetate)=0.02

EXAMPLE 7/5
3-[N'-(3,5-Bistrifluoromethyl-benzoyl)-N'-methyl-amino]-4-(1H-indol-3-yl)-butanoic acid [4-(2-methoxy-phenyl)-piperazineamide]: $R_f$ (ethyl acetate)=0.39

EXAMPLE 7/6
3-[N'-(3,5-Bistrifluoromethyl-benzoyl)-N'-methyl-amino]-4-(1H-indol-3-yl)-butanoic acid (2-methyl-aziridineamide): $R_f$ (ethyl acetate)=0.71

EXAMPLE 7/7
3-[N'-(3,5-Bistrifluoromethyl-benzoyl)-N'-methyl-amino]-4-(1H-indol-3-yl)-butanoic acid N-(1-phenyl-ethyl)-amide; $R_f$ (ethyl acetate/methanol 1:1)=0.86

EXAMPLE 8
3-[N'-(3,5-Bistrifluoromethyl-benzoyl)-N'-methyl-amino]-4-(1H-indol-3-yl)-butanoic acid N-phenyl-amide Aniline (8.3 mg, 1.2 eq) is placed in dichloromethane (0.5 ml), and triethylamine (52 µl, 5 eq) and 3-[N'-(3,5-bistrifluoromethyl-benzoyl)-N'-methyl-amino]-4-(1H-indol-3-yl)-butanoic acid [Example 7(b)] (35 mg, 0.07 mmol) are added. Propanephosphonic acid anhydride (31.6 mg, 4 eq, in 0.5 ml of ethyl acetate/dichloromethane) is added and the mixture is left to stand at room temperature for 24 hours. The mixture is washed with 1N potassium carbonate solution (0.5 ml) and the solvent is concentrated by evaporation. The resulting title compound has an $R_f$ value (ethyl acetate) of 0.69.

The following are prepared analogously to Example 8:

EXAMPLE 8/1
3-[N'-(3,5-Bistrifluoromethyl-benzoyl)-N'-methyl-amino]-4-(1H-indol-3-yl)-butanoic acid N-ethyl-N-phenyl-amide; $R_f$ (ethyl acetate)=0.58

EXAMPLE 8/2
3-[N'-(3,5-Bistrifluoromethyl-benzoyl)-N'-methyl-amino]-4-(1H-indol-3-yl)-butanoic acid N-(2-hydroxy-phenyl)-amide; $R_f$ (ethyl acetate)=0.41

EXAMPLE 9
3-[N'-(3,5-Bistrifluoromethyl-benzoyl)-N'-methyl-amino]-4-(4-chlorophenyl)-butanoic acid N-cyclohexyl-N-isopropyl-amide N-cyclohexyl-isopropylamine (10.5 mg, 1.2 eq) and triethylamine (10.4 μl, 1.2 eq) are dissolved in dichloromethane (1 ml), and the hydroxysuccinimide ester of Example 9(e) (35 mg, 0.06 mmol) is added. The solution is left to stand at room temperature for 2 days. The mixture is then washed with 1N potassium carbonate solution (0.5 ml) and the solvent is concentrated by evaporation. $R_f$ (ethyl acetate/methanol 1:1)=0.64

(a) 4-(4-Chlorophenyl)-3-oxo-butanoic acid ethyl ester:

4-Chlorophenylacetic acid (34.1 g, 0.2 mol) is dissolved in tetrahydrofuran (260 ml) In an ice bath, carbonyldiimidazole (38.8 g, 1.1 eq) is added, followed by a further 100 ml of tetrahydrofuran. The white suspension is stirred at 0° C. for 2 hours. The mixture is allowed to rise to room temperature and bis-(malonic acid monoethyl ester) magnesium salt (68.6 g, 1.15 eq) is added. The mixture is stirred at room temperature overnight, then some of the solvent is concentrated by evaporation; 6N hydrochloric acid and diethyl ether are added. The organic phase is washed with bicarbonate solution and brine, dried over magnesium sulfate and concentrated by evaporation. The title compound is obtained in the form of a yellow oil, $R_f$ (dichloromethane/methanol 19:1)=0.83.

(b) 4-(4-Chlorophenyl)-3-methylamino-butanoic acid ethyl ester

The keto ester of Example 9(a) is placed in dichloromethane (345 ml), and methylamine (27% in ethanol, 71 ml, 5 eq), magnesium sulfate anhydrous (121 g, 8 eq) and glacial acetic acid (1.5 ml) are added. The reaction mixture is stirred at 40° C. for 3 days, then filtered and the residue is washed with dichloromethane, and the combined filtrates are concentrated by evaporation. The residue is dissolved in methanol (150 ml), and sodium acetate/glacial acetic acid buffer (100 ml, 1M in methanol) is added. Sodium cyanoborohydride (85%, 10.2 g, 1.1 eq) is added and the mixture is stirred at room temperature for 2 hours. After the addition of 1N hydrochloric acid (450 ml) the reaction mixture is concentrated and then diethyl ether is added. Extraction is carried out with 1N hydrochloric acid. The acidic aqueous phase is rendered basic with potassium hydroxide and extracted with ethyl acetate. The title compound is obtained in the form of a yellow oil, $R_f$ (ethyl acetate)=0.1.

(c) 3-[N'-(3,5-Bistrifluoromethyl-benzoyl)-N'-methyl-amino]-4-(4-chlorophenyl)-butanoic acid ethyl ester The amine of Example 9(b) (23.8 g, 93 mmol) is placed in dichloromethane in an ice bath, and bis-trifluorobenzoyl chloride (16.8 ml, 1.0 eq) is added. The mixture is stirred at room temperature for 2 hours, and then 1N hydrochloric acid is added. The mixture is extracted with dichloromethane, dried over magnesium sulfate and concentrated by evaporation. The title compound is obtained in the form of a yellow oil which is reacted further in crude form. $R_f$ (ethyl acetate/hexane 1/2)=0.59.

(d) 3-[N'-(3,5-Bistrifluoromethyl-benzoyl)-N'-methyl-amino]-4-(4-chlorophenyl)-butanoic acid The ester of Example 9(c) (52.2 g, 0.1 mol) is placed in tetrahydrofuran (600 ml) and water (430 ml), and 3M lithium hydroxide solution (176 ml, 5 eq) is added. The mixture is stirred at room temperature overnight. 1N hydrochloric acid is then added and extraction is carried out with ethyl acetate. Drying over magnesium sulfate and concentration by evaporation yield the title compound in the form of a light-yellow solid foam, $R_f$ (ethyl acetate)=0.18.

(e) 3-[N'-(3,5-Bistrifluoromethyl-benzoyl)-N'-methyl-amino]-4-(4-chlorophenyl)-butanoic acid(N-hydroxysuccinimide)ester The acid of Example 9(d) (49 g, 105 mmol), N,N-dimethylaminopyridine (2.56 g, 0.2 eq) and N-(3-dimethylaminopropyl)-N'-ethylcarbodiimide hydrochloride (22.8 g, 1.1 eq) are placed in dichloromethane, and in an ice bath N-hydroxysuccinimide (13.1 g, 1.05 eq) is added. The mixture is stirred at room temperature overnight. The reaction mixture is poured into 5% citric acid/ice. Extraction with dichloromethane, drying over magnesium sulfate and concentration by evaporation yield a yellow oil which is chromatographed on silica gel with hexane/ethyl acetate 1/9. The title compound is obtained in the form of a solid foam, $R_f$ (ethyl acetate)=0.62.

The following are prepared analogously to Example 9:

EXAMPLE 9/1

3-[N'-(3,5-Bistrifluoromethyl-benzoyl)-N'-methyl-amino]-4-(4-chlorophenyl)-butanoic acid [2-(2-hydroxyethyl)-piperidineamide]; $R_f$ (ethyl acetate)=0.06

EXAMPLE 9/2

3-[N'-(3,5-Bistrifluoromethyl-benzoyl)-N'-methyl-amino]-4-(4-chlorophenyl)-butanoic acid N-(carbamoylmethyl)-amide; $R_f$ (ethyl acetate/methanol 1:1)=0.67

EXAMPLE 9/3

3-[N'-(3,5-Bistrifluoromethyl-benzoyl)-N'-methyl-amino]-4-(4-chlorophenyl)-butanoic acid N-[3-(morpholin-4-yl)-propyl]-amide; $R_f$ (ethyl acetate/methanol 1:1)=0.01

EXAMPLE 9/4

3-[N'-(3,5-Bistrifluoromethyl-benzoyl)-N'-methyl-amino]-4-(4-chlorophenyl)-butanoic acid [4-(2-methoxy-phenyl)-piperazineamide]; $R_f$ (ethyl acetate)=0.13

EXAMPLE 9/5

3-[N'-(3,5-Bistrifluoromethyl-benzoyl)-N'-methyl-amino]-4-(4-chlorophenyl)-butanoic acid(2-methyl-aziridineamide); $R_f$ (ethyl acetate)=0.62

EXAMPLE 9/6

3-[N'-(3,5-Bistrifluoromethyl-benzoyl)-N'-methyl-amino]-4-(4-chlorophenyl)-butanoic acid N-(1-phenyl-ethyl)-amide; $R_f$ (ethyl acetate/methanol 1:1)=0.86

EXAMPLE 10

3-[N'-(3,5-Bistrifluoromethyl-benzoyl)-N'-methyl-amino]-4-(4-chlorophenyl)-butanoic acid N-phenyl-amide Aniline (8.4 mg, 1.2 eq) is placed in dichloromethane (0.5 ml), and triethylamine (52 μl, 5 eq) and the acid of Example 9(d) (35 mg, 0.07 mmol) are added. Propanephosphonic acid anhydride (31.6 mg, 4 eq, in 0.5 ml of ethyl acetate/dichloromethane) is added and the mixture is left to stand at room temperature for 24 hours. The mixture is washed with 1N potassium carbonate solution (0.5 ml) and the solvent is concentrated by evaporation. $R_f$ (ethyl acetate)=0.52.

The following are prepared analogously to Example 10:

EXAMPLE 10/1

3-[N'-(3,5-Bistrifluoromethyl-benzoyl)-N'-methyl-amino]-4-(4-chlorophenyl)-butanoic acid N-ethyl-N-phenyl-amide: $R_f$ (ethyl acetate)=0.62

EXAMPLE 10/2

3-[N'-(3,5-Bistrifluoromethyl-benzoyl)-N'-methyl-amino]-4-(4-chlorophenyl)-butanoic acid N-(2-hydroxy-phenyl)-amide: $R_f$ (ethyl acetate)=0.57

EXAMPLE 11

3-[N'-(3,5-Bistrifluoromethyl-benzoyl)-N'-methyl-amino]-4-(2-naphthyl)-butanoic acid N-benzyl-N-methylamide A solution of 0.01 ml (0.0724 mmol) of triethylamine in 0.4 ml of methylene chloride and a solution of 35 mg (0.0603 mmol) of 3-[N'-(3,5-bistrifluoromethyl-benzoyl)-N'-methyl-amino]-4-(2-naphthyl)-butanoic acid N-hydroxysuccinimide ester in 0.5 ml of methylene chloride are added in succession to 8.8 mg (0.0724 mmol) of benzylmethylamine and the mixture is left to stand at room temperature for 16 hours. The reaction mixture is then washed with 0.5 ml of a 1N aqueous potassium carbonate solution. The aqueous phase is extracted with 1.1 ml of methylene chloride. The combined organic phases are concentrated by evaporation in a vacuum centrifuge. The title compound is obtained in the form of a white foam. TLC: methylene chloride/acetone (7:3) $R_f$=0.48.

The starting compounds are prepared as follows:

a) 3-Oxo-4-(2-naphthyl)-butanoic acid ethyl ester 16.8 g (103 mmol) of carbonyldiimidazole are added in one portion at 0° C. to a solution of 17.5 g (94 mmol) of naphthylacetic acid in 180 ml of tetrahydrofuran. With foaming, a thick white suspension is formed. After 2 hours the reaction mixture is heated to room temperature and 32.2 g (108 mmol) of magnesium bis(monoethyl malonate) (D. W. Brooks, L. D.-L. Lu & S. Masamune; Angew. Chem. 91, 76 (1979)) are added. After 18 hours' stirring at room temperature, 150 ml of ice-cold 6N hydrochloric acid are added; ether is added and the organic phase is separated off. The organic phase is washed with saturated aqueous sodium hydrogen carbonate solution and with brine. The title compound is obtained in the form of a slightly yellow oil.

b) 3-Methylamino-4-(2-naphthyl)-but-2-enoic acid ethyl ester 52 ml (462 mmol) of a 27.3% solution of methylamine in ethanol, 100 g of magnesium sulfate and 1 ml of acetic acid are added to a solution of 23.7 g (92.5 mmol) of 3-oxo-4-naphthylbutanoic acid ethyl ester in 250 ml of methylene chloride and the mixture is stirred at 40° C. for 18 hours. The mixture is then filtered and the filter residue is washed with 1.5 liters of methylene chloride/ethanol (95:5). The title compound is obtained in the form of a crude product. $^1$H-NMR, 200 MHz, CDCl$_3$ (E/Z or Z/E mixture 1:3), delta, (ppm): 8.6 (b, 1H), 7.9–7.3 (m, 7H), 4.53, 4.42 (2s, 1H), 4.17, 4.11 (2q, 2H), 3.7 (s, 2H), 2.83, 2.68 (2d, 3H), 1.27 (t, 3H).

c) 3-Methylamino-4-(2-naphthyl)-butanoic acid ethyl ester 2 ml (17.6 mmol) of a 27.3% solution of methylamine in ethanol and 5.5 ml of acetic acid are added to 24.9 g (92.5 mmol) of 3-methylamino-4-(2-naphthyl)-but-2-enoic acid ethyl ester in 250 ml of ethanol and the mixture is cooled to 0° C. 6.4 g (87 mmol) of 85% sodium cyanoborohydride and a further 5.5 ml of acetic acid are added to the suspension. The reaction mixture is allowed to rise to room temperature, with stirring, over a period of 2 hours. A further 0.64 g (8.7 mmol) of sodium cyanoborohydride is added to the clear solution and stirring is continued at room temperature for a further 2 hours. 400 ml of 1N hydrochloric acid are then added and the reaction mixture is stirred for 1 hour and then the ethanol is evaporated off in a rotary evaporator. The aqueous phase is washed twice with ether and the ether phases are extracted with 1N hydrochloric acid. Ethyl acetate is added to the combined aqueous phases and the mixture is rendered basic with solid potassium carbonate; the organic phase is separated off and washed with brine. The title compound is obtained in the form of a slightly brown oil. IR: 1725 cm$^{-1}$; $^1$H-NMR, 200 MHz, CDCl$_3$, delta, (ppm): 7.86–7.32 (m, 7H), 4.12 (q, 2H), 3.26 (quint., 1H), 3.05–2.82 (ABxd, 2H), 2.53–2.44 (s, 3H), 1.25 (t, 3H).

d) 3-[N'-(3,5-Bistrifluoromethyl-benzoyl)-N'-methyl-amino]-4-(2-naphthyl)-butanoic acid 25.3 g (91.4 mmol) of 3,5-bistrifluoromethyl-benzoyl chloride followed by 13.3 ml (95.6 mmol) of triethylamine are added dropwise over a period of 5 minutes to a solution of 22.5 g (83.1 mmol) of 3-methylamino-4-(2-naphthyl)-butanoic acid ethyl ester in 500 ml of tert-butyl methyl ether. After 12 hours at room temperature, 16.6 g (415 mmol) of sodium hydroxide dissolved in 150 ml of methanol are added over a period of 10 minutes and the mixture is stirred for 5 hours. Then, at 0° C., 275 ml of 2N hydrochloric acid are added and the mixture is washed with 300 ml of ethyl acetate. After concentration in a rotary evaporator, the title compound crystallises out from tert-butyl methyl ether/hexane in the form of white needles. M.p.: 128–130° C.; IR: 3400–2500 (b), 1710, 1635 cm$^1$; $^1$H-NMR, 200 MHz, CDCl$_3$, delta, (ppm): 7.9–6.93 (m, 10H), 5.01, 4.30 (2m, rotamer, 1H), 3.9–2.6 (m, 4H), 3.18, 2.68 (2s, rotamer, 3H).

e) 3-[N'-(3,5-Bistrifluoromethyl-benzoyl)-N'-methyl-amino]-4-(2-naphthyl)-butanoic acid N-hydroxysuccinimide ester 3.75 g (32.6 mmol) of N-hydroxysuccinimide and 0.76 g (6.2 mmol) of 4-dimethylaminopyridine are added to a solution of 15 g (31 mmol) of 3-[N'-(3,5bistrifluoromethyl-benzoyl)-N'-methyl-amino]-4-(2-naphthyl)-butanoic acid in 100 ml of methylene chloride and the mixture is cooled to 0° C. 6.54 g (34.1 mmol) of N-ethyl-N'-(3-dimethylaminopropyl)-carbodiimide hydrochloride are then added and the reaction mixture is stirred at 0° C. for 10 minutes and then at room temperature for 3.5 hours. The mixture is washed with 5% citric acid, dried over sodium sulfate and concentrated by evaporation in a rotary evaporator. The title compound crystallises out from diethyl ether in the form of white crystals. M.p.: 131° C.; FD-MS: M$^+$=580; $^1$H-NMR, 200 MHz, CDCl$_3$, delta, (ppm): 7.9–6.95 (m, 10H), 4.89, 4.36 (2m, rotamer, 1H), 3.6–2.7 (m, 8H), 2.84, 2.69 (2s, rotamer, 3H).

EXAMPLE 12

3-[N'-(3,5-Bistrifluoromethyl-benzoyl)-N'-methyl-amino]-4-(2-naphthyl)-butanoic acid N-(4-chloro-2-methyl-phenyl)-amide A solution of 0.055 ml (0.393 mmol) of triethylamine and 38 mg (0.0786 mmol) of 3-[N'-(3,5-bistrifluoromethyl-benzoyl)-N'-methyl-amino]-4-(2-naphthyl)-butanoic acid in 0.5 ml of methylene chloride and a solution of 33.3 mg of 1-propanephosphonic acid anhydride in 0.4 ml of methylene chloride are added in succession to 10.3 mg (0.0943 mmol) of 4-chloro-2-methylaniline and the mixture is left to stand at room temperature overnight (>16 hours). The reaction mixture is then washed with 0.5 ml of a 1N aqueous potassium carbonate solution. The aqueous phase is extracted with a further 0.8 ml of methylene chloride. The combined organic phases are concentrated by evaporation in a vacuum centrifuge. The title compound is obtained in the form of a white foam. TLC: methylene chloride/acetone (7:3) $R_f$=0.48.

EXAMPLE 13

In a manner analogous to Examples 11 and 12 the following compounds are also prepared

EXAMPLE 13/1

3-[N'-(3,5-Bistrifluoromethyl-benzoyl)-N'-methyl-amino]-4-(2-naphthyl)-butanoic acid(azocane-1-amide); TLC: ethyl acetate/hexane (1:1) $R_f$=0.37

EXAMPLE 13/2

3-[N'-(3,5-Bistrifluoromethyl-benzoyl)-N'-methyl-amino]-4-(2-naphthyl)-butanoic acid(4,4-dihydroxy-piperidineamide); TLC: ethyl acetate/hexane (1:1) $R_f$=0.06

EXAMPLE 13/3
3-[N'-(3,5-Bistrifluoromethyl-benzoyl)-N'-methyl-amino]-4-(2-naphthyl)-butanoic acid N-(carbamoylmethyl)-amide; TLC: ethyl acetate/acetone (1:1) $R_f$=0.11

EXAMPLE 13/4
3-[N'-(3,5-Bistrifluoromethyl-benzoyl)-N'-methyl-amino]-4-(2-naphthyl)-butanoic acid N-(3-chlorobenzyl)-amide; TLC: ethyl acetate/hexane (1:1) $R_f$=0.30

EXAMPLE 13/5
3-[N'-(3,5-Bistrifluoromethyl-benzoyl)-N'-methyl-amino]-4-(2-naphthyl)-butanoic acid(2-methyl-piperidineamide); TLC: ethyl acetate/hexane (1:1) $R_f$=0.32

EXAMPLE 13/6
3-[N'-(3,5-Bistrifluoromethyl-benzoyl)-N'-methyl-amino]-4-(2-naphthyl)-butanoic acid N-(2-phenyl-2-hydroxyethyl)-amide; TLC: ethyl acetate/hexane (1:1) $R_f$=0.10

EXAMPLE 13/7
3-[N'-(3,5-Bistrifluoromethyl-benzoyl)-N'-methyl-amino]-4-(2-naphthyl)-butanoic acid N,N-bis(2-hydroxyethyl)-amide; TLC: ethyl acetate/acetone (1:1) $R_f$=0.48

EXAMPLE 13/8
3-[N'-(3,5-Bistrifluoromethyl-benzoyl)-N'-methyl-amino]-4-(2-naphthyl)-butanoic acid N-benzyl-N-isopropyl-amide; TLC: ethyl acetate/acetone (1:1) $R_f$=0.26

EXAMPLE 13/9
3-[N'-(3,5-Bistrifluoromethyl-benzoyl)-N'-methyl-amino]-4-(2-naphthyl)-butanoic acid(2-methyl-aziridineamide); TLC: ethyl acetate/hexane (1:1) $R_f$=0.35

EXAMPLE 13/10
3-[N'-(3,5-Bistrifluoromethyl-benzoyl)-N'-methyl-amino]-4-(2-naphthyl)-butanoic acid(4-methyl-piperidineamide); TLC: ethyl acetate/hexane (1:1) $R_f$=0.38

EXAMPLE 13/11
3-[N'-(3,5-Bistrifluoromethyl-benzoyl)-N'-methyl-amino]-4-(2-naphthyl)-butanoic acid N-[2-(3,4-dihydroxyphenyl)-ethyl]-amide; TLC: ethyl acetate/acetone (1:1) $R_f$=0.59

EXAMPLE 13/12
3-[N'-(3,5-Bistrifluoromethyl-benzoyl)-N'-methyl-amino]-4-(2-naphthyl)-butanoic acid N-(2,5-dimethoxy-4-nitro-phenyl)-amide

EXAMPLE 13/13
3-[N'-(3,5-Bistrifluoromethyl-benzoyl)-N'-methyl-amino]-4-(2-naphthyl)-butanoic acid N-(4-methyl-pyrimidin-2-yl)-amide; TLC: ethyl acetate/hexane (1:1) $R_f$=0.30

EXAMPLE 13/14
3-[N'-(3,5-Bistrifluoromethyl-benzoyl)-N'-methyl-amino]-4-(2-naphthyl)-butanoic acid(2-methylmercapto-benzimidazol-1-yl-amide); TLC: ethyl acetate/hexane (1:1) $R_f$=0.67

EXAMPLE 13/15
3-[N'-(3,5-Bistrifluoromethyl-benzoyl)-N'-methyl-amino]-4-(2-naphthyl)-butanoic acid(2-cyanomethyl-benzimidazol-1-yl-amide); TLC: ethyl acetate/acetone (1:1) $R_f$=0.74

EXAMPLE 13/16
3-[N'-(3,5-Bistrifluoromethyl-benzoyl)-N'-methyl-amino]-4-(2-naphthyl)-butanoic acid N-(4-chloro-6-methyl-pyrimidin-2-yl)-amide; TLC: ethyl acetate/acetone (1:1) $R_f$=0.77

EXAMPLE 13/17
3-[N'-(3,5-Bistrifluoromethyl-benzoyl)-N'-methyl-amino]-4-(2-naphthyl)-butanoic acid N-(2-ethyl-phenyl)-amide; TLC: ethyl acetate/hexane (1:1) $R_f$=0.33

EXAMPLE 13/18
3-[N'-(3,5-Bistrifluoromethyl-benzoyl)-N'-methyl-amino]-4-(2-naphthyl)-butanoic acid N-(2,4-dihydroxy-phenyl)-amide; TLC: ethyl acetate/acetone (1:1) $R_f$=0.80

EXAMPLE 13/19
3-[N'-(3,5-Bistrifluoromethyl-benzoyl)-N'-methyl-amino]-4-(2-naphthyl)-butanoic acid N-(4-diethylamino-phenyl)-amide; TLC: ethyl acetate/hexane (1:1) $R_f$=0.25

EXAMPLE 13/20
3-[N'-(3,5-Bistrifluoromethyl-benzoyl)-N'-methyl-amino]-4-(2-naphthyl)-butanoic acid(2-methyl-indol-1-yl-amide); TLC: ethyl acetate/hexane (1:1) $R_f$=0.89

EXAMPLE 13/21
3-[N'-(3,5-Bistrifluoromethyl-benzoyl)-N'-methyl-amino]-4-(2-naphthyl)-butanoic acid N-(2-chloro-5-nitro-phenyl)-amide; TLC: ethyl acetate/hexane (1:1) $R_f$=0.22

EXAMPLE 13/22
3-[N'-(3,5-Bistrifluoromethyl-benzoyl)-N'-methyl-amino]-4-(2-naphthyl)-butanoic acid N-(pyrazin-2-yl)-amide; TLC: ethyl acetate/hexane (1:1) $R_f$=0.41

EXAMPLE 13/23
3-[N'-(3,5-Bistrifluoromethyl-benzoyl)-N'-methyl-amino]-4-(2-naphthyl)-butanoic acid N-(4-dimethylamino-phenyl)-amide; TLC: ethyl acetate/hexane (1:1) $R_f$=0.16

EXAMPLE 14
5-[N'-(3,5-Bistrifluoromethyl-benzoyl)-N'-methyl-amino]-6-(1H-indol-3-yl)-hexanoic acid [4-(4-methoxy-phenyl)-piperazineamide]

80 mg (0.134 mmol) of 5-[N'-(3,5-bistrifluoromethyl-benzoyl)-N'-methyl-amino]-6-(1H-indol-3-yl)-hexanoic acid N-hydroxysuccinimidyl ester are dissolved in 5 ml of methylene chloride, and 68 ml (0.48 mmol) of triethylamine and 42.5 mg (0.16 mmol) of 1-(4-methoxyphenyl)-piperazine dihydrochloride are added in succession. The reaction mixture is stirred at room temperature for 20 hours, then washed twice with aqueous potassium carbonate solution. The aqueous phase is extracted twice with methylene chloride, and the organic phases are combined, dried over magnesium sulfate and concentrated by evaporation. The residue is chromatographed on silica gel with ethyl acetate. The title compound is obtained in the form of a white foam. MS (EI): 674 (M+), 544, 403, 241, 213,130. TLC: ethyl acetate, $R_f$=0.25.

(a) 4-(1H-Indol-3-yl)-3-oxo-butanoic acid ethyl ester 24.95 g (154 mmol) of carbonyldiimidazole are added at 0° C. to a solution of 24.5 g (140 mmol) of 3-indolyl-acetic acid in 250 ml of tetrahydrofuran and the mixture is stirred at 0° C. for 30 minutes. 46 g (161 mmol) of bis-(malonic acid monoethyl ester)magnesium salt are then added and the mixture is stirred at room temperature for 16 hours. The reaction mixture is concentrated by evaporation, and ice-cold 6N hydrochloric acid is added; diethyl ether is added and the organic phase is separated off. The organic phase is washed with aqueous 10% sodium hydrogen carbonate solution and brine, dried over magnesium sulfate and concentrated by evaporation. The title compound is obtained in the form of an orange oil. $^1$H-NMR (200 MHz): 8.22 (br. s, 1H), 7.53 (d, 1H), 7.37 (d, 1H), 7.28–7.10 (m, 3H), 4.23 (q, 2H), 3,93 (s, 2H), 3.46 (s, 2H), 1.22 (t, 3H).

(b) 4-(1H-Indol-3-yl)-3-methylamino-butanoic acid ethyl ester 75 ml (680 mmol) of an approximately 30% solution of methylamine in ethanol, 132 g (1.1 mol) of magnesium sulfate monohydrate and 1.5 ml of acetic acid are added to a solution of 33.4 g (136 mmol) of 4-(1H-indol-3-yl)-3-oxo-butanoic acid ethyl ester in 350 ml of methylene chloride. The mixture is stirred at room temperature for 66 hours. The mixture is then filtered and the filter residue is washed with 1.1 liters of methylene chloride. The filtrate is concentrated by evaporation. 250 ml of methanol, 22.33 g (272 mmol) of sodium acetate, 7.8 ml (136 mmol) of acetic acid and 12.08 g (163 mmol, 85% in oil) of sodium cyanoborohydride are added to the residue (a brown oil) and the mixture is stirred at room temperature for 16 hours. The mixture is concentrated by evaporation; 1N hydrochloric acid is added and the mixture is washed twice with diethyl ether. The diethyl ether phases are extracted three times with 1N hydrochloric acid. The combined aqueous phases are cooled and rendered basic with aqueous 50% sodium hydroxide solution. Ethyl acetate is then added. The organic phase is separated off and washed with brine, dried over magnesium sulfate and concentrated by evaporation. The title compound is obtained in the form of a brown oil. $^1$H-NMR (200 MHz): 8.21 (br. s, 1H), 7.64 (d, 1H), 7.37 (d, 1H), 7.28–7.04 (m, 3H), 4.12 (q, 2H), 3.28 (m, 1H), 2.95 (d, 2H), 2.48 (m, 5H), 1.27 (t, 3H).

(c) 3-(N-Benzyloxycarbonyl-N-methyl)-amino-4-(1H-indol-3-yl)-butanoic acid ethyl ester 6.7 ml (48 mmol) of triethylamine and 235 mg (1.92 mmol) of 4-dimethylaminopyridine are added at 0° C. to a solution of 5 g (19.2 mmol) of 4-(1H-indol-3-yl)-3-methylamino-butanoic acid ethyl ester in 100 ml of tetrahydrofuran. After 10 minutes 96 ml (42.3 mmol) of chloroformic acid benzyl ester are added dropwise at 0° C. in the course of 20 minutes and the mixture is stirred at room temperature for 18 hours. The mixture is filtered and the filtrate is concentrated by evaporation. Diethyl ether is added to the residue and the mixture is filtered over silica gel. The filtrate is concentrated by evaporation. The title compound is obtained in the form of a brown oil. MS (EI): 394 (M$^+$.), 229, 220, 130, 91. TLC: ethyl acetate/petroleum ether (1:1), R$_f$=0.41.

(d) 3-(N-Benzyloxycarbonyl-N-methyl)-amino-4-(1H-indol-3-yl)-butanal 34.8 ml (41.6 mmol) of a 20% solution of diisobutylaluminium hydride in toluene are added dropwise at –70° C. in the course of one hour to a solution of 8.8 g (19.2 mmol) of 3-(N-benzyloxycarbonyl-N-methyl)-amino-4-(1H-indol-3-yl)-3-methylamino-butanoic acid ethyl ester in 100 ml of toluene. After 2 hours' stirring at –70° C., 6 ml of methanol are slowly added dropwise. Then at 0° C. a solution of 51 g of potassium sodium tartrate in 200 ml of water is added dropwise in the course of one hour. The mixture is stirred at 0° C. for 18 hours and then diluted with diethyl ether. The organic phase is separated, washed with water and brine, dried over magnesium sulfate and concentrated by evaporation. The title compound is obtained in the form of a brown oil. MS (EI): 350 (M$^+$.), 185, 176, 130, 91. TLC: ethyl acetate/petroleum ether (1:1), R$_f$=0.32.

(e) 5-(N-Benzyloxycarbonyl-N-methyl)-amino-6-(1H-indol-3-yl)-hex-2-enoic acid ethyl ester 684 mg (15.7 mmol) of 55% sodium hydride in oil are added at 0° C. in four portions to a solution of 3.76 ml (18.8 mmol) of phosphonoacetic acid triethyl ester in 50 ml of tetrahydrofuran. After 30 minutes a solution of 7.6 g (19.21 mmol) of 3-(N-benzyloxycarbonyl-N-methyl)-amino-4-(1H-indol-3-yl)-butanal in 50 ml of tetrahydrofuran is added dropwise at 0° C. in the course of one hour. After one hour the mixture is poured onto ice and extracted with ethyl acetate. The organic phase is washed with ice-water and brine, then concentrated by evaporation. The residue is chromatographed on silica gel with ethyl acetate/petroleum ether (1:2, then 1:1). The title compound is obtained in the form of a yellowish oil. MS (EI): 420 (M$^+$.), 290, 246, 130, 91. TLC: ethyl acetate/petroleum ether (1:1), R$_f$=0.67.

(f) 6-(1H-Indol-3-yl)-5-methylamino-hexanoic acid ethyl ester trifluoroacetic acid salt A solution of 1.0 g (2.38 mmol) of 5-(N-benzyloxycarbonyl-N-methyl)-amino-6-(1H-indol-3-yl)-hex-2-enoic acid ethyl ester in 20 ml of ethanol and 0.38 ml (5 mmol) of trifluoroacetic acid is hydrogenated with 200 mg of 5% palladium-on-carbon at 22° C. under 1 atm. of hydrogen. After three hours the suspension is filtered over Hyflo and washed with ethanol and the filtrate is concentrated by evaporation. The title compound is obtained in the form of a yellow oil. MS (EI): 243 (M$^+$.-EtO), 173, 158, 130,112, 70. TLC: ethyl acetate, R$_f$=0.11.

(g) 5-[N-(3,5-Bistrifluoromethyl-benzoyl)-N-methyl-amino]-6-(1H-indol-3-yl)-hexanoic acid ethyl ester 1.16 ml (8.32 mmol) of triethylamine and then a solution of 947 mg (2.38 mmol) of 6-(1H-indol-3-yl)-5-methylamino-hexanoic acid ethyl ester trifluoracetic acid salt in 10 ml of tetrahydrofuran are added dropwise at 0° C. in the course of 30 minutes to a solution of 0.49 ml (2.61 mmol) of 97% 3,5-bistrifluoromethyl-benzoyl chloride in 10 ml of tetrahydrofuran. The mixture is stirred at room temperature for 18 hours, then filtered and washed with 10 ml of tetrahydrofuran. The filtrate is concentrated by evaporation and diethyl ether is added. The mixture is then filtered over silica gel and the filtrate is concentrated by evaporation. The title compound is obtained in the form of a brown oil. MS (EI): 528 (M$^+$.), 483, 398, 257, 241, 130. TLC: ethyl acetate, R$_f$=0.66.

(h) 5-[N-(3,5-Bistrifluoromethyl-benzoyl)-N-methyl-amino]-6-(1H-indol-3-yl)-hexanoic acid A solution of 108 mg (1.93 mmol) of potassium hydroxide in 1 ml of water is added at room temperature to a solution of 970 mg (1.84 mmol) of 5-[(3,5-bistrifluoromethyl-benzoyl)-N-methyl-amino]-6-(1H-indol-3-yl)-hexanoic acid ethyl ester in 10 ml of tetrahydrofuran. The mixture is stirred at room temperature for 18 hours and then 10 ml of water and 20 ml of diethyl ether are added. The aqueous phase is separated off and rendered acidic with 6N hydrochloric acid. Ethyl acetate is then added and the product is extracted. The combined organic phases are washed with brine, dried over magnesium sulfate and concentrated by evaporation. The title compound crystallises out from diethyl ether/hexane in the form of white crystals. M.p.: 152–157° C.; MS (EI): 500 (M$^+$.), 370, 241, 229,130; TLC: (ethyl acetate/acetic acid 99:1) R$_f$=0.49.

(i) 5-[N'-(3,5-Bistrifluoromethyl-benzoyl)-N'-methyl-amino]-6-(1H-indol-3-yl)-hexanoic acid N-hydroxy-succinimidyl ester 19 mg (0.15 mmol) of 4-dimethylaminopyridine and 92 mg (0.798 mmol) of N-hydroxysuccinimide are added to 380 mg (0.759 mmol) of 5-[N-(3,5-bistrifluoromethyl-benzoyl)-N-methyl-amino]-6-(1H-indol-3-yl)-hexanoic acid in 5 ml of methylene chloride. The mixture is cooled to 0° C., and 160 mg (0.835 mmol) of N-ethyl-N'-(3-dimethylamino-propyl)-carbodiimide hydrochloride are added. The reaction mixture is stirred at 0° C. for 15 minutes and then at room temperature for 20 hours. The mixture is washed with 10% citric acid and with brine. The organic phase is dried over magnesium sulfate and concentrated by evaporation. The title compound crystallises out from diethyl ether/hexane in the form of white crystals. M.p.: 159–160° C.; MS (EI): 597 (M+.), 483, 467, 326, 241, 130, 44. TLC: ethyl acetate, $R_f$=0.57.

The following are also prepared analogously to Example 14:

EXAMPLE 14/1
5-[N'-(3,5-Bistrifluoromethyl-benzoyl)-N'-methyl-amino]-6-(1H-indol-3-yl)-hexanoic acid N-butyl-N-(2-hydroxyethyl)-amide

EXAMPLE 14/2
5-[N'-(3,5-Bistrifluoromethyl-benzoyl)-N'-methyl-amino]-6-(1H-indol-3-yl)-hexanoic acid N,N-bis(2-cyanoethyl)-amide

EXAMPLE 14/3
5-[N'-(3,5-Bistrifluoromethyl-benzoyl)-N'-methyl-amino]-6-(1H-indol-3-yl)-hexanoic acid(4-morpholineamide)

EXAMPLE 14/4
5-[N'-(3,5-Bistrifluoromethyl-benzoyl)-N'-methyl-amino]-6-(1H-indol-3-yl)-hexanoic acid(1,2,4-triazole-1-amide)

EXAMPLE 14/5
5-[N'-(3,5-Bistrifluoromethyl-benzoyl)-N'-methyl-amino]-6-(1H-indol-3-yl)-hexanoic acid N-methyl-amide

EXAMPLE 15
5-[N'-(3,5-Bistrifluoromethyl-benzoyl)-N'-methyl-amino]-6-(1H-indol-3-yl)-hexanoic acid N-(2-chloro-4-methyl-phenyl)-amide 160 mg (0.268 mmol) of 5-[N-(3,5-bistrifluoromethyl-benzoyl)-N-methyl-amino]-6-(1H-indol-3-yl)-hexanoic acid are dissolved in 10 ml of methylene chloride, and then 222 ml (1.34 mmol) of triethylamine, 48 ml (0.382 mmol) of 2-chloro-4-methyl-aniline and 271 ml of 50% propylphosphonic acid anhydride solution in ethyl acetate are added. The reaction mixture is stirred at room temperature for 20 hours, then washed twice with aqueous potassium carbonate solution. The aqueous phase is extracted twice with methylene chloride, and the organic phases are combined, dried over magnesium sulfate and concentrated by evaporation. The residue is chromatographed on silica gel with ethyl acetate/petroleum ether (first 1:2, then 3:1). The title compound is obtained in the form of white crystals. MS (EI): 352, 241, 222, 213, 130. TLC: ethyl acetate, $R_f$=0.59.

The following are also prepared analogously to Example 15:

EXAMPLE 15/1
5-[N'-(3,5-Bistrifluoromethyl-benzoyl)-N'-methyl-amino]-6-(1H-indol-3-yl)-hexanoic acid N-(2,5-dichlorophenyl)-amide

EXAMPLE 15/2
5-[N'-(3,5-Bistrifluoromethyl-benzoyl)-N'-methyl-amino]-6-(1H-indol-3-yl)-hexanoic acid(3-acetyl-indole-1-amide)

EXAMPLE 15/3
5-[N'-(3,5-Bistrifluoromethyl-benzoyl)-N'-methyl-amino]-6-(1H-indol-3-yl)-hexanoic acid N-(pyrazin-2-yl)-amide

EXAMPLE 16
5-(N-(3,5)-Bistrifluoromethyl-benzoyl-N-methyl)-amino-6-(4-chlorophenyl)-hexanoic acid N-propyl-amide A solution of 0.51 g (1.03 mmol) of 5-(N-(3,5)-bistrifluoromethyl-benzoyl-N-methyl)-amino-6-(4-chlorophenyl)-hexanoic acid, 0.08 ml (0.98 mmol) of propylamine and 0.592 g (3.09 mmol) of N-ethyl-N'-(3-dimethylamino-propyl)-carbodiimide hydrochloride in 15 ml of dimethylformamide is stirred at room temperature under argon for 24 hours. The reaction mixture is taken up in ethyl acetate, washed with 1N hydrochloric acid, brine, saturated bicarbonate solution and again with brine, dried with sodium sulfate and concentrated in a rotary evaporator. The crude product can be chromatographed on 50 g of silica gel (ethyl acetate/methanol 1:0–1:1). The title compound is obtained in the form of a clear oil. TLC: ethyl acetate, $R_f$=0.51.

(a) N-tert-Butyloxycarbonyl-4-chlorophenylalanine

A solution of 54.6 g (250 mmol) of di-tert-butyl dicarbonate in 250 ml of n-butanol is added to a solution of 50 g (250 mmol) of (R,S)-4-chlorophenylalanine in 750 ml of 0.65N sodium hydroxide solution and the mixture is stirred at room temperature for 19 hours. The solution is then washed twice with ether, adjusted to pH 2 with 2N hydrochloric acid and extracted twice with ethyl acetate. The organic phases are washed with water and brine, dried with sodium sulfate and concentrated by evaporation. The crude product crystallises from hexane. M.p.: 145–146° C.

(b) N-tert-Butyloxycarbonyl-N-methyl-4-chlorophenylalanine methyl ester

A solution of N-tert-butyloxycarbonyl4-chlorophenylalanine in 150 ml of dimethylformamide is added dropwise at 0–5° C. under argon over a period of 30 minutes to a suspension of 6.9 g (273 mmol) of sodium hydride (95%) in 100 ml of toluene, with slight foaming. The solution is stirred at 0° C. for 15 minutes and at room temperature for 30 minutes, then 22.8 ml (365 mmol) of methyl iodide dissolved in 50 ml of dimethylformamide are added dropwise at 0° C. The reaction mixture is stirred at room temperature for 16 hours; the suspension is filtered with suction and then washed with ethyl acetate, and the organic phases are concentrated in a rotary evaporator. The residue is taken up in ethyl acetate and a small amount of methanol, washed with water and with brine and the organic phase is concentrated in a rotary evaporator. The crude product is filtered over silica gel (hexane/ethyl acetate 9:1). The title compound is obtained in the form of a clear oil. TLC: hexane/ethyl acetate 4:1, $R_f$=0.42.

(c) 2-(N-tert-Butyloxycarbonyl-N-methyl)-amino-3-(4-chlorophenyl)-propionaldehyde 56 ml (67 mmol) of diisobutylaluminium hydride (1.2M in toluene) are added dropwise at −70° C. in the course of 45 minutes to a solution of 11.0 g (33.5 mmol) N-tert-butyloxycarbonyl-N-methyl-4-chlorophenylalanine methyl ester in 220 ml of toluene and the mixture is stirred for 40 minutes. When the reaction is complete, 7 ml of methanol are slowly added dropwise and the solution is heated to 0° C. While stirring vigorously, a solution of 55 g of potassium tartrate in 200 ml of water is added. The suspension is taken up in ethyl acetate, washed with water and 5 times with brine. The organic phases are dried with sodium sulfate and concentrated in a rotary evaporator. Flash chromatography (hexane/ethyl acetate 9:1) yields the title compound in the form of a clear oil. TLC: hexane/ethyl acetate 4:1, $R_f$=0.40.

(d) 2-[4-(N-tert-Butyloxycarbonyl-N-methyl)-amino-5-(4-chlorophenyl)-pent-2-enyl]-1,3-dioxane 69.7 ml (108.9 mmol) of butyllithium (1.6M) are added at −25° C. to a suspension of 49.8 g (108.9 mmol) of 2-(1,3-dioxan-2-yl)-ethyl-triphenylphosphonium bromide in 330 ml of THF. The solution is stirred at −25° C. for 30 minutes, then cooled to −75° C., and a solution of 16.6 g (55.7 mmol) of 2-(N-tert-butyloxycarbonyl-N-methyl)-amino- 3-(4-chlorophenyl)-propionaldehyde in 165 ml of THF is added dropwise thereto. The reaction is maintained at −75° C. for 30 minutes, then the mixture is heated to room temperature in the course of ~1 hour and stirred at room temperature for a further 2.5 hours. 200 ml of water are added to the orange solution and the mixture is taken up in ethyl acetate. The organic phase is washed with water and with brine, dried with sodium sulfate and concentrated in a rotary evaporator. The crude product is filtered over 600 g of silica gel with hexane/ethyl acetate (1 liter 95:5, 1 liter 4:1). The title compound is obtained in the form of a clear oil. TLC: hexane/ethyl acetate 4:1, $R_f$=0.32.

(e) 2-[4-(N-tert-Butyloxycarbonyl-N-methyl)-amino-5-(4-chlorophenyl)-pentyl]-1,3-dioxane A solution of 11.0 g (27.8 mmol) of 2-[4-(N-tert-butyloxycarbonyl-N-methyl)-amino-5-(4-chlorophenyl)-pent-2-enyl]-1,3-dioxane in 250 ml of ethyl acetate is hydrogenated with hydrogen with 3 g of Raney nickel at room temperature under normal pressure. After 2 hours the suspension is filtered and the filtrate is concentrated. The product is obtained in the form of a clear oil. TLC: hexane/ethyl acetate 4:1, $R_f$=0.29.

(f) 5-(N-tert-Butyloxycarbonyl-N-methyl)-amino-6-(4-chlorophenyl)-hexanoic acid 3-hydroxy-propyl ester Ozone is introduced at −75° C. over a period of 7.5 hours into a solution of 17.2 g (43.2 mmol) of 2-[4-(N-tert-butyloxycarbonyl-N-methyl)-amino-5-(4-chlorophenyl)-pentyl]-1,3-dioxane in 320 ml of ethyl acetate. When the reaction is complete, the excess ozone can be blown out with argon. The solution is heated to room temperature, taken up in ethyl acetate, extracted with saturated bicarbonate solution and washed with water and with brine. The organic phases are dried with sodium sulfate and concentrated in a rotary evaporator. The crude product can be chromatographed over silica gel (hexane/ethyl acetate 7:3). The title compound is obtained in the form of a clear oil. TLC: hexane/ethyl acetate 1:1, $R_f$=0.30.

(g) 5-Methylamino-6-(4-chlorophenyl)-hexanoic acid 3-hydroxy-propyl ester 11.2 g (27.1 mmol) of 5-(N-tert-butyloxycarbonyl-N-methyl)-amino-6-(4-chlorophenyl)-hexanoic acid 3-hydroxy-propyl ester are dissolved in 60 ml of methylene chloride, and 60 ml of trifluoroacetic acid are added. The reaction solution is stirred at room temperature for 30 minutes and then concentrated in a rotary evaporator. After three times dissolving in toluene and concentrating in a rotary evaporator, the crude product is obtained in the form of a clear oil which is used without further purification.

(h) 5-(N-(3,5)-Bistrifluoromethyl-benzoyl-N-methyl)-amino-6-(4-chlorophenyl)-hexanoic acid 3-hydroxy-propyl ester 28.9 ml (208.5 mmol) of triethylamine and 0.618 g (5.1 mmol) of 4-dimethylaminopyridine are added at room temperature under argon to a solution of 16.15 g (51.5 mmol) of 5-methylamino-6-(4-chlorophenyl)-hexanoic acid 3-hydroxy-propyl ester in 290 ml of methylene chloride and the mixture is cooled to 0° C. After the dropwise addition of 17.54 g (63.4 mmol) of (3,5)-bistrifluoromethyl-benzoyl chloride in 23 ml of methylene chloride, the reaction mixture is stirred at 0° C. for 16 hours, then ethyl acetate is added and the mixture is washed with water and brine. The organic phases are dried with sodium sulfate and concentrated in a rotary evaporator. The crude product can be chromatographed on silica gel (hexane/ethyl acetate 7:3). The title compound is obtained in the form of a clear oil. TLC: hexane/ethyl acetate 3:7, $R_f$=0.45.

(i) 5-(N-(3,5)-Bistrifluoromethyl-benzoyl-N-methyl)-amino-6-(4-chlorophenyl)-hexanoic acid A solution of 3.08 g of potassium hydroxide in 6.25 ml of water is added to a solution of 7.2 g (13.0 mmol) of 5-(N-(3,5)-bistrifluoromethyl-benzoyl-N-methyl)-amino-6-(4-chlorophenyl)-hexanoic acid 3-hydroxy-propyl ester in 26.5 ml of ethanol and the reaction mixture is heated under reflux for 45 minutes. At 0° C., 31.2 ml of 2N hydrochloric acid are added and the solution is extracted with ethyl acetate. The organic phases are washed with brine, dried with sodium sulfate and concentrated in a rotary evaporator. The title compound is obtained in the form of a a yellowish foam. TLC: ethyl acetate, $R_f$=0.49.

Analogously to Example 16, the following compounds are also prepared:

EXAMPLE 16/1

5-(N-(3,5)-Bistrifluoromethyl-benzoyl-N-methyl)-amino-6-(4-chlorophenyl)-hexanoic acid N-(cyclohexylmethyl)-amide; TLC: hexane/ethyl acetate 3:7, $R_f$=0.39

EXAMPLE 16/2

5-(N-(3,5)-Bistrifluoromethyl-benzoyl-N-methyl)-amino-6-(4-chlorophenyl)-hexanoic acid N-[2-(2-pyridyl)-ethyl]-amide; TLC: ethyl acetate/methanol 9:1, $R_f$=0.47

EXAMPLE 16/3

5-(N-(3,5)-Bistrifluoromethyl-benzoyl-N-methyl)-amino-6-(4-chlorophenyl)-hexanoic acid N-(2-methoxy-benzyl)-amide; TLC: hexane/ethyl acetate 3:7, $R_f$=0.34

EXAMPLE 16/4

5-(N-(3,5)-Bistrifluoromethyl-benzoyl-N-methyl)-amino-6-(4-chlorophenyl)-hexanoic acid N-(2-pyridylmethyl)-amide; TLC: ethyl acetate/methanol 9:1, $R_f$=0.50

EXAMPLE 16/5

5-(N-(3,5)-Bistrifluoromethyl-benzoyl-N-methyl)-amino-6-(4-chlorophenyl)-hexanoic acid(piperidineamide); TLC: hexane/ethyl acetate 3:7, $R_f$=0.23

EXAMPLE 17

5-(N-(3,5)-Bistrifluoromethyl-benzoyl-N-methyl)-amino-6-(4-chlorophenyl)-hexanoic acid N,N-diallylamide A solution of 12.6 ml (0.18 mmol) of triethylamine in 0.4 ml of methylene chloride and a solution of 45 mg (0.076 mmol) of 5-(N-(3,5)-bistrifluoromethyl-benzoyl-N-methyl)-amino-6-(4-chlorophenyl)-hexanoic acid N-hydroxysuccinimide ester are added in succession at room temperature to 8.85 mg (0.091 mmol) of diallylamine and the mixture is left to stand at room temperature overnight (>16 hours). 0.5 ml of 1N potassium carbonate solution is then added and the mixture is shaken and briefly centrifuged to separate the phases. The organic phase is concentrated. The title compound is obtained in the form of a clear oil. TLC: methylene chloride/methanol 95:5, $R_f$=0.70.

(a) 5-(N-(3,5)-Bistrifluoromethyl-benzoyl-N-methyl)-amino-6-(4-chlorophenyl)-hexanoic acid N-hydroxysuccinimide ester A solution of 10.41 g (21 mmol) of 5-(N-(3,5)-bistrifluoromethyl-benzoyl-N-methyl)-amino-6-(4-chlorophenyl)-hexanoic acid, 2.53 g (22 mmol) of N-hydroxysuccinimide, 4.72 g (23 mmol) of N,N'-dicyclohexylcarbodiimide and 500 ml of tetrahydrofuran is stirred at room temperature under argon for 16 hours. The reaction solution is filtered and concentrated in a rotary evaporator. The residue is twice digested in ether, filtered and concentrated in a rotary evaporator. The crude product is dried under a high vacuum. The title compound is obtained in the form of a yellowish foam. TLC: hexane/ethyl acetate 2:3, $R_f$=0.54.

Analogously to Example 17, the following compounds are also prepared:

EXAMPLE 17/1
5-(N-(3,5)-Bistrifluoromethyl-benzoyl-N-methyl)-amino-6-(4-chlorophenyl)-hexanoic acid N-cyclohexyl-amide; TLC: methylene chloride/methanol 95:5, $R_f$=0.70

EXAMPLE 17/2
5-(N-(3,5)-BistrifluoromethyL-benzoyl-N-methyl)-amino-6-(4-chlorophenyl)-hexanoic acid N-(2-cyanoethyl)-N-methyl-amide; TLC: ethyl acetate, $R_f$=0.70

EXAMPLE 18
4-[N'-Methyl-N'-(3,5-bistrifluoromethyl-benzoyl)-amino]-5-(1-methyl-indol-3-yl)-pentanoic acid N-(3-chlorobenzyl)-amide 26.4 μl of triethylamine are added to a solution of 108.5 mg of 4-[N'-methyl-N'-(3,5-bistrifluoromethyl-benzoyl)-amino]-5-(1-methyl-indol-3-yl)-pentanoic acid hydroxysuccinimide ester and 27 mg of 3-chlorobenzylamine in 1 ml of methylene chloride. The reaction mixture is left to stand at room temperature for 18 hours. The reaction mixture is then concentrated by evaporation, and the residue is taken up in ethyl acetate and washed in succession with 2N potassium carbonate solution, water, 0.1N hydrochloric acid, and brine, dried over sodium sulfate and again concentrated by evaporation. In this way the title compound is obtained in the form of a colourless foam. $R_f$ value=0.40 (ethyl acetate).

The starting materials can be prepared as follows:
(a) 4-[N'-Methyl-N'-(3,5-bistrifluoromethyl-benzoyl)-amino]-5-(1-methyl-indol-3-yl)-pentanoic acid hydroxysuccinimide ester A solution of 13.49 g of 4-[N'-methyl-N'-(3,5-bistrifluoromethyl-benzoyl)-amino]-5-(1-methyl-indol-3-yl)-pentanoic acid, 3.23 g of N-hydroxysuccinimide and 6.05 g of N,N'-dicyclohexylcarbodiimide in 500 ml of tetrahydrofuran is stirred at room temperature for 18 hours. The reaction solution is then filtered and the filtrate is concentrated by evaporation. The residue is taken up in ether and again filtered and concentrated by evaporation. In this way the title compound is obtained in the form of a colourless white foam. $R_f$ value=0.15 (ethyl acetate/hexane 1:1).
(b) 4-[N-Methyl-N-(3,5-bistrifluoromethyl-benzoyl)-amino]-5-(1-methyl-indol-3-yl)-pentanoic acid A solution of 15 g of 4-[N-methyl-N-(3,5-bistrifluoromethyl-benzoyl)-amino]-5(1-methyl-indol-3-yl)-pentanoic acid ethyl ester and 1.78 g of lithium hydroxide in 102.5 ml of tetrahydrofuran/methanol/water =2/2/1 is stirred at room temperature for 3 hours and then concentrated by evaporation. The residue is dissolved in 150 ml of water, extracted with ether, acidified to pH=2 with 0.1N hydrochloric acid and extracted three times with ether. The combined organic phases originating from the extraction of the acidic aqueous phase are washed with water and saturated NaCl solution, dried (magnesium sulfate) and concentrated by evaporation. In this way the title compound is obtained in the form of a yellow foam. $R_f$ value=0.10 (ethyl acetate/hexane 1:1).
(c) 4-[N-Methyl-N-(3,5-bistrifluoromethyl-benzoyl)-amino]-5-(1-methyl-indol-3-yl)-pentanoic acid ethyl ester A solution of 16.82 g of 4-[N-methyl-N-(3,5-bistrifluoromethyl-benzoyl)-amino]-5-(1-methyl-indol-3-yl)-pent-2-enoic acid ethyl ester in 170 ml of tetrahydrofuran is hydrogenated for 70 minutes at 20° C. in the presence of 1.7 g of palladium/activated carbon (10%) and 0.2 g of 1,2-dichlorobenzene. The reaction mixture is then filtered and concentrated by evaporation. In this way the title compound is obtained in the form of a brownish-green resin. $R_f$ value=0.265 (ethyl acetate/hexane 2/3).
(d) 4-[N-Methyl-N-(3,5-bistrifluoromethyl-benzoyl)-amino]-5-(1-methyl-indol-3-yl)-pent-2-enoic acid ethyl ester 28.05 g of 3,5-bis-trifluoromethyl-benzoyl chloride, 51.15 ml of triethylamine and 2.25 g of 4-dimethylamino-pyridine are added at 0° under argon to a solution of 26.74 g of 4-(N-methyl)-amino-5-(1-methyl-indol-3-yl)-pent-2-enoic acid ethyl ester in 320 ml of methylene chloride. The reaction mixture is stirred at 20° for 18 hours and then poured into water. The organic phase is separated off and the aqueous phase is extracted a further three times with ethyl acetate. The combined organic phases are washed with 0.01N hydrochloric acid, water and saturated NaCl solution, dried (magnesium sulfate) and concentrated by evaporation. The residue is chromatographed (silica gel, hexane/ethyl acetate 7:3). In this way the title compound is obtained in the form of a colourless resin which turns a brownish colour with time. $R_f$ value=0.29 (ethyl acetate/hexane 2/3).
(e) 4-(N-Methyl)-amino-5-(1-methyl-indol-3-yl)-pent-2-enoic acid ethyl ester 106.7 ml of trifluoroacetic acid are added dropwise over a period of 20 minutes to a solution of 35.57 g of 4-(N-methyl-N-tert-butyloxycarbonyl)-amino-5-(1-methyl-indol-3-yl)-pent-2-enoic acid ethyl ester in 284 ml of methylene chloride. The reaction mixture is stirred at room temperature for 1 hour and then concentrated by evaporation. The residue is dissolved in 300 ml of toluene and again concentrated by evaporation. That step is repeated twice more. The crude product so obtained (brownish oil) can be processed further without being further purified. $R_f$ value=0.01 (ethyl acetate/hexane 1:1).
(f) 4-(N-Methyl-N-tert-butyloxycarbonyl)-amino-5-(1-methyl-indol-3-yl)-pent-2-enoic acid ethyl ester 5.71 g of sodium hydride (100%) are added in portions at 0° to a solution of 53.9 g of phosphonoacetic acid triethyl ester in 686 ml of absolute tetrahydrofuran and the mixture is stirred at that temperature for 30 minutes. A solution of 44.6 g of N-methyl-N-tert-butyloxycarbonyl-amino-3-(1-methyl-indol-3-yl)-propanal in 686 ml of THF is then added dropwise over a period of 70 minutes. When the dropwise addition is complete, the mixture is stirred at 0° for a further 30 minutes. The reaction mixture is then poured into water and extracted three times using 300 ml of ether each time. The combined organic phases are washed three times with water and once with saturated NaCl solution, dried (magnesium sulfate) and concentrated by evaporation. The residue is purified by chromatography (silica gel, hexane/ethyl acetate 3:1). In this way the title compound is obtained in the form of a yellow oil. $R_f$ value=0.405 (ethyl acetate/hexane 1:1).
(g) N-Methyl-N-tert-butyloxycarbonyl-amino-3-(1-methyl-indol-3-yl)-propanal A solution of 44.24 g of N-methyl-N-tert-butyloxycarbonyl-amino-3-(1-methyl-indol-3-yl)-propanecarboxylic acid methyl ester in 1000 ml of toluene is cooled to −78° under argon. At that temperature 293.3 ml of a 20% diisobutylaluminium hydride solution in toluene are slowly added dropwise. When the dropwise addition is complete, the mixture is stirred at that temperature for 30 minutes. Then at the same temperature 42 ml of methanol and at 0° 1674 ml of a solution of 490 g of potassium sodium tartrate in water are added to the reaction mixture. The mixture is stirred vigorously at 0° for 2 hours. The phases are then separated and the aqueous phase is extracted three times using 1.5 liters of diethyl ether each time. The combined organic phases are washed with water and saturated NaCl solution, dried (magnesium sulfate) and concentrated by evaporation. The title compound is thus obtained in the form of a yellow oil and is reacted further without being purified. $R_f$ value=0.325 (ethyl acetate/hexane 1/2).

(h) N-Methyl-N-tert-butyloxycarbonyl-amino-3-(1-methyl-indol-3-yl)-propanecarboxylic acid methyl ester 303.1 g of silver(I) oxide are added, with stirring, to a solution of 77 g of tertbutyloxycarbonyl-D,L-tryptophan in 770 ml of N,N-dimethylformamide. 78.9 ml of methyl iodide are then added dropwise. The reaction mixture rises to a temperature of 45° and is stirred at room temperature for 1 day. After the addition of a further 78 ml of methyl iodide the mixture is stirred at room temperature for a further 18 hours and then diluted with 800 ml of ethyl acetate, filtered and concentrated by evaporation. The residue is purified by chromatography (silica gel, hexane/ethyl acetate 3:1). In this way the title compound is obtained in the form of a yellow oil. $R_f$ value=0.31 (ethyl acetate/hexane 1/2).

In a manner analogous to that described in Example 18, the following compounds are also prepared:

EXAMPLE 18/1
4-[N'-Methyl-N'-(3,5-bistrifluoromethyl-benzoyl)-amino]-5-(1-methyl-indol-3-yl)-pentanoic acid N-(3,4-dichloro-benzyl)-amide, $R_f$ value (ethyl acetate)=0.38

EXAMPLE 18/2
4-[N'-Methyl-N'-(3,5-bistrifluoromethyl-benzoyl)-amino]-5-(1-methyl-indol-3-yl)-pentanoic acid N-(4-methoxy-benzyl)-amide, $R_f$ value (ethyl acetate)=0.42

EXAMPLE 18/3
4-[N'-Methyl-N'-(3,5-bistrifluoromethyl-benzoyl)-amino]-5-(1-methyl-indol-3-yl)-pentanoic acid N-[2-(2-pyridyl)-ethyl]-amide, $R_f$ value (ethyl acetate)=0.07

EXAMPLE 18/4
4-[N'-Methyl-N'-(3,5-bistrifluoromethyl-benzoyl)-amino]-5-(1-methyl-indol-3-yl)-pentanoic acid N-[2-(4-hydroxy-phenyl)-ethyl]-amide, $R_f$ value (ethyl acetate)=0.37

EXAMPLE 18/5
4-[N'-Methyl-N'-(3,5-bistrifluoromethyl-benzoyl)-amino]-5-(1-methyl-indol-3-yl)-pentanoic acid N-(2-pyridylmethyl)-amide, $R_f$ value (ethyl acetate)=0.13

EXAMPLE 18/6
4-[N'-Methyl-N'-(3,5-bistrifluoromethyl-benzoyl)-amino]-5-(1-methyl-indol-3-yl)-pentanoic acid N-([3-(morpholin-4-yl)-propyl])-amide, $R_f$ value (ethyl acetate)=0.05

EXAMPLE 18/7
4-[N'-Methyl-N'-(3,5-bistrifluoromethyl-benzoyl)-amino]-5-(1-methyl-indol-3-yl)-pentanoic acid N-propyl-amide, $R_f$ value (ethyl acetate)=0.315

EXAMPLE 18/8
4-[N'-Methyl-N'-(3,5-bistrifluoromethyl-benzoyl)-amino]-5-(1-methyl-indol-3-yl)-pentanoic acid N-(5-hydroxy-pentyl)-amide, $R_f$ value (ethyl acetate)=0.17

EXAMPLE 18/9
4-[N'-Methyl-N'-(3,5-bistrifluoromethyl-benzoyl)-amino]-5-(1-methyl-indol-3-yl)-pentanoic acid N-(carbamoylmethyl)-amide, $R_f$ value (ethyl acetate)=0.04

EXAMPLE 18/10
4-[N'-Methyl-N'-(3,5-bistrifluoromethyl-benzoyl)-amino]-5-(1-methyl-indol-3-yl)-pentanoic acid N-(1-phenyl-ethyl)-amide, $R_f$ value (ethyl acetate)=0.46

EXAMPLE 18/11
4-[N'-Methyl-N'-(3,5-bistrifluoromethyl-benzoyl)-amino]-5-(1-methyl-indol-3-yl)-pentanoic acid(2-methyl-aziridineamide), $R_f$ value (ethyl acetate)=0.48

EXAMPLE 18/12
4-[N'-Methyl-N'-(3,5-bistrifluoromethyl-benzoyl)-amino]-5-(1-methyl-indol-3-yl)-pentanoic acid N-[2-hydroxy-2-(4-hydroxy-phenyl)-ethyl]-amide, $R_f$ value (ethyl acetate)=0.57

EXAMPLE 18/13
4-[N'-Methyl-N'-(3,5-bistrifluoromethyl-benzoyl)-amino]-5-(1-methyl-indol-3-yl)-pentanoic acid N-(benzoylmethyl)-amide, $R_f$ value (ethyl acetate)=0.39 [amine used: phenacylamine]

EXAMPLE 18/14
4-[N'-Methyl-N'-(3,5-bistrifluoromethyl-benzoyl)-amino]-5-(1-methyl-indol-3-yl)-pentanoic acid N-(5-methyl-1,3,4-thiadiazol-2-yl)-amide, $R_f$ value (ethyl acetate)=0.19

EXAMPLE 18/15
4-[N'-Methyl-N'-(3,5-bistrifluoromethyl-benzoyl)-amino]-5-(1-methyl-indol-3-yl)-pentanoic acid N-(thiazol-2-yl)-amide, $R_f$ value (ethyl acetate)=0.46

EXAMPLE 18/16
4-[N'-Methyl-N'-(3,5-bistrifluoromethyl-benzoyl)-amino]-5-(1-methyl-indol-3-yl)-pentanoic acid N-(3-dimethylamino-propyl)-amide, $R_f$ value (ethyl acetate)=0.04

EXAMPLE 18/17
4-[N'-Methyl-N'-(3,5-bistrifluoromethyl-benzoyl)-amino]-5-(1-methyl-indol-3-yl)-pentanoic acid N-[2-(3,4-dihydroxy-phenyl)-ethyl]-amide, $R_f$ value (ethyl acetate)=0.37

EXAMPLE 18/18
4-[N'-Methyl-N'-(3,5-bistrifluoromethyl-benzoyl)-amino]-5-(1-methyl-indol-3-yl)-pentanoic acid N-(D,L-homocysteine thiolactone)-amide, $R_f$ value (ethyl acetate)=0.42 [amine used: D,L-homocysteine thiolactone]

EXAMPLE 18/19
4-[N'-Methyl-N'-(3,5-bistrifluoromethyl-benzoyl)-amino]-5-(1-methyl-indol-3-yl)-pentanoic acid N-(D,L-epsilon-caprolactam-3-yl)-amide, $R_f$ value (ethyl acetate)=0.11, [amine used: D,L-3-amino-epsilon-caprolactam=3-amino-azacycloheptan-2-one]

EXAMPLE 18/20
4-[N'-Methyl-N'-(3,5-bistrifluoromethyl-benzoyl)-amino]-5-(1-methyl-indol-3-yl)-pentanoic acid N-(1-naphthylmethyl)-amide, $R_f$ value (ethyl acetate)=0.48

EXAMPLE 18/21
4-[N'-Methyl-N'-(3,5-bistrifluoromethyl-benzoyl)-amino]-5-(1-methyl-indol-3-yl)-pentanoic acid N-(3-methyl-isothiazol-5-yl)-amide, $R_f$ value (ethyl acetate)=0.33

EXAMPLE 18/22
4-[N'-Methyl-N'-(3,5-bistrifluoromethyl-benzoyl)-amino]-5-(1-methyl-indol-3-yl)-pentanoic acid N-[2-(morpholin-4-yl)-ethyl]-amide, $R_f$ value (ethyl acetate)=0.06

EXAMPLE 18/23
4-[N'-Methyl-N'-(3,5-bistrifluoromethyl-benzoyl)-amino]-5-(1-methyl-indol-3-yl)-pentanoic acid N-(4-pyridylmethyl)-amide, $R_f$ value (ethyl acetate)=0.09

EXAMPLE 18/24
4-[N'-Methyl-N'-(3,5-bistrifluoromethyl-benzoyl)-amino]-5-(1-methyl-indol-3-yl)-pentanoic acid N-(5-cyanopentyl)-amide, $R_f$ value (ethyl acetate)=0.31

EXAMPLE 18/25
4-[N'-Methyl-N'-(3,5-bistrifluoromethyl-benzoyl)-amino]-5-(1-methyl-indol-3-yl)-pentanoic acid N-(4-methoxybenzyl)-amide, $R_f$ value (ethyl acetate)=0.47

EXAMPLE 18/26
4-[N'-Methyl-N'-(3,5-bistrifluoromethyl-benzoyl)-amino]-5-(1-methyl-indol-3-yl)-pentanoic acid N-[2-(4-methoxyphenyl)-ethyl]-amide, $R_f$ value (ethyl acetate)=0.43

EXAMPLE 18/27
4-[N'-Methyl-N'-(3,5-bistrifluoromethyl-benzoyl)-amino]-5-(1-methyl-indol-3-yl)-pentanoic acid N-(D-phenylglycinol)-amide, {=4-[N'-methyl-N'-(3,5-bistrifluoromethyl-benzoyl)-amino]-5-(1-methyl-indol-3-yl)-pentanoic acid N-[(1R)-2-hydroxy-1-phenyl-ethyl)-amide]} $R_f$ value (ethyl acetate)=0.28

EXAMPLE 19
In a manner analogous to that described under Example 18 but using 4-[N-methyl-N-(3,5-bistrifluoromethyl-benzoyl)-amino]-5-(1-methyl-indol-3-yl)-pent-2-enoic acid hydroxysuccinimide ester, 4-[N'-methyl-N'-(3,5-bistrifluoromethyl-benzoyl)-amino]-5-(1-methyl-indol-3-yl)-pent-2-enoic acid N-(3,4-dichloro-benzyl)-amide is also prepared The starting material can be prepared as follows:
(a) 4-[N'-Methyl-N'-(3,5-bistrifluoromethyl-benzoyl)-amino]-5-(1-methyl-indol-3-yl)-pent-2-enoic acid hydroxysuccinimide ester A solution of 10.11 g of 4-[N'-methyl-N'-(3,5-bistrifluoromethyl-benzoyl)-amino]-5-(1-methyl-indol-3-yl)-pent-2-enoic acid, 2.42 g of N-hydroxysuccinimide and 4.54 g of N,N'-dicyclohexylcarbodiimide in 375 ml of tetrahydrofuran is stirred at room temperature for 18 hours. The reaction solution is then filtered and the filtrate is concentrated by evaporation. The residue is taken up in ether and again filtered and concentrated by evaporation. In this way the title compound is obtained in the form of a colourless white foam. $R_f$ value=0.17 (ethyl acetate/hexane 1:1).
(b) 4-[N-Methyl-N-(3,5-bistrifluoromethyl-benzoyl)-amino]-5-(1-methyl-indol-3-yl)-pent-2-enoic acid A solution of 9.51 g of 4-[N-methyl-N-(3,5-bistrifluoromethyl-benzoyl)-amino]-5-(1-methyl-indol-3-yl)-pent-2-enoic acid ethyl ester and 1.14 g of lithium hydroxide in 65 ml of tetrahydrofuran/methanol/water =2/2/1 is stirred at room temperature for 15 hours and then concentrated by evaporation. The residue is dissolved in 150 ml of water with heating to 55°, extracted with ether at 20°, acidified to pH=2 with 0.1N hydrochloric acid and extracted three times with ether. The combined organic phases originating from the extraction of the acidic aqueous phase are washed with water and saturated NaCl solution, dried (magnesium sulfate) and concentrated by evaporation. In this way the title compound is obtained in the form of a yellow foam. $R_f$ value=0.13 (ethyl acetate).

Analogously to Example 19, the following compounds also are prepared:

EXAMPLE 19/1
4-[N'-Methyl-N'-(3,5-bistrifluoromethyl-benzoyl)-amino]-5-(1-methyl-indol-3-yl)-pent-2-enoic acid N-(4-methoxybenzyl)-amide

EXAMPLE 19/2
4-[N'-Methyl-N'-(3,5-bistrifluoromethyl-benzoyl)-amino]-5-(1-methyl-indol-3-yl)-pent-2-enoic acid N-[2-(2-pyridyl)-ethyl]-amide, TLC: methylene chloride/methanol (95:5) $R_f$=0.19

EXAMPLE 19/3
4-[N'-Methyl-N'-(3,5-bistrifluoromethyl-benzoyl)-amino]-5-(1-methyl-indol-3-yl)-pent-2-enoic acid N-[2-(4-hydroxyphenyl)-ethyl]-amide

EXAMPLE 19/4
4-[N'-Methyl-N'-(3,5-bistrifluoromethyl-benzoyl)-amino]-5-(1-methyl-indol-3-yl)-pent-2-enoic acid N-(2-pyridylmethyl)-amide

EXAMPLE 19/5
4-[N'-Methyl-N'-(3,5-bistrifluoromethyl-benzoyl)-amino]-5-(1-methyl-indol-3-yl)-pent-2-enoic acid N-[3-(morpholin-4-yl)-propyl]-amide, TLC: methylene chloride/methanol (95:5) $R_f$=0.07

EXAMPLE 19/6
4-[N'-Methyl-N'-(3,5-bistrifluoromethyl-benzoyl)-amino]-5-(1-methyl-indol-3-yl)-pent-2-enoic acid N-propyl-amide

EXAMPLE 19/7
4-[N'-Methyl-N'-(3,5-bistrifluoromethyl-benzoyl)-amino]-5-(1-methyl-indol-3-yl)-pent-2-enoic acid N-(5-hydroxypentyl)-amide

EXAMPLE 19/8
4-[N'-Methyl-N'-(3,5-bistrifluoromethyl-benzoyl)-amino]-5-(1-methyl-indol-3-yl)-pent-2-enoic acid N-(carbamoylmethyl)-amide

EXAMPLE 20
4-[N'-Methyl-N'-(3,5-bistrifluoromethyl-benzoyl)-amino]-5-(naphth-2-yl)-pentanoic acid N-(3-chlorobenzyl)-amide 11.7 μl of triethylamine are added to a solution of 45.42 mg of 4-[N'-methyl-N'-(3,5-bistrifluoromethyl-benzoyl)-amino]-5(naphth-2-yl)-pentanoic acid hydroxysuccinimide ester and 11.9 mg of 3-chlorobenzylamine in 1 ml of methylene chloride. The reaction mixture is left to stand at room temperature for 18 hours. Then 0.5 ml of 1N potassium carbonate solution is added and the mixture is shaken vigorously. After separation of the phases, the organic phase is separated off and concentrated by evaporation. In this way the title compound is obtained in the form of a white foam.

The starting materials can be prepared as follows:
a) 4-[N'-Methyl-N'-(3.5-bistrifluoromethyl-benzoyl)-amino]-5-(naphth-2-yl)-pentanoic acid hydroxysuccinimide ester A solution of 10.0 g of 4-[N-methyl-N-(3,5-bistrifluoromethylbenzoyl)-amino]-5-(naphth-2-yl)-pentanoic acid, 2.4 g of N-hydroxysuccinimide and 4.52 g of N,N'-dicyclohexylcarbodiimide in 400 ml of tetrahydrofuran is stirred at room temperature for 18 hours. The reaction solution is then filtered and the filtrate is concentrated by evaporation. The residue is taken up in ether and again filtered and concentrated by evaporation. In this way the title compound is obtained in the form of a slightly yellowish amorphous solid. $R_f$ value=0.52 (hexane/ethyl acetate 1:4).

IR (CH$_2$Cl$_2$): 3060, 2940, 2860, 1810, 1745,1640, 1340, 1280, 1260,1210,1190, 1145, 1070 cm$^{-1}$.

b) 4-[N-Methyl-N-(3,5-bistrifluoromethyl-benzoyl)-amino]-5-(naphth-2-yl)-pentanoic acid A solution of 19.5 g of 4-[N-methyl-N-(3,5-bistrifluoromethyl-benzoyl)-amino]-5-(naphth-2-yl)-pentanoic acid ethyl ester and 7.8 g of lithium hydroxide (monohydrate) in 212 ml of methanol, 148 ml of tetrahydrofuran and 60 ml of water is stirred at room temperature for 75 minutes and then concentrated by evaporation. The residue is dissolved in 150 ml of water, acidified to pH=2 with 0.1N hydrochloric acid and extracted three times with ethyl acetate. The combined organic phases are washed with water and saturated NaCl solution, dried (magnesium sulfate) and concentrated by evaporation. In this way the title compound is obtained in the form of a yellow foam. $R_f$ value=0.50 (hexane/ethyl acetate 1:4). IR (CH$_2$Cl$_2$): 3053, 1712, 1639, 1406, 1341, 1278, 1183, 1141, 1108, 904, 849, 821 cm$^{-1}$.

c) 4-[N-Methyl-N-(3,5-bistrifluoromethyl-benzoyl)-amino]-5-(naphth-2-yl)-pentanoic acid ethyl ester A solution of 20.0 g of 4-[N-methyl-N-(3,5-bistrifluoromethyl-benzoyl)-amino]-5-(naphth- 2-yl)-pent-2-enoic acid ethyl ester in 200 ml of tetrahydrofuran is hydrogenated at 20° C. for 2 hours in the presence of 1.0 g of palladium/activated carbon (10%). The reaction mixture is then filtered and concentrated by evaporation. In this way the title compound is obtained in the form of a colourless oil. $R_f$ value=0.50 (hexane/ethyl acetate:1:1). IR(CH$_2$Cl$_2$) cm$^{-1}$: 2978, 1729, 1639, 1405, 1339, 1278, 1183, 1141, 903, 849, 820.

d) 4-[N-Methyl-N-(3.5-bistrifluoromethyl-benzoyl)-amino]-5-(naphth-2-yl)-pent-2-enoic acid ethyl ester 9.7 ml of 3,5-bistrifluoromethyl-benzoyl chloride, 27.2 ml of triethylamine and 1.2 g of 4-dimethylamino-pyridine are added at 0° under argon to a solution of 13.8 g of 4-(N-methyl)-amino-5-(naphth-2-yl)-pent-2-enoic acid ethyl ester in 170 ml of methylene chloride. The reaction mixture is stirred at 20° for 100 minutes and then poured into water. The organic phase is separated off and the aqueous phase is extracted a further three times with methylene chloride. The combined organic phases are washed with 0.01N hydrochloric acid, water and saturated NaCl solution, dried (magnesium sulfate) and concentrated by evaporation. The residue is chromatographed (silica gel, hexane/ethyl acetate 7:3). In this way the title compound is obtained in the form of a yellowish oil. $R_f$ value=0.16 (methylene chloride/methanol 9:1). IR(CH$_2$Cl$_2$) cm$^{-1}$: 2979, 1717, 1644, 1446, 1403, 1369,1311,1277, 1183, 1141, 905, 849, 820.

e) 4-(N-Methyl)-amino-5-(naphth-2-yl)-pent-2-enoic acid ethyl ester 24.1 ml of trifluoroacetic acid are added to a solution of 18.7 g of 4-(N-methyl-N-tert-butyloxycarbonyl)-amino-5-(naphth-2-yl)-pent-2-enoic acid ethyl ester in 250 ml of methylene chloride. The reaction mixture is stirred at room temperature for 1.5 hours and then concentrated by evaporation. The residue is dissolved in 300 ml of ether, washed once each with 0.5N sodium hydroxide solution and brine, dried over magnesium sulfate and concentrated by evaporation until crystallisation begins. The precipitate is filtered off with suction and dried. The title compound is obtained in the form of colourless crystals having a melting point of 115–117°. $R_f$ value=0.53 (methylene chloride/methanol 5:1). IR(CH$_2$Cl$_2$) cm$^{-1}$: 2973, 1722, 1677, 1435, 1369,1276, 1203, 1079,1041, 985, 819.

f) 4-(N-Methyl-N-tert-butyloxycarbonyl)-amino-5-(naphth-2-yl)-pent-2-enoic acid ethyl ester 2.73 g of sodium hydride (80% in mineral oil) are added in portions at 0° to a solution of 18.2 ml of phosphonoacetic acid triethyl ester in 230 ml of absolute tetrahydrofuran and the mixture is stirred at that temperature for 30 minutes. A solution of 16.8 g of N-methyl-N-tert-butyloxycarbonyl-amino-3-(naphth-2-yl)-propanal in 230 ml of THF is then added dropwise over a period of 60 minutes. When the dropwise addition is complete, the mixture is stirred at 0° for a further 90 minutes. The reaction mixture is then poured into water and extracted three times using 150 ml of ether each time. The combined organic phases are washed three times with water and once with saturated NaCl solution, dried (magnesium sulfate) and concentrated by evaporation. The residue is purified by chromatography (silica gel, hexane/ethyl acetate 4:1). In this way the title compound is obtained in the form of a light-yellow oil. $R_f$ value=0.32 (hexane/ethyl acetate 4:1). IR(CH$_2$Cl$_2$) cm-hu -1: 2976, 1714, 1686, 1478, 1447, 1391, 1367 1309,1169, 1044, 979, 856, 813.

g) N-Methyl-N-tert-butyloxycarbonyl-amino-3-(naphth-2-yl)-propanal

A solution of 5.0 g of N-methyl-N-tert-butyloxycarbonyl-amino-3-(naphth-2-yl)-propanecarboxylic acid methyl ester in 110 ml of toluene is cooled to −78° under argon. 17.5 ml of a 20% diisobutylaluminium hydride solution in toluene are then added dropwise to that solution over a period of 45 minutes. When the dropwise addition is complete, the mixture is stirred at that temperature for a further 45 minutes. Then at the same temperature 5 ml of methanol and at 0° 180 ml of a solution of 54 g of potassium sodium tartrate (tetrahydrate) in water are added to the reaction mixture. The mixture is stirred vigorously at 0° for 2 hours. The phases are then separated and the aqueous phase is extracted three times with methylene chloride. The combined organic phases are washed with water and saturated NaCl solution, dried (magnesium sulfate) and concentrated by evaporation. The title compound is obtained in the form of a yellowish-green oil and is reacted further without being purified. $R_f$ value=0.42 (methylene chloride/methanol 19:1). IR(CH$_2$Cl$_2$) cm$^{-1}$: 2972, 1735,1693,1454, 1392, 1367,1247, 1156, 858, 818.

h) N-Methyl-N-tert-butyloxycarbonyl-amino-3-(naphth-2-yl)-propanecarboxylic acid methyl ester 85.9 g of silver(l) oxide are added, with stirring, to a solution of 22.6 g of N-tert-butyl-oxycarbonyl-amino-3-(naphth-2-yl)-propanecarboxylic acid in 215 ml of N,N-dimethylformamide. 14 ml of methyl iodide are then added dropwise. The reaction mixture rises to a temperature of 38° and is stirred at room temperature for 2 days, diluted with 300 ml of ethyl acetate, filtered and concentrated by evaporation. The residue is purified by chromatography (silica gel, hexane/ethyl acetate 3:2). In this way the title compound is obtained in the form of a yellow oil. $R_f$ value=0.40 (hexane/ethyl acetate 3:2). IR(CH$_2$Cl$_2$) cm$^{-1}$: 3052, 2973, 1741, 1689, 1601, 1508, 1479, 1436, 1392, 1367, 1327, 1226, 1154, 1082, 998, 964, 857, 816.

The following compounds are also prepared in a manner analogous to that described in Example 20:

EXAMPLE 20/1

4-[N'-Methyl-N'-(3,5-bistrifluoromethyl-benzoyl)-amino]-5-(naphth-2-yl)-pentanoic acid N-(3,4-dichlorobenzyl)-amide, TLC: hexane/ethyl acetate (1:4) $R_f$=0.47

EXAMPLE 20/2

4-[N'-Methyl-N'-(3,5-bistrifluoromethyl-benzoyl)-amino]-5-(naphth-2-yl)-pentanoic acid N-(4-methoxy-benzyl)-amide, TLC: hexane/ethyl acetate (1:4) $R_f$=0.51

EXAMPLE 20/3
4-[N'-Methyl-N'-(3,5-bistrifluoromethyl-benzoyl)-amino]-5-(naphth-2-yl)-pentanoic acid N-([2-(2-pyridyl)-ethyl])-amide, TLC: hexane/ethyl acetate (1:4) $R_f$=0.40

EXAMPLE 20/4
4-[N'-Methyl-N'-(3,5-bistrifluoromethyl-benzoyl)-amino]-5-(naphth-2-yl)-pentanoic acid N-[2-(4-hydroxy-phenyl)-ethyl]-amide, TLC: methylene chloride/methanol (19:1) $R_f$=0.29.

EXAMPLE 20/5
4-[N'-Methyl-N'-(3,5-bistrifluoromethyl-benzoyl)-amino]-5-(naphth-2-yl)-pentanoic acid N-(2-pyridylmethyl)-amide, TLC: methylene chloride/methanol (19:1) $R_f$=0.25

EXAMPLE 20/6
4-[N'-Methyl-N'-(3,5-bistrifluoromethyl-benzoyl)-amino]-5-(naphth-2-yl)-pentanoic acid N-[3-(morpholin-4-yl)-propyl]-amide, TLC: methylene chloride/methanol (19:1) $R_f$=0.50

EXAMPLE 20/7
4-[N'-Methyl-N'-(3,5-bistrifluoromethyl-benzoyl)-amino]-5-(naphth-2-yl)-pentanoic acid N-propyl-amide, 1 TLC: hexane/ethyl acetate (1:) $R_f$=0.23

EXAMPLE 20/8
4-[N'-Methyl-N'-(3,5-bistrifluoromethyl-benzoyl)-amino]-5-(naphth-2-yl)-pentanoic acid N-(5-hydroxy-pentyl)-amide, TLC: methylene chloride/methanol (19:1) $R_f$=0.27

EXAMPLE 20/9
4-[N'-Methyl-N'-(3,5-bistrifluoromethyl-benzoyl)-amino]-5-(naphth-2-yl)-pentanoic acid N-(carbamoylmethyl)-amide, TLC: methylene chloride/methanol (19:1) $R_f$=0.16

EXAMPLE 21
4-[N'-Methyl-N'-(3,5-bistrifluoromethyl-benzoyl)-amino]-5-(naphth-2-yl)-pent-2-enoic acid N-(1-ethoxycarbonyl-cyclopent-1-ylmethyl)-amide 26.5 μl of triethylamine are added to a solution of 102.4 mg of 4-[N'-methyl-N'-(3,5-bistrifluoromethyl-benzoyl)-amino]-5-(naphth-2-yl)-pent-2-enoic acid hydroxysuccinimide ester and 35.5 mg of 1-aminomethylcyclopent-1-yl-carboxylic acid ethyl ester in 1 ml of methylene chloride. The reaction mixture is left to stand at room temperature for 18 hours. 0.5 ml of 1N potassium carbonate solution is then added and the mixture is shaken vigorously. After separation of the phases, the organic phase is separated off and and concentrated by evaporation. The residue is purified by chromatography (silica gel, hexane/ethyl acetate 1:1). In this way the title compound is obtained in the form of a yellow oil which crystallises from hexane/tert-butyl methyl ether. M.p. 136–138°

The starting materials can be prepared as follows:

a) 4-[N'-Methyl-N'-(3,5-bistrifluoromethyl-benzoyl)-amino]-5-(naphth-2-yl)-pent-2-enoic acid hydroxysuccinimide ester A solution of 1.0 g of 4-[N-methyl-N-(3,5-bistrifluoromethyl-benzoyl)-amino]-5-(naphth-2-yl)-pent-2-enoic acid, 0.24 g of N-hydroxysuccinimide and 0.45 g of N,N'-dicyclohexylcarbodiimide in 40 ml of tetrahydrofuran is stirred at room temperature for 15 hours. The reaction solution is then filtered and the filtrate is concentrated by evaporation. The residue is taken up in ether and again filtered and concentrated by evaporation. In this way the title compound is obtained in the form of a slightly yellowish foam. $R_f$ value=0.23 (hexane/ethyl acetate=1:1). IR(KBr) cm$^{-1}$: 2935, 1744, 1646, 1365, 1278, 1204, 1184 1142, 1068, 905 b) 4-[N-Methyl-N-(3,5-bistrifluoromethyl-benzoyl)-amino]-5-(naphth-2-yl)-pent-2-enoic acid A solution of 23.0 g of 4-[N-methyl-N-(3,5-bistrifluoromethyl-benzoyl)-amino]-5-(naphth-2-yl)-pent-2-enoic acid ethyl ester [see example 20d)] and 9.23 g of lithium hydroxide (monohydrate) in 240 ml of methanol, 175 ml of tetrahydrofuran and 72 ml of water is stirred at room temperature for 120 minutes and then concentrated by evaporation. The residue is dissolved in 200 ml of water, acidified to pH=2 with 0.1N hydrochloric acid and extracted three times using 200 ml of ethyl acetate each time. The combined organic phases are washed with water and saturated NaCl solution, dried (magnesium sulfate) and concentrated by evaporation. Filtration of the residue over silica gel with hexane/ethyl acetate 1:1 yields the title compound in the form of a yellow foam. $R_f$ value=0.41 (methylene chloride/methanol 19:1). IR(CH$_2$Cl$_2$) cm$^{-1}$: 3050,1709, 1644, 1402, 1337,1277, 1183,1142, 905, 849, 821

The following compounds are also prepared in a manner analogous to that described in Example 21:

EXAMPLE 21/1
4-[N'-Methyl-N'-(3,5-bistrifluoromethyl-benzoyl)-amino]-5-(naphth-2-yl)-pent-2-enoic acid N-(3,4-dichlorobenzyl)-amide

EXAMPLE 21/2
4-[N'-Methyl-N'-(3,5-bistrifluoromethyl-benzoyl)-amino]-5-(naphth-2-yl)-pent-2-enoic acid N-(4-methoxy-benzyl)-amide

EXAMPLE 21/3
4-[N'-Methyl-N'-(3,5-bistrifluoromethyl-benzoyl)-amino]-5-(naphth-2-yl)-pent-2-enoic acid N-[2-(2-pyridyl)-ethyl]-amide

EXAMPLE 21/4
4-[N'-Methyl-N'-(3,5-bistrifluoromethyl-benzoyl)-amino]-5-(naphth-2-yl)-pent-2-enoic acid N-[2-(4-hydroxy-phenyl)-ethyl]-amide

EXAMPLE 21/5
4-[N'-Methyl-N'-(3,5-bistrifluoromethyl-benzoyl)-amino]-5-(naphth-2-yl)-pent-2-enoic acid N-(2-pyridylmethyl)-amide

EXAMPLE 21/6
4-[N'-Methyl-N'-(3,5-bistrifluoromethyl-benzoyl)-amino]-5-(naphth-2-yl)-pent-2-enoic acid N-[3-(morpholin-4-yl)-propyl]-amide

EXAMPLE 21/7
4-[N'-Methyl-N'-(3,5-bistrifluoromethyl-benzoyl)-amino]-5-(naphth-2-yl)-pent-2-enoic acid N-propyl-amide

EXAMPLE 21/8
4-[N'-Methyl-N'-(3,5-bistrifluoromethyl-benzoyl)-amino]-5-(naphth-2-yl)-pent-2-enoic acid N-(5-hydroxy-pentyl)-amide

EXAMPLE 21/9
4-[N'-Methyl-N'-(3,5-bistrifluoromethyl-benzoyl)-amino]-5-(naphth-2-yl)-pent-2-enoic acid N-(carbamoylmethyl)-amide

EXAMPLE 22
4-[N'-Methyl-N'-(3,5-bistrifluoromethyl-benzoyl)-amino]-5-(naphth-2-yl)-pentanoic acid N-propyl-N-phenyl-amide A mixture consisting of 100 mg of 4-[N-methyl-N-(3,5-bistrifluoromethyl-benzoyl)-amino]-5-(naphth-2-yl)-pentanoic acid, 29.9 mg of N-propyl-aniline, 85.3 mg of propanephosphonic acid anhydride, 154 νl of triethylamine and 2 ml of methylene chloride is left to stand at room temperature for 18 hours. 0.5 ml of 1N potassium carbonate solution is then added and the mixture is shaken vigorously. After separation of the phases, the organic phase is separated off and concentrated by evaporation. Chromatography of the residue over silica gel with methylene chloride/methanol 19:1 yields the title compound in the form of a yellow foam. $R_f$ value=0.63 (methylene chloride/methanol 19:1).

The following compounds are also prepared in a manner analogous to that described in Example 22:

EXAMPLE 22/1
4-[N'-Methyl-N'-(3,5-bistrifluoromethyl-benzoyl)-amino]-5-(naphth-2-yl)-pentanoic acid N-(4-chloro-2-methyl-phenyl)-amide, $R_f$ value=0.70 (methylene chloride/methanol 19:1).

EXAMPLE 22/2
4-[N'-Methyl-N'-(3,5-bistrifluoromethyl-benzoyl)-amino]-5-(naphth-2-yl)-pentanoic acid N-(3,4-dimethoxy-phenyl)-amide, $R_f$ value=0.63 (methylene chloride/methanol 95:5).

EXAMPLE 22/3
4-[N'-Methyl-N'-(3,5-bistrifluoromethyl-benzoyl)-amino]-5-(naphth-2-yl)-pentanoic acid N-(2,4-dihydroxy-phenyl)-amide, TLC: methylene chloride/methanol (19:1) $R_f$=0.12

EXAMPLE 22/4
4-[N'-Methyl-N'-(3,5-bistrifluoromethyl-benzoyl)-amino]-5-(naphth-2-yl)-pentanoic acid N-ethyl-N-phenyl-amide, TLC: hexane/ethyl acetate (1:4) $R_f$=0.73

EXAMPLE 22/5
4-[N'-Methyl-N'-(3,5-bistrifluoromethyl-benzoyl)-amino]-5-(naphth-2-yl)-pentanoic acid N-(2-methyl-3-nitro-phenyl)-amide, TLC: hexane/ethyl acetate (1:4) $R_f$=0.63

EXAMPLE 22/6
4-[N'-Methyl-N'-(3,5-bistrifluoromethyl-benzoyl)-amino]-5-(naphth-2-yl)-pentanoic acid N-(3-methyl-6-methoxy-phenyl)-amide, $R_f$ value=0.70 (methylene chloride/methanol 95:5).

EXAMPLE 22/7
4-[N'-Methyl-N'-(3,5-bistrifluoromethyl-benzoyl)-amino]-5-(naphth-2-yl)-pentanoic acid N-(4-methyl-pyrimidin-2-yl)-amide, $R_f$ value=0.25 (methylene chloride/methanol 95:5).

EXAMPLE 22/8
4-[N'-Methyl-N'-(3,5-bistrifluoromethyl-benzoyl)-amino]-5-(naphth-2-yl)-pentanoic acid N-(pyrimidin-2-yl)-amide, $R_f$ value=0.23 (methylene chloride/methanol 95:5)

EXAMPLE 22/9
4-[N'-Methyl-N'-(3,5-bistrifluoromethyl-benzoyl)-amino]-5-(naphth-2-yl)-pentanoic acid N-(4-chloro-6-methyl-pyrimidin-2-yl)-amide, TLC: methylene chloride/methanol (19:1) $R_f$=0.13

EXAMPLE 22/10
4-[N'-Methyl-N'-(3,5-bistrifluoromethyl-benzoyl)-amino]-5-(naphth-2-yl)-pentanoic acid N-[4-(morpholin-4-yl)-phenyl]-amide, TLC: hexane/ethyl acetate (1:4) $R_f$=0.31

EXAMPLE 23
4-[N'-Methyl-N'-(3,5-bistrifluoromethyl-benzoyl)-amino]-5-(naphth-2-yl)-pent-2-enoic acid N-(4-chloro-2-methyl-phenyl)-amide is also prepared in a manner analogous to that described in Example 22 but using 4-[N-methyl-N-(3,5-bistrifluoromethyl-benzoyl)-amino]-5-(naphth-2-yl)-pent-2-enoic acid The following compounds are also prepared analogously to Example 23:

EXAMPLE 23/1
4-[N'-Methyl-N'-(3,5-bistrifluoromethyl-benzoyl)-amino]-5-(naphth-2-yl)-pent-2-enoic acid N-(3,4-dimethoxy-phenyl)-amide

EXAMPLE 23/2
4-[N'-Methyl-N'-(3,5-bistrifluoromethyl-benzoyl)-amino]-5-(naphth-2-yl)-pent-2-enoic acid N-(2,4-dihydroxy-phenyl)-amide

EXAMPLE 23/3
4-[N'-Methyl-N'-(3,5-bistrifluoromethyl-benzoyl)-amino]-5-(naphth-2-yl)-pent-2-enoic acid N-ethyl-N-phenyl-amide

EXAMPLE 23/4
4-[N'-Methyl-N'-(3,5-bistrifluoromethyl-benzoyl)-amino]-5-(naphth-2-yl)-pent-2-enoic acid N-(2-methyl-3-nitro-phenyl)-amide

EXAMPLE 24
4-[N'-Methyl-N'-(3,5-bistrifluoromethyl-benzoyl)-amino]-5-(1-methyl-indol-3-yl)-pentanoic acid N-phenyl-amide A mixture consisting of 43.2 mg of 4-[N'-methyl-N'-(3,5-bis-trifluoromethyl-benzoyl)-amino]-5-(1-methyl-indol-3-yl)-pentanoic acid, 8.9 mg of aniline, 36.65 mg of propanephosphonic acid anhydride, 60 μl of triethylamine and 1.5 ml of methylene chloride is left to stand at room temperature for 16 hours. 0.5 ml of 1N potassium carbonate solution is then added and the mixture is shaken vigorously. After separation of the phases, the organic phase is separated off and concentrated by evaporation. In this way the title compound is obtained in the form of a white foam. $R_f$ value=0.547 (ethyl acetate).

The following compounds are also prepared in a manner analogous to that described in EXAMPLE 24:

EXAMPLE 24/1
4-[N'-Methyl-N'-(3,5-bistrifluoromethyl-benzoyl)-amino]-5-(1-methyl-indol-3-yl)-pentanoic acid N-(4-chloro-2-methyl-phenyl)-amide, $R_f$ value=0.55 (ethyl acetate)

EXAMPLE 24/2
4-[N'-Methyl-N'-(3,5-bistrifluoromethyl-benzoyl)-amino]-5-(1-methyl-indol-3-yl)-pentanoic acid N-(3,4-dimethoxy-phenyl)-amide, $R_f$ value=0.63 (methylene chloride/methanol 95:5)

EXAMPLE 24/3
4-[N'-Methyl-N'-(3,5-bistrifluoromethyl-benzoyl)-amino]-5-(1-methyl-indol-3-yl)-pentanoic acid N-(2,4-dihydroxy-phenyl)-amide, $R_f$ value=0.37 (ethyl acetate)

EXAMPLE 24/4
4-[N'-Methyl-N'-(3,5-bistrifluoromethyl-benzoyl)-amino]-5-(1-methyl-indol-3-yl)-pentanoic acid N-ethyl-N-phenyl-amide, $R_f$ value=0.43 (ethyl acetate)

EXAMPLE 24/5
4-[N'-Methyl-N'-(3,5-bistrifluoromethyl-benzoyl)-amino]-5-(1-methyl-indol-3-yl)-pentanoic acid N-(2-methyl-3-nitro-phenyl)-amide, $R_f$ value=0.74 (ethyl acetate)

EXAMPLE 24/6
4-[N'-Methyl-N'-(3,5-bistrifluoromethyl-benzoyl)-amino]-5 (1l-methyl-indol-3-yl)-pentanoic acid N-(3-methyl-6methoxy-phenyl)-amide, $R_f$ value=0.70 (methylene chloride/methanol 95:5)

EXAMPLE 24/7
4-[N'-Methyl-N'-(3,5-bistrifluoromethyl-benzoyl)-amino]-5-(1-methyl-indol-3-yl)-pentanoic acid N-(4-methyl-pyrimidin-2-yl)-amide, $R_f$ value=0.25 (methylene chloride/methanol 95:5)

EXAMPLE 24/8
4-[N'-Methyl-N'-(3,5-bistrifluoromethyl-benzoyl)-amino]-5-(1-methyl-indol-3-yl)-pentanoic acid N-(pyrimidin-2-yl)-amide, $R_f$ value=0.23 (methylene chloride/methanol 95:5)

EXAMPLE 24/9
4-[N'-Methyl-N'-(3,5-bistrifluoromethyl-benzoyl)-amino]-5-(1-methyl-indol-3-yl)-pentanoic acid N-[4-(morpholin-4-yl)-phenyl]-amide, $R_f$ value=0.36 (ethyl acetate)

EXAMPLE 25
4-[N'-Methyl-N'-(3,5-bistrifluoromethyl-benzoyl)-amino]-5-(1-methyl-indol-3-yl)-pent-2-enoic acid N-(4-chloro-2-methyl-phenyl)-amide is also prepared in a manner analogous to that described in Example 5 but using 4-[N-methyl-N-(3,5-bistrifluoromethyl-benzoyl)-amino]-5-(1-methyl-indol-3-yl)-pent-2-enoic acid The following compounds are also prepared analogously to Example 25:

EXAMPLE 25/1
4-[N'-Methyl-N'-(3,5-bistrifluoromethyl-benzoyl)-amino]-5-(1-methyl-indol-3-yl)-pent-2-enoic acid N-(3,4-dimethoxy-phenyl)-amide, $R_f$ value=0.21 (hexane/ethyl acetate 1:1)

EXAMPLE 25/2
4-[N'-Methyl-N'-(3,5-bistrifluoromethyl-benzoyl)-amino]-5-(1-methyl-indol-3-yl)-pent-2-enoic acid N-(2,4-dihydroxy-phenyl)-amide, $R_f$ value=0.14 (methylene chloride/methanol 95:5)

EXAMPLE 25/3
4-[N'-Methyl-N'-(3,5-bistrifluoromethyl-benzoyl)-amino]-5-(1-methyl-indol-3-yl)-pent-2-enoic acid N-ethyl-N-phenyl-amide, $R_f$ value=0.29 (hexane/ethyl acetate 1:1)

EXAMPLE 25/4
4-[N'-Methyl-N'-(3,5-bistrifluoromethyl-benzoyl)-amino]-5-(1-methyl-indol-3-yl)-pent-2-enoic acid N-(5-chloro-2-methyl-phenyl)-amide, $R_f$ value=0.23 (hexane/ethyl acetate 1:1)

EXAMPLE 26
4-[N'-Methyl-N'-(3,5-bistrifluoromethyl-benzoyl)-amino]-5-(1H-indol-3-yl)-pentanoic acid N-(3-chlorobenzyl)-amide 27 µl of triethylamine are added to a solution of 106 mg of 4-[N'-methyl-N'-(3,5-bistrifluoromethyl-benzoyl)-amino]-5-(1H-indol-3-yl)-pentanoic acid hydroxysuccinimide ester and 28 mg of 3-chlorobenzylamine in 1 ml of methylene chloride. The reaction mixture is left to stand at room temperature for 18 hours. The reaction mixture is then concentrated by evaporation and the residue is taken up in ethyl acetate and washed in succession with 2N potassium carbonate solution, water, 0.1N hydrochloric acid, and brine, dried over sodium sulfate and again concentrated by evaporation. In this way the title compound is obtained in the form of a colourless foam.

The starting materials can be prepared as follows:

a) 4-[N'-Methyl-N'-(3,5-bistrifluoromethyl-benzoyl)-amino]-5-(1H-indol-3-yl)-pentanoic acid hydroxysuccinimide ester A solution of 27.0 g of 4-[N'-methyl-N'-(3,5-bistrifluoromethyl-benzoyl)-amino]-5-(1H-indol-3-yl)-pentanoic acid, 6.5 g of N-hydroxysuccinimide and 12.2 g of N,N'-dicyclohexylcarbodiimide in 800 ml of tetrahydrofuran is stirred at room temperature for 18 hours. The reaction solution is then filtered and the filtrate is concentrated by evaporation. The residue is taken up in ether and again filtered and concentrated by evaporation. In this way the the title compound is obtained in the form of a colourless white foam.

b) 4-[N-Methyl-N-(3,5-bistrifluoromethyl-benzoyl)-amino]-5-(1H-indol-3-yl)-pentanoic acid A solution of 30 g of 4-[N-methyl-N-(3,5-bistrifluoromethyl-benzoyl)-amino]-5-(1H-indol-3-yl)-pentanoic acid ethyl ester and 3.7 g of lithium hydroxide in 210 ml of tetrahydrofuran/methanol/water=2/2/1 is stirred at room temperature for 3 hours and then concentrated by evaporation. The residue is dissolved in 300 ml of water, extracted with ether, acidified to pH=2 with 0.1N hydrochloric acid and extracted three times with ether. The combined organic phases originating from the extraction of the acidic aqueous phase are washed with water and saturated NaCl solution, dried (magnesium sulfate) and concentrated by evaporation. In this way the title compound is obtained in the form of a yellow foam.

c) 4-[N-Methyl-N-(3.5-bistrifluoromethyl-benzoyl)-amino]-5-(1H-indol-3-yl)-pentanoic acid ethyl ester A solution of 34.3 g of 4-[N-methyl-N-(3,5-bistrifluoromethyl-benzoyl)-amino]-5-(1H-indol-3-yl)-pent-2-enoic acid ethyl ester in 340 ml of tetrahydrofuran is hydrogenated at 20° C. for 80 minutes in the presence of 3.4 g of palladium/activated carbon (10%) and 0.4 g of 1,2-dichlorobenzene. The reaction mixture is then filtered and concentrated by evaporation. In this way the title compound is obtained in the form of a brownish resin.

d) 4-[N-Methyl-N-(3,5-bistrifluoromethyl-benzoyl)-amino]-5-(1H-indol-3-yl)-pent-2-enoic acid ethyl ester 57.1 g of 3,5-bis-trifluoromethyl-benzoyl chloride, 104 ml of triethylamine and 5.2 g of 4-dimethylamino-pyridine are added at 0° under argon to a solution of 54.2 g of 4-(N-methyl)-amino-5-(1H-indol-3-yl)-pent-2-enoic acid ethyl ester in 595 ml of methylene chloride. The reaction mixture is stirred at 20° for 16 hours and then poured into water. The organic phase is separated off and the aqueous phase is extracted a further three times with ethyl acetate. The combined organic phases are washed with 0.01N hydrochloric acid, water and saturated NaCl solution, dried (magnesium sulfate) and concentrated by evaporation. The residue is chromatographed (silica gel, hexane/ethyl acetate 7:4). In this way the title compound is obtained in the form of a colourless resin which turns a brownish colour with time.

e) 4-(N-Methyl)-amino-5-(1H-indol-3-yl)-pent-2-enoic acid ethyl ester 250 ml of trifluoroacetic acid are added dropwise over a period of 20 minutes to a solution of 72.1 g of 4-(N-methyl-N-tert-butyloxycarbonyl)-amino-5-(1-tert-butyloxycarbonyl-indol-3-yl)-pent-2-enoic acid ethyl ester in 550 ml of methylene chloride. The reaction mixture is stirred at room temperature for 18 hours and then concentrated by evaporation. The residue is dissolved in 300 ml of toluene and again concentrated by evaporation. That step is repeated twice more. The crude product (brownish oil) so obtained can be processed further without further purification.

f) 4-(N-Methyl-N-tert-butyloxycarbonyl)-amino-5-(1-tert-butyloxycarbonyl-indol-3-yl)-pent-2-enoic acid ethyl ester 11.5 g of sodium hydride (100%) are added in portions at 0° to a solution of 108.2 g of phosphonoacetic acid triethyl ester in 1200 ml of absolute tetrahydrofuran and the mixture is stirred at that temperature for 30 minutes. A solution of 91.2 g of N- methyl-N-tert-butyloxycarbonyl-amino-3-(1-tert-butyloxycarbonyl-indol-3-yl)-propanal in 1200 ml of THF is then added dropwise over a period of 90 minutes. When the dropwise addition is complete, the mixture is stirred at 0° for a further 30 minutes. The reaction mixture is then poured into water and extracted three times using 500 ml of ether each time. The combined organic phases are washed three times with water and once with saturated NaCl solution, dried (magnesium sulfate) and concentrated by evaporation. The residue is purified by chromatography (silica gel, hexane/ethyl acetate 3:2). In this way the title compound is obtained in the form of yellow oil.

g) N-Methyl-N-tert-butyloxycarbonyl-amino-3-(1-tert-butyloxycarbonyl-indol-3-yl)-propanal A solution of 88.1 g of N-methyl-N-tert-butyloxycarbonyl-amino-3-(1-tert-butyloxycarbonyl-indol-3-yl)-propanecarboxylic acid methyl ester in 1800 ml of toluene is cooled to −78° under argon. At that temperature 585.2 ml of a 20% diisobutylaluminium hydride solution in toluene are slowly added dropwise. When the dropwise addition is complete, the mixture is stirred at that temperature for a further 30 minutes. Then at the same temperature 42 ml of methanol and at 0° 2900 ml of a solution of 910 g of potassium sodium tartrate in water are added to the reaction mixture. The mixture is stirred vigorously at 0° for 2 hours. The phases are then separated and the aqueous phase is extracted three times using 2 liters of diethyl ether each time. The combined organic phases are washed with water and saturated NaCl solution, dried (magnesium sulfate) and concentrated by evaporation. The title compound is thus obtained in the form of a yellow oil and reacted further without being purified.

h) N-Methyl-N-tert-butyloxycarbonyl-amino-3-(1-tert-butyloxycarbonyl-indol-3-yl)-propanecarboxylic acid methyl ester 295 g of silver(I) oxide are added, with stirring, to a solution of 75 g of N-tert-butyloxycarbonyl-amino-3-(1-tert-butyloxycarbonyl-indol-3-yl)-propanecarboxylic acid methyl ester in 770 ml of N,N-dimethylformamide. 75 ml of methyl iodide are then added dropwise. The reaction mixture rises to a temperature of 40° and is stirred at room temperature for 2 days and then diluted with 800 ml of ethyl acetate, filtered and concentrated by evaporation. The residue is purified by chromatography (silica gel, hexane/ethyl acetate 3:2). In this way the title compound is obtained in the form of a yellow oil.

The following compounds are also prepared in a manner analogous to that described in EXAMPLE 26:

EXAMPLE 26/1
4-[N'-Methyl-N'-(3,5-bistrifluoromethyl-benzoyl)-amino]-5-(1H-indol-3-yl)-pentanoic acid N-(3,4-dichlorobenzyl)-amide

EXAMPLE 26/2
4-[N'-Methyl-N'-(3,5-bistrifluoromethyl-benzoyl)-amino]-5-(1H-indol-3-yl)-pentanoic acid N-(4-methoxy-benzyl)-amide

EXAMPLE 26/3
4-[N'-Methyl-N'-(3,5-bistrifluoromethyl-benzoyl)-amino]-5-(1H-indol-3-yl)-pentanoic acid N-[2-(2-pyridyl)-ethyl]-amide

EXAMPLE 26/4
4-[N'-Methyl-N'-(3,5-bistrifluoromethyl-benzoyl)-amino]-5-(1H-indol-3-yl)-pentanoic acid N-[2-(4-hydroxy-phenyl)-ethyl]-amide

EXAMPLE 26/5
4-[N'-Methyl-N'-(3,5-bistrifluoromethyl-benzoyl)-amino]-5-(1H-indol-3-yl)-pentanoic acid N-(2-pyridylmethyl)-amide

EXAMPLE 26/6
4-[N'-Methyl-N'-(3,5-bistrifluoromethyl-benzoyl)-amino]-5-(1H-indol-3-yl)-pentanoic acid N-[3-(morpholin-4-yl)-propyl]-amide, $R_f$ value=0.21 (methylene chloride/methanol 9:1)

EXAMPLE 26/7
4-[N'-Methyl-N'-(3,5-bistrifluoromethyl-benzoyl)-amino]-5-(1H-indol-3-yl)-pentanoic acid N-propyl-amide

EXAMPLE 26/8
4-[N'-Methyl-N'-(3,5-bistrifluoromethyl-benzoyl)-amino]-5-(1H-indol-3-yl)-pentanoic acid N-(5-hydroxy-pentyl)-amide

EXAMPLE 26/9
4-[N'-Methyl-N'-(3,5-bistrifluoromethyl-benzoyl)-amino]-5-(1H-indol-3-yl)-pentanoic acid N-(carbamoylmethyl)-amide

EXAMPLE 27
4-[N'-Methyl-N'-(3,5-bistrifluoromethyl-benzoyl)-amino]-5-(1H-indol-3-yl)-pent-2-enoic acid N-(3,4-dichlorobenzyl)-amide is also prepared in a manner analogous to that described in Example 26 but using 4-[N-methyl-N-(3,5-bistrifluoromethyl-benzoyl)-amino]-5-(1H-indol-3-yl)-pent-2-enoic acid hydroxysuccinimide ester The starting materials can be prepared as follows:

a) 4-[N'-Methyl-N'-(3,5-bistrifluoromethyl-benzoyl)-amino]-5-(1H-indol-3-yl)-pent-2-enoic acid hydroxysuccinimide ester A solution of 12.2 g of 4-[N'-methyl-N'-(3,5-bistrifluoromethyl-benzoyl)-amino]-5-(1H-indol-3-yl)-pent-2-enoic acid, 2.85 g of N-hydroxysuccinimide and 5.12 g of N,N'-dicyclohexylcarbodiimide in 380 ml of tetrahydrofuran is stirred at room temperature for 16 hours. The reaction solution is then filtered and the filtrate is concentrated by evaporation. The residue is taken up in ether and again filtered and concentrated by evaporation. In this way the title compound is obtained in the form of a colourless white foam.

b) 4-[N-Methyl-N-(3,5-bistrifluoromethyl-benzoyl)-amino]-5-(1H-indol-3-yl)-pent-2-enoic acid A solution of 8.5 g of 4-[N-methyl-N-(3,5-bistrifluoromethyl-benzoyl)-amino]-5-(1H-indol-3-yl)-pent-2-enoic acid ethyl ester and 1.2 g of lithium hydroxide in 70 ml of tetrahydrofuran/methanol/water=2/2/1 is stirred at room temperature for 16 hours and then concentrated by evaporation. The residue is dissolved in 150 ml of water with heating to 50°, extracted with ether at 20°, acidified to pH=2 with 0.1N hydrochloric acid and extracted three times with ether. The combined organic phases originating from the extraction of the acidic aqueous phase are washed with water and saturated NaCl solution, dried (magnesium sulfate) and concentrated by evaporation. In this way the title compound is obtained in the form of a yellow foam.

The following compounds are also prepared analogously to Example 27:

EXAMPLE 27/1
4-[N'-Methyl-N'-(3,5-bistrifluoromethyl-benzoyl)-amino]-5-(1H-indol-3-yl)-pent-2-enoic acid N-(4-methoxy-benzyl)-amide

EXAMPLE 27/2
4-[N'-Methyl-N'-(3,5bistrifluoromethyl-benzoyl)-amino]-5-(1H-indol-3-yl)-pent-2-enoic acid N-[2-(2-pyridyl)-ethyl]-amide, $R_f$ value=0.083 (ethyl acetate)

EXAMPLE 27/3
4-[N'-Methyl-N'-(3,5-bistrifluoromethyl-benzoyl)-amino]-5-(1H-indol-3-yl)-pent-2-enoic acid N-[2-(4-hydroxy-phenyl)-ethyl]-amide

EXAMPLE 27/4
4-[N'-Methyl-N'-(3,5-bistrifluoromethyl-benzoyl)-amino]-5-(1H-indol-3-yl)-pent-2-enoic acid N-(2-pyridylmethyl)-amide

EXAMPLE 27/5
4-[N'-Methyl-N'-(3,5-bistrifluoromethyl-benzoyl)-amino]-5-(1H-indol-3-yl)-pent-2-enoic acid N-[3-(morpholin-4-yl)-propyl]-amide, $R_f$ value=0.71 (methanol/water 3:1)

EXAMPLE 27/6
4-[N'-Methyl-N'-(3,5-bistrifluoromethyl-benzoyl)-amino]-5-(1H-indol-3-yl)-pent-2-enoic acid N-propyl-amide

EXAMPLE 27/7
4-[N'-Methyl-N'-(3,5-bistrifluoromethyl-benzoyl)-amino]-5-(1H-indol-3-yl)-pent-2-enoic acid N-(5-hydroxy-pentyl)-amide

EXAMPLE 27/8
4-[N'-Methyl-N'-(3,5-bistrifluoromethyl-benzoyl)-amino]-5-(1H-indol-3-yl)-pent-2-enoic acid N-(carbamoylmethyl)-amide

EXAMPLE 27/9
4-[N'-Methyl-N'-(3,5-bistrifluoromethyl-benzoyl)-amino]-5-(1H-indol-3-yl)-pent-2-enoic acid N-(1-phenyl-ethyl)-amide, $R_f$ value=0.125 (methylene chloride/methanol 19:1)

EXAMPLE 28
4-[N'-Methyl-N'-(3,5-bistrifluoromethyl-benzoyl)-amino]-5-(1H-indol-3-yl)-pentanoic acid N-phenyl-amide A mixture consisting of 42.9 mg of 4[N'-methyl-N'-(3,5-bis-trifluoromethyl-benzoyl)-amino]-5-(1H-indol-3-yl)-pentanoic acid, 8.9 mg of aniline, 36.65 mg of propane-phosphonic acid anhydride, 60 µl of triethylamine and 1.5 ml of methylene chloride is left to stand at room temperature for 16 hours. 0.5 ml of 1N potassium carbonate solution is then added and the mixture is shaken vigorously. After separation of the phases, the organic phase is separated off and concentrated by evaporation. In this way the title compound is obtained in the form of a white foam. $R_f$ value=0.26 (ethyl acetate).

The following compounds are also prepared in a manner analogous to that described in EXAMPLE 28:

EXAMPLE 28/1
4-[N'-Methyl-N'-(3,5-bistrifluoromethyl-benzoyl)-amino]-5-(1H-indol-3-yl)-pentanoic acid N-(4-chloro-2-methyl-phenyl)-amide

EXAMPLE 28/2
4-[N'-Methyl-N'-(3,5-bistrifluoromethyl-benzoyl)-amino]-5-(1H-indol-3-yl)-pentanoic acid N-(3,4-dimethoxy-phenyl)-amide.

EXAMPLE 28/3
4-[N'-Methyl-N'-(3,5-bistrifluoromethyl-benzoyl)-amino]-5-(1H-indol-3-yl)-pentanoic acid N-(2,4-dihydroxy-phenyl)-amide

EXAMPLE 28/4
4-[N'-Methyl-N'-(3,5-bistrifluoromethyl-benzoyl)-amino]-5-(1H-indol-3-yl)-pentanoic acid N-ethyl-N-phenyl-amide

EXAMPLE 28/5
4-[N'-Methyl-N'-(3,5-bistrifluoromethyl-benzoyl)-amino]-5-(1H-indol-3-yl)-pentanoic acid N-(2-methyl-3-nitro-phenyl)-amide

EXAMPLE 29
4-[N'-Methyl-N'-(3,5-bistrifluoromethyl-benzoyl)-amino]-5-(1H-indol-3-yl)-pent-2-enoic acid N-(4-chloro-2-methyl-phenyl)-amide is also prepared in a manner analogous to that described in Example 28 but using 4-[N-methyl-N-(3,5-bistrifluoromethyl-benzoyl)-amino]-5-(1H-indol-3-yl)-pent-2-enoic acid The following compounds are also prepared analogously to Example 29:

EXAMPLE 29/1
4-[N'-Methyl-N'-(3,5-bistrifluoromethyl-benzoyl)-amino]-5-(1H-indol-3-yl)-pent-2-enoic acid N-(3.4-dimethoxy-phenyl)-amide

EXAMPLE 29/2
4-[N'-Methyl-N'-(3,5-bistrifluoromethyl-benzoyl)-amino]-5-(1H-indol-3-yl)-pent-2-enoic acid N-(2,4-dihydroxy-phenyl)-amide

EXAMPLE 29/3
4-[N'-Methyl-N'-(3,5-bistrifluoromethyl-benzoyl)-amino]-5-(1H-indol-3-yl)-pent-2-enoic acid N-ethyl-N-phenyl-amide

EXAMPLE 29/4
4-[N'-Methyl-N'-(3,5-bistrifluoromethyl-benzoyl)-amino]-5-(1H-indol-3-yl)-pent-2-enoic acid N-(2-methyl-3-nitro-phenyl)-amide

EXAMPLE 29/5
4-[N'-Methyl-N'-(3,5-bistrifluoromethyl-benzoyl)-amino]-5-(1H-indol-3-yl)-pent-2-enoic acid N-(3-methyl-6-methoxy-phenyl)-amide

EXAMPLE 29/6
4-[N'-Methyl-N'-(3,5-bistrifluoromethyl-benzoyl)-amino]-5-(1H-indol-3-yl)-pent-2-enoic acid N-(4-methyl-pyrimidin-2-yl)-amide

EXAMPLE 29/7
4-[N'-Methyl-N'-(3,5-bistrifluoromethyl-benzoyl)-amino]-5-(1H-indol-3-yl)-pent-2-enoic acid N-(pyrimidin-2-yl)-amide

EXAMPLE 29/8
4-[N'-Methyl-N'-(3,5-bistrifluoromethyl-benzoyl)-amino]-5-(1H-indol-3-yl)-pent-2-enoic acid N-phenyl-amide

EXAMPLE 29/9
4-[N'-Methyl-N'-(3,5-bistrifluoromethyl-benzoyl)-amino]-5-(1H-indol-3-yl)-pent-2-enoic acid N-[4-morpholin-4-yl)-phenyl]-amide.

EXAMPLE 30
(4S)-4-[N'-Methyl-N'-(3,5-bistrifluoromethyl-benzoyl)-amino]-5-phenyl-pentanoic acid N-(2-methoxy-benzyl)-amide The compound is prepared in a manner analogous to that described in Examples 1 and 3 but using tert-butyloxycarbonyl-D-phenyl-alanine as starting material, $R_f$ value=0.35 (hexane/ethyl acetate 1:1).

EXAMPLE 31
(4S)-4-[N'-Methyl-N'-(3.5-bistrifluoromethyl-benzoyl)-amino]-5-phenyl-pentanoic acid N-(2-methoxy-phenyl)-amide The compound is prepared in a manner analogous to that described in Examples 1 and 3 but using tert-butyloxycarbonyl-D-phenyl-alanine as starting material, $R_f$ value=0.41 (hexane/ethyl acetate 1:1).

EXAMPLE 32
4-[N'-(3,5-Bistrifluoromethyl-benzoyl)-N'-methyl-amino]-5,5-diphenyl-pentanoic acid N-cyclopropyl-amide 43 mg (0.0693 mmol) of 4-[N'-(3,5-bistrifluoromethyl-benzoyl)-N'-methyl-amino]-5,5-diphenyl-pentanoic acid N-hydroxysuccinimidyl ester are added to a solution of 5.0 mg (0.083 mmol) of cyclopropylamine and 11.6 ml (0.083 mmol) of triethylamine in 1 ml of methylene chloride and the mixture is left to stand at room temperature for 24 hours. The reaction mixture is then washed with 0.5 ml of a 1N aqueous potassium carbonate solution. The organic phase is concentrated by evaporation in a vacuum centrifuge. The title compound is obtained in the form of a white foam. TLC: ethyl acetate $R_f$=0.62.

The starting compounds are prepared as follows:

(a) 2-(N-tert-Butoxycarbonyl-N-methyl)-amino-3,3-diphenyl-propanoic acid methyl ester To a solution of 34.2 g (0.10 mol) of 2-tert-butoxycarbonylamino-3,3-diphenyl-propanoic acid [J. Med. Chem. 35 (1992) 3364] in 250 ml of N,N-dimethylformamide there are added in succession 121.9 g (0.52 mol) of silver(l) oxide in one portion and 26 ml (0.41 mol) of methyl iodide dropwise over a period of 20 minutes. After 26 hours' stirring at room temperature, the mixture is diluted with ethyl acetate, and the oxide is filtered off over Hyflo and then washed with ethyl acetate. The organic phase is concentrated by evaporation first in a rotary evaporator and then under a high vacuum. The residue is dissolved in ethyl acetate, washed three times with water and once with brine, dried over sodium sulfate dried and concentrated by evaporation. The title compound is obtained in the form of a beige solid. TLC: methylene chloride/methanol (95:5) $R_f$=0.28; $R_t$(HPLC)=20.8 min; $^1$H-NMR (300 MHz, $d_6$-DMSO, RT) d 7.38–7.13 (m, 10H), 5.57/5.35 (d, 1H), 4.63 (d, 1H), 3.48/3.44 (s, 3H), 2.65/2.62 (s, 3H), 1.39/1.27 (s, 9H); FAB-MS (M+H)$^+$=370.

(b) (1-Hydroxymethyl-2,2-diphenyl-ethyl)-methyl-carbamic acid tert-butyl ester

To a solution of 32.0 g (86.6 mmol) of 2-(N-tert-butoxycarbonyl-N-methyl)-amino-3,3-diphenyl-propanoic acid methyl ester in 400 ml of ether there are added in succession 3.0 g (130.0 mmol) of lithium borohydride in portions and 5.3 ml (130 mmol) of methanol dropwise (foams!). The reaction mixture is stirred under reflux for 3 hours, then cooled with an ice bath; 40 ml of 0.5N hydrochloric acid are added (foams!). After further dilution with water, the mixture is extracted twice with methylene chloride. The combined organic phases are dried over sodium sulfate and concentrated by evaporation. The title compound is obtained in the form of a white foam. TLC: methylene chloride/methanol (95:5) $R_f$=0.46; $R_t$(HPLC)=18.0 min; $^1$H-NMR (300 MHz, CDCl$_3$, RT) d 7.38–7.14 (m, 10H), 4.93 (br, 1H), 4.19/4.02 (d, 1H), 3.62 (m, 2H), 2.70/2.60 (s, 3H), 2.08 (br, 1H), 1.50/1.38 (s, 9H); FAB-MS (M+H)$^+$=342.

(c) (1-Formyl-2,2-diphenyl-ethyl)-methyl-carbamic acid tert-butyl ester 17.8 ml (127 mmol) of triethylamine and a solution of 22.8 9 (127 mmol) of sulfur trioxide pyridine complex in 100 ml of dimethyl sulfoxide are added in succession to a solution of 14.5 g (42.5 mmol) of (1-hydroxymethyl-2,2-diphenyl-ethyl)-methyl-carbamic acid tert-butyl ester in 80 ml of dimethyl sulfoxide. After 45 minutes the reaction mixture is poured into ice-water and extracted completely with ether. The combined organic phases are washed twice with 1M potassium hydrogen sulfate, twice with water and once with 1M sodium hydrogen carbonate, dried over sodium sulfate and concentrated by evaporation. The title compound is obtained in the form of a yellow oil. TLC: methylene chloride/methanol (95:5) $R_f$=0.88; $R_t$(HPLC)=20.1 min; $^1$H-NMR (300 MHz, CDCl$_3$, RT) d 9.53 (s, 1H), 7.42–7.16 (m, 10H), 5.35/5.00 (d, 1H), 4.57/4.55 (d, 1H), 2.62/2.54 (s, 3H), 1.50/1.40 (s, 9H).

(d) 4-(N-tert-Butoxycarbonyl-N-methyl)-amino-5,5-diphenyl-pent-2-enoic acid ethyl ester A solution of 14 ml (68 mmol) of phosphonoacetic acid triethyl ester in 130 ml of tetrahydrofuran is added at 0° C. to a solution of 3.7 g (84 mmol) of 55–65% sodium hydride dispersion (washed three times with pentane) in 130 ml of tetrahydrofuran. After 1 hour a solution of 13.6 g (40 mmol) of (1-formyl-2,2-diphenyl-ethyl)-methyl-carbamic acid tert-butyl ester in 130 ml of tetrahydrofuran is added dropwise. After 4 hours the reaction mixture is rendered neutral with 1M potassium hydrogen sulfate and then diluted with water and ethyl acetate. The organic phase is washed three times with water, dried over magnesium sulfate and concentrated by evaporation. The residue is chromatographed on silica gel with methylene chloride/methanol (99:1 to 98:2). The title compound is obtained in the form of a yellow oil. TLC: methylene chloride/methanol (98:2) $R_f$=0.45; $R_t$(HPLC)=21.8 min; $^1$H-NMR (300 MHz, CDCl$_3$, RT) d 7.38–7.16 (m, 10H), 6.77 (m, 1H), 5.77 (m, 1H), 5.78/5.49 (m, 1H), 4.13 (q, 2H), 4.13 (m, 1H), 2.64/2.55 (s, 3H), 1.50/1.36 (s, 9H), 1.24 (M, 3H).

(e) 4-Methylamino-5,5-diphenyl-pent-2-enoic acid ethyl ester 22 ml (0.28 mol) of trifluoroacetic acid are added dropwise to a solution of 14.2 g (34.7 mmol) of 4-(tert-butoxycarbonyl-methyl-amino)-5,5-diphenyl-pent-2-enoic acid ethyl ester in 100 ml of methylene chloride. After 5 hours the reaction mixture is concentrated by evaporation and then twice toluene is added and the mixture concentrated by evaporation. The residue is dissolved in methylene chloride, washed with saturated sodium hydrogen carbonate solution, dried over sodium sulfate and again concentrated by evaporation. The title compound is obtained in the form of a yellow oil. TLC: methylene chloride/methanol (95:5) $R_f$=0.26; $R_t$(HPLC)=12.5 min; $^1$H-NMR (300 MHz, CDCl$_3$, RT) d 7.38–7.15 (m, 10H), 6.66 (dd, 1H), 5.84 (d, 1H), 4.12 (q, 2H), 3.97 (d, 1H), 3.81 (m, 1H), 2.31 (s, 3H), 1.33 (br, 1H), 1.24 (t, 3H).

(f) 4-[N-(3,5-Bistrifluoromethyl-benzoyl)-N-methyl-amino]-5,5diphenyl-pent-2-enoic acid ethyl ester A solution of 10.6 g (34.3 mmol) of 4-methylamino-5,5-diphenyl-pent-2-enoic acid ethyl ester in 110 ml of methylene chloride is added at 0° C. via a cannula to a solution of 6.7 ml (36.0 mmol) of 3,5-bistrifluoromethyl-benzoyl chloride in 110 ml of methylene chloride. 5.8 ml (41.1 mmol) of triethylamine and 0.4 g (3.4 mmol) of 4-dimethylaminopyridine are then added. After 1 hour the reaction mixture is diluted with ethyl acetate and washed twice with water and once with brine. The aqueous phases are back-extracted once with ethyl acetate. The combined organic phases are then dried over magnesium sulfate and concentrated by evaporation. The residue is chromatographed on silica gel with methylene chloride/methanol (100:0 to 98:2). The title compound is obtained in the form of a light-yellow foam. TLC: methylene chloride/methanol (98:2) $R_f$=0.38; $R_t$(HPLC)=22.4 min; $^1$H-NMR (400 MHz, d$^6$-DMSO, 120° C.) d 8.00 (br, 1H), 7.47–7.29 (m, 10H), 7.26–7.20 (m, 2H), 6.83 (dd, 1H), 5.96 (d, 1H), 5.89 (br, 1H), 4.65 (d, 1H), 4.10 (q, 2H), 2.68 (s, 3H), 1.18 (t, 3H); FAB-MS (M+H)$^+$=550.

(g) 4-[N-(3,5-Bistrifluoromethyl-benzoyl)-N-methyl-amino]-5,5-diphenyl-pentanoic acid ethyl ester A solution of 15.0 g (27.3 mmol) of 4-[N-(3,5-bistrifluoromethyl-benzoyl)-N-methylamino]-5,5-diphenyl-pent-2-enoic acid ethyl ester in 400 ml of tetrahydrofuran is hydrogenated with 1.5 g of 10% palladium on activated carbon under 1 atm. of hydrogen. After 4 hours the suspension is filtered over Hyflo and washed with tetrahydrofuran, and the filtrate is concentrated by evaporation. The title compound is obtained in the form of a yellow oil. TLC: ethyl acetate/hexane (1:2) $R_f$=0.50; $R_t$(HPLC)=22.4 min; $^1$H-NMR (400 MHz, d$^6$-DMSO, 120° C.) d 7.96 (br, 1H), 7.48–7.18 (m, 12H), 5.44 (br, 1H), 4.31 (d, 1H), 4.05 (q, 2H), 2.56 (br s, 3H), 2.44–2.27 (m, 2H), 1.93 (m, 1H), 1.76 (m, 1H), 1.17 (t, 3H); FAB-MS (M+H)$^+$=552.

(h) 4-[N-(3,5-Bistrifluoromethyl-benzoyl)-N-methyl-amino]-5,5-diphenyl-pentanoic acid 45 ml of 1N sodium hydroxide are added to a solution of 15.2 g (27.6 mmol) of 4-[N-(3,5-bistrifluoromethyl-benzoyl)-N-methyl-amino]-5,5-diphenyl-pentanoic acid ethyl ester in 160 ml of tetrahydrofuran/methanol (2:1). After 2 hours the reaction mixture is concentrated by evaporation, diluted with water and rendered acidic with cold 2N hydrochloric acid. The white precipitate is filtered off, then washed with water and dried under a high vacuum at 50° C. The title compound is obtained in the form of a white solid. TLC: methylene chloride/methanol (95:5) $R_f$=0.21; $R_t$(HPLC)=18.5 min; $^1$H-NMR (400 MHz, d$^6$-DMSO, 120° C.) d 7.96 (br, 1H), 7.48–7.18 (m, 12H), 5.43 (br, 1H), 4.31 (d, 1H), 2.55 (br s, 3H). 2.36–2.19 (m, 2H), 1.91 (m, 1H), 1.73 (m, 1H); FAB-MS (M+H)$^+$=524.

(i) 4-[N'-(3,5-Bistrifluoromethyl-benzoyl)-N'-methyl-amino]-5,5-diphenyl-pentanoic acid N-hydroxysuccinimidyl ester 143 mg (1.2 mmol) of N-hydroxysuccinimide and 28 mg (0.23 mmol) of 4-dimethylaminopyridine are added to a solution of 600 mg (1.15 mmol) of 4-[N-(3,5-bistrifluoromethyl-benzoyl)-N-methyl-amino]-5,5-diphenyl-pentanoic acid in 9 ml of methylene chloride and the mixture is cooled to 0° C. 247 mg (1.26 mmol) of N-ethyl-N'-(3-dimethylaminopropyl)-carbodiimide hydrochloride are then added and the reaction mixture is stirred at 0° C. for 10 minutes and then at room temperature for 22 hours. The mixture is poured into ice-cold 5% citric acid and the aqueous phase is extracted three times with methylene chloride. The combined organic phases are washed with brine, dried over sodium sulfate and concentrated by evaporation. The title compound is obtained in the form of a light-yellow solid. TLC: methylene chloride/methanol (95:5) $R_f$=0.83; $R_t$(HPLC)=20.8 min; $^1$H-NMR (400 MHz, d$^6$-DMSO, RT) d 8.08 (br, 1H), 7.54–7.12 (m, 12H), 5.58 (m, 1H), 4.32 (br d, 1H), 2.95–2.65 (m, 2H), 2.77 (s, 4H), 2.52 (br s, 3H), 1.95 (m, 1H), 1.67 m, 1H); FAB-MS (M+H)$^+$=621.

The following are also prepared analogously to Example 32:

EXAMPLE 32/1

4-[N'-(3,5-Bistrifluoromethyl-benzoyl)-N'-methyl-amino]-5,5-diphenyl-pentanoic acid N-(prop-2-ynyl)-amide; TLC: ethyl acetate $R_f$=0.72.

EXAMPLE 32/2

4-[N'-(3,5-Bistrifluoromethyl-benzoyl)-N'-methyl-amino]-5,5-diphenyl-pentanoic acid N-(2-hydroxy-1,1-dimethyl-ethyl)-amide; TLC: ethyl acetate $R_f$=0.54.

EXAMPLE 32/3

4-[N'-(3,5-Bistrifluoromethyl-benzoyl)-N'-methyl-amino]-5,5-diphenyl-pentanoic acid N-[2-(piperidin-1-yl)-ethyl]-amide; TLC: ethyl acetate $R_f$=0.11.

EXAMPLE 32/4

4-[N'-(3,5-Bistrifluoromethyl-benzoyl)-N'-methyl-amino]-5,5-diphenyl-pentanoic acid N-(3,4-dichlorobenzyl)-amide; TLC: ethyl acetate $R_f$=0.69.

EXAMPLE 32/5

4-[N'-(3,5-Bistrifluoromethyl-benzoyl)-N'-methyl-amino]-5,5-diphenyl-pentanoic acid {4-[2-oxo-2-(pyrrolidin-1-yl)-ethyl]-piperazine-1-amide}; TLC: ethyl acetate $R_f$=0.11

EXAMPLE 33

4-[N'-(3,5-Bistrifluoromethyl-benzoyl)-N'-methyl-amino]-5,5-diphenyl-pentanoic acid (benzotriazole-1-amide)

A solution of 0.05 ml (0.362 mmol) of triethylamine and 38 mg (0.0726 mmol) of 4-[N-(3,5-bistrifluoromethyl-benzoyl)-N-methyl-amino]-5,5-diphenyl-pentanoic acid [Example 32(h)] in 0.5 ml of methylene chloride and a solution of 30.6 mg (0.289 mmol) of 1-propanephosphonic acid anhydride in 0.5 ml of methylene chloride are added in succession to 10.4 mg (0.087 mmol) of 1H-benzotriazole and the mixture is left to stand at room temperature for 24 hours. The reaction mixture is then washed with 0.5 ml of a 1N aqueous potassium carbonate solution. The organic phase is concentrated by evaporation in a vacuum centrifuge. The title compound is obtained in the form of a white foam. TLC: ethyl acetate $R_f$=0.80.

The following are also prepared analogously to Example 33:

EXAMPLE 33/1

4-[N'-(3,5-Bistrifluoromethyl-benzoyl)-N'-methyl-amino]-5,5-diphenyl-pentanoic acid N-(4-methyl-phenyl)-amide; TLC: ethyl acetate $R_f$=0.74

EXAMPLE 33/2

4-[N'-(3,5-Bistrifluoromethyl-benzoyl)-N'-methyl-amino]-5,5diphenyl-pentanoic acid (3-dimethylaminomethyl-indole-1-amide); TLC: ethyl acetate $R_f$=0.57

EXAMPLE 33/3

4-[N'-(3,5Bistrifluoromethyl-benzoyl)-N'-methyl-amino]-5,5diphenyl-pentanoic acid N-(2-hydroxy-naphth-1-yl)-amide; TLC: ethyl acetate $R_f$=0.80.

EXAMPLE 34

3-[N'-(3,5-Bistrifluoromethyl-benzoyl)-N'-methyl-amino]-4,4-diphenyl-butanoic acid N-butyl-amide 42 mg (0.0693 mmol) of 3-[N'-(3,5-bistrifluoromethyl-benzoyl)-N'-methyl-amino]-4,4-diphenyl-butanoic acid N-hydroxysuccinimidyl ester [Example 34(g)] are added to a solution of 6.1 mg (0.083 mmol) of butylamine and 11.6 ml (0.083 mmol) of triethylamine in 1 ml of methylene chloride and the mixture is left to stand at room temperature for 24 hours. The reaction mixture is then washed with 0.5 ml of a 1N aqueous potassium carbonate solution. The organic phase is concentrated by evaporation in a vacuum centrifuge. The title compound is obtained in the form of a white foam. TLC: methylene chloride/methanol (98:2) $R_f$=0.24.

The starting compound is prepared as follows:
(a) Methanesulfonic acid 2-(N-tert-butoxycarbonyl-N-methyl)-amino-3,3-diphenyl-propyl ester A solution of 3.6 ml (46.1 mmol) of methanesulfonyl chloride in 20 ml of methylene chloride is added at 0° C. via a cannula to a solution of 14.9 g (43.7 mmol) of (1-hydroxymethyl-2,2-diphenyl-ethyl)-methyl-carbamic acid tert-butyl ester and 7.3 ml (52.1 mmol) of triethylamine in 80 ml of methylene chloride. The reaction mixture is stirred at 0° C. for 80 minutes and then at room temperature for 4 hours. The mixture is diluted with ethyl acetate and poured into ice-water. The organic phase is washed twice with ice-cold 1M citric acid and once with brine, dried over sodium sulfate and concentrated by evaporation. The title compound is obtained in the form of a yellow solid. TLC: methylene chloride/methanol (95:5) $R_f$=0.77; $R_t$(HPLC)= 19.4 min; $^1$H-NMR (300 MHz, CDCl$_3$, RT) d 7.39–7.15 (m,10H), 5.59–5.21 (m, 1H), 4.16 (m, 3H), 2.90 (s, 3H), 2.71/2.62 (s, 3H), 1.52/1.38 (s, 9H).

(b) (1-Cyanomethyl-2,2-diphenyl-ethyl)-methyl-carbamic acid tert-butyl ester

A solution of 18.3 g (43.7 mmol) of methanesulfonic acid 2-(N-tert-butoxycarbonyl-N-methyl)-amino-3,3-diphenyl-propyl ester in 140 ml of acetonitrile is added via a cannula to a solution of 8.6 g (52.3 mmol) of tetraethylammonium cyanide in 50 ml of acetonitrile. After 84 hours a further 4.3 g (26.1 mmol) of tetraethylammonium cyanide are added. After a total of 10 days the reaction mixture is concentrated by evaporation and the residue is diluted with ethyl acetate/hexane (1:4) and the resulting solid is filtered off. The filtrate is again concentrated by evaporation and the residue is chromatographed on silica gel with ethyl acetate/hexane (1:4). The title compound is obtained in the form of a white foam. TLC: ethyl acetate/hexane (1:4) $R_f$=0.35; $R_t$(HPLC)= 19.8 min; $^1$H-NMR (300 MHz, CDCl$_3$, RT) d 7.39–7.17 (m, 10H), 5.60–5.15 (m, 1H), 4.36–3.96 (m, 1H), 2.73/2.68 (s, 3H), 2.05 (m, 2H), 1.55/1.41 (s, 9H).

Alternatively, the intermediate of example 34(b) may also be prepared as follows:
(b1) (1-Cyanomethyl-2,2-diphenyl-ethyl)-methyl-carbamic acid tert-butyl ester 5.2 ml (82.9 mmol) of methyl iodide is added to a solution of 18.5 g (54.9 mmol) of (1-Cyanomethyl-2,2-diphenyl-ethyl)-carbamic acid tert-butyl ester in 100 ml of N,N-dimethyl-formamide, and the mixture is cooled to 0° C. 2.6 g (60.6 mmol) of 55% sodium hydride is added in several portions. After 1 h the mixture is warmed to RT and 75 ml of N,N-dimethylformamide is added for further dilution. After a total of 3.5 h the reaction mixture is poured into water and extracted with ethyl acetate. The organic phase is washed with water and brine, dried over sodium sulfate and concentrated by evaporation. The title compound is obtained in the form of an orange-brown mass. TLC: ethyl acetate/hexane (1:4) $R_f$=0.35; $R_t$(HPLC)=20.0 min; $^1$H-NMR (300 MHz, CDCl$_3$, RT) d 7.39–7.17 (m, 10H), 5.60–5.15 (m, 1H), 4.36–3.96 (m, 1H), 2.73/2.68 (s, 3H), 2.05 (m, 2H), 1.55/1.41 (s, 9H).

The corresponding starting materials are prepared as follows.
(b11) Methansulfonic acid 2-N-tert-butoxycarbonylamino-3,3-diphenyl-propyl ester A solution of 4.6 ml (58.9 mMol) of methansulfonyl chloride in 25 ml of methylene chloride is added at 0° C. via a cannula to a solution of 18.2 g (55.5 mmol) of (1-hydroxymethyl-2,2-diphenyl-ethyl)-carbamic acid tert-butyl ester (see WO-A-94/03429) and 9.3 ml (66.4 mmol) of triethylamine in 80 ml of methylene chloride. After 3.5 h at RT the reaction mixture is diluted with ethyl acetate and poured into ice-water. The organic phase is washed twice with ice-cold 1M citric acid and once with brine, dried over sodium sulfate and concentrated by evaporation. The title compound is obtained in the form of a beige solid. TLC: methylene chloride/methanol (95:5) $R_f$=0.77; $R_t$(HPLC)= 18.3 min; $^1$H-NMR (300 MHz, CDCl$_3$, RT) d 7.34–7.19 (m, 10H), 4.78–4.56 (m, 2H), 4.32 (m, 1H), 4.14 (d, 1H), 4.01 (dd, 1H), 2.91 (s, 3H), 1.34 (s, 9H).

(b12) (1-Cyanomethyl-2,2-diphenyl-ethyl)-carbamic acid tert-butyl ester

A solution of 22.5 g (55.5 mmol) of methanesulfonic acid-2-N-tert-butoxycarbonylamino-3,3-diphenyl-propyl ester in 150 ml of acetonitrile is added via a cannula to a solution of 14.1 g (85.5 mmol) of tetraethylammonium cyanide in 50 ml of acetonitrile. After 5 days the reaction mixture is concentrated by evaporation and the residue is diluted with ethyl acetate and washed twice with water and once with brine. The aqueous phases are extracted once with ethyl acetate. The combined organic phases are dried over sodium sulfate and concentrated by evaporation. The title compound is obtained in the form of a beige foam. TLC: methylene chloride/methanol (95:5) $R_f$=0.79; $R_t$(HPLC)= 18.9 min; $^1$H-NMR (300 MHz, CDCl$_3$, RT) d 7.35–7.19 (m, 10H), 4.65 (br, 2H), 4.15 (d, 1H), 2.82 (br d, 1H), 2.31 (dd, 1H), 1.34 (s, 9H).

(c) 3-Methylamino-4,4-diphenyl-butanoic acid hydrochloride

A suspension of 7.2 g (20.4 mmol) of (1-cyanomethyl-2,2-diphenyl-ethyl)-methyl-carbamic acid tert-butyl ester and 80 ml of 6N hydrochloric acid is stirred under reflux for 14 hours. The reaction mixture is concentrated by evaporation and then twice toluene is added and the mixture concentrated by evaporation again. The title compound is obtained in the form of a beige solid. $R_t$(HPLC)=10.1 min; $^1$H-NMR (300 MHz, CDCl$_3$, RT) d 8.62 (br, 2H), 7.57–7.19 (m, 10H), 4.43 (d, 1H), 4.36 (m, 1H), 2.94–2.72 (m, 2H), 2.37 (br s, 3H).

(d) 3-Methylamino-4,4-diphenyl-butanoic acid methyl ester hydrochloride 3 ml (40.9 mmol) of thionyl chloride are added dropwise at 0° C. to a fine suspension of 6.2 g (20.4 mmol) of 3-methylamino-4,4-diphenyl-butyric acid hydrochloride in 70 ml of methanol. After a total of 88 hours at room temperature the reaction mixture is concentrated by evaporation and ether is added. The beige precipitate is filtered off, then washed with ether and dried under a high vacuum. The title compound is obtained in the form of a beige solid. $R_t$(HPLC)=11.2 min; $^1$H-NMR (300 MHz, d$^6$-DMSO, RT) d 9.41 (br, 1H), 8.56 (br, 1H), 7.59–7.18 (m, 10H), 4.56 (m, 1H), 4.43 (d, 1H), 3.46 (s, 3H), 2.87 (dd, 1H), 2.64 (dd,$_1$H), 2.40 (s, 3H).

(e) 3-[N-(3,5-Bistrifluoromethyl-benzoyl)-N-methyl-amino]-4,4-diphenyl-butanoic acid methyl ester A solution of 6.8 g (21 mmol) of 3-methylamino-4,4-diphenyl-butanoic acid methyl ester hydrochloride in 100 ml of methylene chloride is added to a solution of 4.2 ml (22 mmol) of 3,5-bistrifluoromethyl-benzoyl chloride in 100 ml of methylene chloride. Then, at 0° C., 6.6 ml (46 mmol) of triethylamine and 0.26 g (2.1 mmol) of 4-dimethylaminopyridine are added. After 6 hours the reaction mixture is diluted with ethyl acetate and washed twice with water and once with brine. The organic phase is dried over sodium sulfate and concentrated by evaporation. The residue is chromatographed on silica gel with methylene chloride/methanol (99:1 to 95:5). The title compound is obtained in the form of a light-yellow solid. TLC: methylene chloride/methanol (95:5) $R_f$=0.88; $R_t$(HPLC)=21.4 min; $^1$H-NMR (400 MHz, d$^6$-DMSO, 150° C.) d 7.97 (br, 1H), 7.45–7.19 (m, 12H), 5.46 (br, 1H), 4.46 (d, 1H), 3.54 (s, 3H), 2.87 (dd, 1H), 2.72 (s, 3H), 2.47 (dd, 1H); FAB-MS (M+H)$^+$=524.

(f) 3-[N-(3,5-Bistrifluoromethyl-benzoyl)-N-methyl-amino]-4,4-diphenyl-butanoic acid 25 ml of 1N sodium hydroxide are added to a solution of 7.8 g (15 mmol) of 3-[N-(3,5-bis-trifluoromethyl-benzoyl)-N-methyl-amino]-4,4-diphenyl-butanoic acid methyl ester in 100 ml of tetrahydrofuran/methanol (2:1). After 5 hours the reaction mixture is concentrated by evaporation, diluted with water and rendered acidic with cold 2N hydrochloric acid. The white precipitate is filtered off, then washed with water and dried under a high vacuum at 50° C. The title compound is obtained in the form of a white solid. TLC: methylene chloride/methanol (95:5) $R_f$=0.14; $R_t$(HPLC)= 19.2 min; $^1$H-NMR (400 MHz, d$^6$-DMSO, 150° C.) d 7.96 (br, 1H), 7.42–7.19 (m, 12H), 5.42 (br, 1H), 4.45 (d, 1H), 2.79 (dd, 1H), 2.72 (s, 3H), 2.37 (dd, 1H); FAB-MS (M+H)$^+$=510.

(g) 3-[N'-(3,5-Bistrifluoromethyl-benzoyl)-N'-methyl-amino]-4,4-diphenyl-butanoic acid N-hydroxysuccinimidyl ester 147 mg (1.05 mmol) of N-hydroxysuccinimide and 29 mg (0.24 mmol) of 4-dimethylaminopyridine are added to a solution of 600 mg (1.15 mmol) of 3-[N-(3,5-bistrifluoromethyl-benzoyl)-N-methyl-amino]-4,4-diphenyl-butanoic acid in 9 ml of methylene chloride and the mixture is cooled to 0° C. Then 253 mg (1.30 mmol) of N-ethyl-N'-(3-dimethylaminopropyl)-carbodiimide hydrochloride are added and the reaction mixture is stirred at 0° C. for 10 minutes and then at room temperature for 22 hours. The mixture is poured into ice-cold 5% citric acid and the aqueous phase is extracted three times with methylene chloride. The combined organic phases are washed with brine, dried over sodium sulfate and concentrated by evaporation. The title compound is obtained in the form of a white solid. TLC: methylene chloride/methanol (95:5) $R_f$=0.85; $R_t$(HPLC)=20.6 min.

The following are also prepared analogously to Example 34:

EXAMPLE 34/1

3-[N'-(3,5-Bistrifluoromethyl-benzoyl)-N'-methyl-amino]-4,4-diphenyl-butanoic acid N,N-bis(2-hydroxyethyl)-amide; TLC: methylene chloride/methanol (95:5) $R_f$=0.32

EXAMPLE 34/2

3-[N'-(3,5-Bistrifluoromethyl-benzoyl)-N'-methyl-amino]-4,4-diphenyl-butanoic acid N-benzyl-N-methyl-amide; TLC: methylene chloride/methanol (98:2) $R_f$=0.38

EXAMPLE 34/3

3-[N'-(3,5-Bistrifluoromethyl-benzoyl)-N'-methyl-amino]-4,4-diphenyl-butanoic acid N-[2-(2-pyridyl)-ethyl]-amide; TLC: methylene chloride/methanol (95:5) $R_f$=0.32

EXAMPLE 34/4

3-[N'-(3,5-Bistrifluoromethyl-benzoyl)-N'-methyl-amino]-4,4-diphenyl-butanoic acid N-(carbamoylmethyl)-amide; TLC: methylene chloride/methanol (9:1) $R_f$=0.48

EXAMPLE 34/5

3-[N'-(3,5-Bistrifluoromethyl-benzoyl)-N'-methyl-amino]-4,4-diphenyl-butanoic acid [4-(2-methoxy-phenyl)-piperazine-1-amide]; TLC: methylene chloride/methanol (95:5) $R_f$=0.28

EXAMPLE 34/6

3-[N'-(3,5-Bistrifluoromethyl-benzoyl)-N'-methyl-amino]-4,4-diphenyl-butanoic acid N-cyanomethyl-N-methyl-amide; TLC: methylene chloride/methanol (95:5) $R_f$=0.44.

EXAMPLE 35

3-[N'-(3,5-Bistrifluoromethyl-benzoyl)-N'-methyl-amino]-4,4-diphenyl-butanoic acid N-(4-cyclohexyl-phenyl)-amide A solution of 0.05 ml (0.362 mmol) of triethylamine and 37 mg (0.0726 mmol) of 3-[N-(3,5-bistrifluoromethyl-benzoyl)-N-methyl-amino]-4,4-diphenyl-butanoic acid in 0.5 ml of methylene chloride and a solution of 30.6 mg (0.289 mmol) of 1-propanephosphonic acid anhydride in 0.5 ml of methylene chloride are added in succession to 15.2 mg (0.087 mmol) of 4-cyclohexylaniline and the mixture is left to stand at room temperature for 24 hours. The reaction mixture is then washed with 0.5 ml of a 1N aqueous potassium carbonate solution. The organic phase is concentrated by evaporation in a vacuum centrifuge. The title compound is obtained in the form of a white foam. TLC: methylene chloride/methanol (95:5) $R_f$=0.44

EXAMPLE 35/1

3-[N'-(3,5Bistrifluoromethyl-benzoyl)-N'-methyl-amino]-4,4-diphenyl-butanoic acid (5-benzyloxy-indole-1-amide); TLC: methylene chloride/methanol (95:5) $R_f$=0.85

EXAMPLE 35/2

3-[N'-(3,5-Bistrifluoromethyl-benzoyl)-N'-methyl-amino]-4,4-diphenyl-butanoic acid (4-methyl-imidazole-1-amide); TLC: methylene chloride/methanol (95:5) $R_f$=0.50

EXAMPLE 36

4-[N'-(3.5-Bistrifluoromethyl-benzoyl)-N'-methyl-amino]-5.5-diphenyl-pentanoic acid N-(1 (S)-hydroxymethyl-3-methyl-butyl)-amide [=4-[N'-(3,5-Bistrifluoromethyl-benzoyl)-N'-methyl-amino]-5,5-diphenyl-pentanoic acid N-(L-leucinol)-amide]

A solution of 120 mg (0.23 mmol) of 4-[N-(3,5-bistrifluoromethyl-benzoyl)-N-methyl-amino]-5,5-diphenyl-pentanoic acid (example 32 h) and 45 µl (0.32 mmol) of triethylamine in 4 ml of N,N-dimethylformamide at 0° C. is treated with 36 µl (0.28 mmol) of (S)-leucinol, followed by 45 µl (0.28 mmol) of diethyl cyanophosphonate. After stirring for 4 h at room temperature, the reaction mixture is concentrated, diluted with ethyl acetate, and then washed with saturated sodium bicarbonate solution. The aqueous layer is further extracted with ethyl acetate (3×). The organic layers are combined, dried with sodium sulfate and concentrated. The residue is then purified by flash chromatography (98:2 to 95:5 methylene chloride/methanol) to give the title compound as a white solid (mixture of diastereomers). TLC: methylene chloride/methanol (95:5) $R_f$=0.22, 0.19

The following compounds are synthesized analogously:

EXAMPLE 36/1

4-[N'-(3,5-Bistrifluoromethyl-benzoyl)-N'-methyl-amino]-5,5-diphenyl-pentanoic acid N-propyl-amide; TLC: methylene chloride/methanol (95:5) $R_f$=0.31

EXAMPLE 36/2

4-[N'-(3,5-Bistrifluoromethyl-benzoyl)-N'-methyl-amino]-5,5-diphenyl-pentanoic acid N-butyl-amide; TLC: methylene chloride/methanol (95:5) $R_f$=0.31

EXAMPLE 36/3
4-[N'-(3,5-Bistrifluoromethyl-benzoyl)-N'-methyl-amino]-5,5-diphenyl-pentanoic acid N-(2-hydroxy-ethyl)-amide; TLC: methylene chloride/methanol (95:5) $R_f$=0.16

EXAMPLE 36/4
4-[N'-(3,5-Bistrifluoromethyl-benzoyl)-N'-methyl-amino]-5,5-diphenyl-pentanoic acid N-(1-hydroxymethyl-2-methyl-propyl)-amide; TLC: methylene chloride/methanol (95:5) $R_f$=0.19, 0.16

EXAMPLE 36/5
4-[N'-(3,5-Bistrifluoromethyl-benzoyl)-N'-methyl-amino]-5,5-diphenyl-pentanoic acid N-cyclohexyl-amide; TLC: methylene chloride/methanol (95:5) $R_f$=0.36

EXAMPLE 36/6
4-[N'-(3,5-Bistrifluoromethyl-benzoyl)-N'-methyl-amino]-5,5-diphenyl-pentanoic acid N-[2-(4-hydroxy-phenyl)-ethyl]-amide; TLC: methylene chloride/methanol (95:5) $R_f$=0.19

EXAMPLE 36/7
4-[N'-(3,5-Bistrifluoromethyl-benzoyl)-N'-methyl-amino]-5,5-diphenyl-pentanoic acid N-(2-pyridylmethyl)-amide; TLC: methylene chloride/methanol (95:5) $R_f$=0.23

EXAMPLE 36/8
4-[N'-(3,5-Bistrifluoromethyl-benzoyl)-N'-methyl-amino]-5,5-diphenyl-pentanoic acid N-[3-(morpholin-4-yl)-propyl]-amide; TLC: methylene chloride/methanol (95:5) $R_f$=0.23

EXAMPLE 36/9
4-[N'-(3,5-Bistrifluoromethyl-benzoyl)-N'-methyl-amino]-5,5-diphenyl-pentanoic acid N-(D,L-epsilon-caprolactam-3-yl)-amide; TLC: methylene chloride/methanol (95:5) $R_f$=0.20

EXAMPLE 36/10
4-[N'-(3,5-Bistrifluoromethyl-benzoyl)-N'-methyl-amino]-5,5-diphenyl-pentanoic acid N-[(1-ethoxycarbonyl-cyclopentyl)-methyl]-amide; TLC: methylene chloride/methanol (95:5) $R_f$=0.50; starting amine: 1-aminomethyl-cyclopentanecarboxylic acid ethyl ester (EP-A-443983)

EXAMPLE 36/11
4-[N'-(3,5-Bistrifluoromethyl-benzoyl)-N'-methyl-amino]-5,5-diphenyl-pentanoic acid (4-acetylamino-4-phenyl-piperidineamide); TLC: methylene chloride/methanol (9:1) $R_f$=0.31; starting amine: hydrochloride salt of 4-acetylamino-4-phenyl-piperidine (EP-A-474561)

EXAMPLE 36/12
4-[N'-(3,5-Bistrifluoromethyl-benzoyl)-N'-methyl-amino]-5,5-diphenyl-pentanoic acid (4(R)-phenylsulfinylmethyl-4-methoxy-piperidineamide); TLC: methylene chloride/methanol (9:1) $R_f$=0.26; starting amine: p-toluenesulfonic acid salt of 4(R)-benzenesulfinylmethyl4-methoxy-piperidine [Bioorg. Med. Chem. Lett. 4 (1994) 1951]

EXAMPLE 36/13
4-[N'-(3,5-Bistrifluoromethyl-benzoyl)-N'-methyl-amino]-5,5-diphenyl-pentanoic acid N-[(1-ethoxycarbonyl-cyclohexyl)-methyl]-amide; TLC: methylene chloride/methanol (95:5) $R_f$=0.44; starting amine: 1-aminomethyl-cyclohexanecarboxylic acid ethyl ester (EP-A-443983)

EXAMPLE 36/14
4-[N'-(3,5-Bistrifluoromethyl-benzoyl)-N'-methyl-amino]-5,5-diphenyl-pentanoic acid [1-methyl-spiro(indol-2-one-3,4'-piperidine)-amide]; TLC: methylene chloride/methanol (95:5) $R_f$=0.43; starting amine: 1-methyl-spiro(indol-2-one-3,4'-piperidine) (WO-A-94/29309)

EXAMPLE 37
4(R) or 4(S)-[N'-(3.5-Bistrifluoromethyl-benzoyl)-N'-methyl-amino]-5.5-diphenyl-pentanoic acid N-butyl-amide A solution of 100 mg (0.19 mmol) of 4(R) or 4(S)-[N-(3,5-bistrifluoromethyl-benzoyl)-N-methyl-amino]-5,5-diphenyl-pentanoic acid (derived from enantiomer 1, see below) and 37 ml (0.27 mmol) of triethylamine in 3 ml of N,N-dimethylformamide at 0° C. is treated with 23 ml (0.23 mmol) of butylamine, followed by 37 ml (0.23 mmol) of diethyl cyanophosphonate. After stirring for 2 h at room temperature, the reaction mixture is concentrated, diluted with ethyl acetate, and then washed with saturated sodium bicarbonate solution. The aqueous layer is further extracted with ethyl acetate (3×). The organic layers are combined, dried with sodium sulfate and concentrated. The residue is then purified by flash chromatography (98:2 to 95:5 methylene chloride/methanol) to give the title compound as a colorless oil which slowly solidified on standing. TLC: methylene chloride/methanol (95:5) $R_f$=0.27; $[a]_D$=−20.5 (c=1,methanol).

The starting material is prepared as follows:

(a) 4(R) or 4(S)-[N-(3.5-bistrifluoromethyl-benzoyl)-N-methyl-amino]-5.5-diphenyl-pentanoic acid ethyl ester 4.0 g (7.2 mmol) of 4(R,S)-[N-(3,5-bistrifluoromethyl-benzoyl)-N-methyl-amino]-5,5-diphenyl-pentanoic acid ethyl ester are chromatographed on a Chiralcel® OD-prep. column (50×5 cm) using [(980:20 hexane/isopropanol)= 0.1% trifluoroacetic acid] as eluent. Following concentration, the two pure enantiomers (>99% ee) of the title compound are obtained as thick, gold oils. HPLC (Chiralcel® OD—250×4.6 mm): hexane/isopropanol (980:20) $R_t$ (enantiomer 1)=8.63 min, $R_t$ (enantiomer2)= 9.36 min.

(b) 4(R) or 4(S)-[N-(3,5-bistrifluoromethyl-benzoyl)-N-methyl-amino]-5,5-diphenyl-pentanoic acid 6 ml of 1N sodium hydroxide solution are added to a solution of 2.0 g (3.6 mmol) of 4(R) or 4(S)-[N-(3,5-bistrifluoromethyl-benzoyl)-N-methyl-amino]-5,5-diphenyl-pentanoic acid ethyl ester (enantiomer 1) in 21 ml of 2:1 tetrahydrofuran/methanol at room temperature. After stirring for 4 h, the reaction mixture is concentrated, diluted with water, and then acidified with ice-cold 2N hydrochloric acid solution. The resulting precipitate is filtered, washed with water and a small amount of hexanes, and then dried overnight under vacuum at 50° C. to give the title compound as a white solid. TLC: methylene chloride/methanol (95:5) $R_f$=0.11; $[a]_D$=−31.1 (c=1,methanol).

The following compounds are synthesized analogously:

EXAMPLE 37/1
4(R) or 4(S)-[N'-(3,5-Bistrifluoromethyl-benzoyl)-N'-methyl-amino]-5,5-diphenyl-pentanoic acid N-[1(S)-hydroxymethyl-2-methyl-propyl]-amide; TLC: methylene chloride/methanol (95:5) $R_f$=0.34; starting amine: 2(S)-amino-3-methyl-1-butanol

EXAMPLE 37/2
4(R) or 4(S)-[N'-(3,5-Bistrifluoromethyl-benzoyl)-N'-methyl-amino]-5,5-diphenyl-pentanoic acid N-[1(R)-hydroxymethyl-2-methyl-propyl]-amide; TLC: methylene chloride/methanol (95:5) $R_f$=0.24; starting amine: 2(R)-amino-3-methyl-1-butanol

EXAMPLE 38
4-[N'-(3,5-Bistrifluoromethyl-benzoyl)-N'-methyl-amino]-5,5-diphenyl-pent-2-enoic acid N-butyl-amide A solution of 100 mg (0.19 mmol) of 4-[N-(3,5-bistrifluoromethyl-benzoyl)-N-methyl-amino]-5,5-diphenyl-pent-2-enoic acid and 37 μl (0.27 mmol) of triethylamine in 3 ml of N,N-dimethylformamide at 0° C. is treated with 23 μl (0.23 mmol) of butylamine, followed by 38 μl (0.23 mmol) of diethyl cyanophosphonate. After stirring for 4 h at room temperature, the reaction mixture is concentrated, diluted with ethyl acetate, and then washed with saturated sodium bicarbonate solution. The aqueous layer is further extracted with ethyl acetate (3×). The organic layers are combined, dried with sodium sulfate and concentrated. The residue is then purified by flash chromatography (95:5 methylene chloride/methanol) to give the title compound as a white solid. TLC: methylene chloride/methanol (95:5) $R_f$=0.23.

The starting material is prepared as follows:
(a) 4-[N-(3,5-bistrifluoromethyl-benzoyl)-N-methyl-amino]-5,5-diphenyl-pent-2-enoic acid 15 ml of 1N sodium hydroxide solution are added to a solution of 5.0 g (9.1 mmol) of 4-[N-(3,5-bistrifluoromethyl-benzoyl)-N-methyl-amino]-5,5-diphenyl-pent-2-enoic acid ethyl ester in 60 ml of 2:1 tetrahydrofuran/methanol at room temperature. After stirring for 5 h, the reaction mixture is concentrated, diluted with water, and then acidified with ice-cold 2N hydrochloric acid solution. The resulting precipitate is filtered, washed with water and a small amount of hexanes, and then dried overnight under vacuum at 50° C. to give the title compound as a white solid. TLC: methylene chloride/methanol (95:5) $R_f$=0.08.

The following compounds are synthesized analogously:

EXAMPLE 38/1
4-[N'-(3,5-Bistrifluoromethyl-benzoyl)-N'-methyl-amino]-5,5-diphenyl-pent-2-enoic acid N-allyl-amide; TLC: methylene chloride/methanol (95:5) $R_f$=0.31

EXAMPLE 38/2
4-[N'-(3,5-Bistrifluoromethyl-benzoyl)-N'-methyl-amino]-5,5-diphenyl-pent-2-enoic acid N-[1(S)-hydroxymethyl-3-methyl-butyl]-amide {=4-[N'-(3,5-Bistrifluoromethyl-benzoyl)-N'-methyl-amino]-5,5-diphenyl-pent-2-enoic acid N-(L-leucinol)-amide}; TLC: methylene chloride/methanol (9:1) $R_f$=0.50

EXAMPLE 38/3
4-[N'-(3,5-Bistrifluoromethyl-benzoyl)-N'-methyl-amino]-5,5-diphenyl-pent-2-enoic acid N-(5-hydroxy-pentyl)-amide; TLC: methylene chloride/methanol (9:1) $R_f$=0.39

EXAMPLE 38/4
4-[N'-(3,5-Bistrifluoromethyl-benzoyl)-N'-methyl-amino]-5,5-diphenyl-pent-2-enoic acid N-[2-(morpholin-4-yl)-ethyl]-amide; TLC: methylene chloride/methanol (9:1) $R_f$=0.38

EXAMPLE 38/5
4-[N'-(3,5-Bistrifluoromethyl-benzoyl)-N'-methyl-amino]-5,5-diphenyl-pent-2-enoic acid N-(2-pyridylmethyl)-amide; TLC: methylene chloride/methanol (9:1) $R_f$=0.42

EXAMPLE 38/6
4-[N'-(3,5-Bistrifluoromethyl-benzoyl)-N'-methyl-amino]-5,5-diphenyl-pent-2-enoic acid N-[2-(2-pyridyl)-ethyl]-amide; TLC: methylene chloride/methanol (9:1) $R_f$=0.42

EXAMPLE 38/7
4-[N'-(3,5-Bistrifluoromethyl-benzoyl)-N'-methyl-amino]-5,5-diphenyl-pent-2-enoic acid N-[2-(4-hydroxy-phenyl)-ethyl]-amide; TLC: methylene chloride/methanol (9:1) $R_f$=0.40

EXAMPLE 38/8
4-[N'-(3,5-Bistrifluoromethyl-benzoyl)-N'-methyl-amino-]-5,5-diphenyl-pent-2-enoic acid N-[3-(morpholin-4-yl)-propyl]-amide; TLC: methylene chloride/methanol (9:1) $R_f$=0.37

EXAMPLE 38/9
4-[N'-(3,5-Bistrifluoromethyl-benzoyl)-N'-methyl-amino]-5,5-diphenyl-pent-2-enoic acid N-(D,L-epsilon-caprolactam-3-yl)-amide; TLC: methylene chloride/methanol (95:5) $R_f$=0.33

EXAMPLE 38/10
4-[N'-(3,5-Bistrifluoromethyl-benzoyl)-N'-methyl-amino]-5,5-diphenyl-pent-2-enoic acid N-cyclohexyl-amide; TLC: methylene chloride/methanol (95:5) $R_f$=0.40.

EXAMPLE 1

Continued

The Following Examples are Synthesized Analogously to Example 1

EXAMPLE 1/4
4-[N'-Methyl-N'-(3,5-bistrifluormethyl-benzoyl)-amino]-5-(4-chlorophenyl)-pent-2-enoic acid N-[2-(3-pyridyl)-ethyl]-amide; TLC: methylene chloride/methanol (95:5) $R_f$=0.08

EXAMPLE 1/5
4-[N'-Methyl-N'-(3,5-bistrifluormethyl-benzoyl)-amino]-5-(4-chlorophenyl)-pent-2-enoic acid N-[2-(4-pyridyl)-ethyl]-amide; TLC: methylene chloride/methanol (95:5) $R_f$=0.09

EXAMPLE 1/6
4-[N'-Methyl-N'-(3,5-bistrifluormethyl-benzoyl)-amino]-5-(4-chlorophenyl)-pent-2-enoic acid N-(4-chinolinyl-methyl)-amide; TLC: methylene chloride/methanol (95:5) $R_f$=0.35

EXAMPLE 1/7
4-[N'-Methyl-N'-(3,5-bistrifluormethyl-benzoyl)-amino]-5-(4-chlorophenyl)pent-2-enoic acid N-[2-(4-chinolinyl)-ethyl]-amide; TLC: methylene chloride/methanol (95:5) $R_f$=0.38

EXAMPLE 1/8
4-[N'-Methyl-N'-(3,5-bistrifluormethyl-benzoyl)-amino]-5-(4-chlorophenyl)-pent-2-enoic acid N-(D,L-epsilon-caprolactam-3-yl)-amide; TLC: ethyl acetate $R_f$=0.16

EXAMPLE 1/9
4-[N'-Methyl-N'-(3,5bistrifluormethyl-benzoyl)-amino]-5-(4-chlorophenyl)-pent-2-enoic acid N-[1,3,4,5-tetrahydrobenzo-azepin-2-on-3-yl]-amide; TLC: ethyl acetate $R_f$=0.44, (the starting amine, 3-amino-1,3,4,5-tetrahydrobenzo-azepin-2-one, is described e.g. in Chem. Abstr. 99:53621d P)

EXAMPLE 1/10
4-[N'-Methyl-N'-(3,5-bistrifluormethyl-benzoyl)-amino]-5-(4-chlorophenyl)-pent-2-enoic acid (4-acetylamino-4-phenyl-piperidineamide); TLC: ethyl acetate $R_f$=0.14 [the starting amine, 4-phenyl-4-acetylamino-piperidine (=N-(4-phenyl-piperidine-4-yl)-acetamide), is described e.g. in Chem. Abstr. 117:26590d P]

EXAMPLE 1/11
4-[N'-Methyl-N'-(3,5-bistrifluormethyl-benzoyl)-amino]-5-(4-chlorophenyl)-pent-2-enoic acid (4-carbamoyl-4-phenyl-

EXAMPLE 1/12
4-[N'-Methyl-N'-(3,5-bistrifluormethyl-benzoyl)-amino]-5-(4-chlorophenyl)-pent-2-enoic acid (4-phenylsulfinylmethyl-4-methoxy-piperidineamide); TLC: ethyl acetate $R_f=0.14$, [the starting amine 4-benzenesulfinylmethyl-4-methoxy-piperidine is described in Biorg. Med. Chem. Lett. 4 (1994) 1951]

EXAMPLE 1/13
4-[N'-Methyl-N'-(3,5-bistrifluormethyl-benzoyl)-amino]-5-(4-chlorophenyl)-pent-2-enoic acid N-[3-(2-pyridyl)-propyl]-amide; TLC: ethyl acetate $R_f=0.1$

EXAMPLE 1/14
4-[N'-Methyl-N'-(3,5-bistrifluormethyl-benzoyl)-amino]-5-(4-chlorophenyl)-pent-2-enoic acid N-[2-(3-methoxy-phenyl)-ethyl]-amide; TLC: ethyl acetate $R_f=0.44$

EXAMPLE 1/15
4-[N'-Methyl-N'-(3,5-bistrifluormethyl-benzoyl)-amino]-5-(4-chlorophenyl)-pent-2-enoic acid N-cyclohexyl-amide; TLC: ethyl acetate $R_f=0.6$

EXAMPLE 1/16
4-[N'-Methyl-N'-(3,5-bistrifluormethyl-benzoyl)-amino]-5-(4-chlorophenyl)-pent-2-enoic acid N-cycloheptyl-amide; TLC: ethyl acetate $R_f=0.6$

EXAMPLE 1/17
(4R)- and (4S)-4-[N'-Methyl-N'-(3,5-bistrifluormethyl-benzoyl)-amino]-5-(4-chlorophenyl)-pent-2-enoic acid N-[2-(2-pyridyl)-ethyl]-amide are prepared by chromatography of racemic 4-[N'-Methyl-N'-(3,5-bistrifluormethyl-benzoyl)-amino]-5-(4-chlorophenyl)-pent-2-enoic acid N-[2-(2-pyridyl)-ethyl]-amide (see example 1/2) on a Chiracel® OD-prep. column (50×5 cm) using (hexane/ethanol 95:5) as eluent. Following concentration, the two pure enantiomeres (ee>99%) are obtained as colorless oils. HPLC (Chiracel® OD—250×4.6 mm, hexane/ethanol 95:5, flow 1 ml/min, 30 bar): $R_t$ (enantiomer 1)=30.26 min, $R_t$ (enantiomer 2)=38.09 min.

EXAMPLE 5
Continued
The Following Examples are Synthesized Analogously to Example 5

EXAMPLE 5/24
4-[N'-Methyl-N'-(3,5-bistrifluormethyl-benzoyl)-amino]-5-(4-chlorophenyl)-pentanoic acid N-(5-hydroxy-pentyl)-amide; TLC: methylene chloride/methanol (95:5) $R_f=0.1$

EXAMPLE 5/25
4-[N'-Methyl-N'-(3,5-bistrifluormethyl-benzoyl)-amino]-5-(4-chlorophenyl)-pentanoic acid N-(4-methoxy-benzyl)-amide; TLC: methylene chloride/methanol (95:5) $R_f=0.34$

EXAMPLE 5/26
4-[N'-Methyl-N'-(3,5-bistrifluormethyl-benzoyl)-amino]-5-(4-chlorophenyl)-pentanoic acid N-(2-methyl-allyl)-amide; TLC: methylene chloride/methanol (95:5) $R_f=0.3$

EXAMPLE 5/27
4-[N'-Methyl-N'-(3,5-bistrifluormethyl-benzoyl)-amino]-5-(4-chlorophenyl)-pentanoic acid N-[2-(4-amino-phenyl)-ethyl]-amide; TLC: methylene chloride/methanol (95:5) $R_f=0.2$

EXAMPLE 5/28
4-[N'-Methyl-N'-(3,5-bistrifluormethyl-benzoyl)-amino]-5-(4-chlorophenyl)-pentanoic acid N-[1,5-dimethyl-2-phenyl-1,2-dihydro-pyrazol-3-on-4-yl]-amide; TLC: ethyl acetate $R_f=0.08$; starting amine used: 4-amino-1,5-dimethyl-2-phenyl-1,2-dihydro-pyrazol-3-one (=4-amino-antipyrine, e.g. Fluka).

EXAMPLE 5/29
4-[N'-Methyl-N'-(3,5-bistrifluormethyl-benzoyl)-amino]-5-(4-chlorophenyl)-pentanoic acid N-(5-cyano-pentyl)-amide; TLC: ethyl acetate $R_f=0.17$

EXAMPLE 5/30
4-[N'-Methyl-N'-(3,5-bistrifluormethyl-benzoyl)-amino]-5-(4-chlorophenyl)-pentanoic acid N-(D,L-epsilon-caprolactam-3-yl)-amide; TLC: ethyl acetate $R_f=0.16$

EXAMPLE 5/31
4-[N'-Methyl-N'-(3,5-bistrifluormethyl-benzoyl)-amino]-5-(4-chlorophenyl)-pentanoic acid N-[1-methyl-2-(2-pyridyl)-ethyl]-amide; TLC: ethyl acetate $R_f=0.1$

EXAMPLE 5/32
4-[N'-Methyl-N'-(3,5-bistrifluormethyl-benzoyl)-amino]-5-(4-chlorophenyl)-pentanoic acid N-[1-isopropyl-2-(2-pyridyl)-ethyl]-amide; TLC: ethyl acetate $R_f=0.2$

EXAMPLE 4
Continued
The Following Examples are Synthesized Analogously to Example 4

EXAMPLE 4/2
4-[N'-Methyl-N'-(3,5-bistrifluormethyl-benzoyl)-amino]-5-(4-chlorophenyl)-pentanoic acid N-[4-(ethoxycarbonyl)-phenylsulfon]-amide; TLC: ethyl acetate $R_f=0.45$

EXAMPLE 4/3
4-[N'-Methyl-N'-(3,5-bistrifluormethyl-benzoyl)-amino]-5-(4-chlorophenyl)-pentanoic acid N-[2-(methoxycarbonyl)-benzylsulfon]-amide; TLC: ethyl acetate $R_f=0.62$

EXAMPLE 4/4
4-[N'-Methyl-N'-(3,5-bistrifluormethyl-benzoyl)-amino]-5-(4-chlorophenyl)-pentanoic acid N-(methylsulfon)-amide; TLC: ethyl acetate $R_f=0.35$

EXAMPLE 4/5
4-[N'-Methyl-N'-(3,5-bistrifluormethyl-benzoyl)-amino]-5-(4-chlorophenyl)-pentanoic acid N-(2-methoxyphenylsulfon)-amide; TLC: hexane/ethyl acetate (1:1) $R_f=0.16$

EXAMPLE 4/6
4-[N'-Methyl-N'-(3,5-bistrifluormethyl-benzoyl)-amino]-5-(4-chlorophenyl)-pentanoic acid N-(2-phenyloxy-3-pyridylsulfon)-amide; TLC: hexane/ethyl acetate (1:1) $R_f=0.25$

EXAMPLE 4/7
4-[N'-Methyl-N'-(3,5-bistrifluormethyl-benzoyl)-amino]-5-(4-chlorophenyl)-pentanoic acid N-[2-(2-chlorophenyl)-ethenylsulfon]-amide; TLC: methylene chloride/methanol (95:5) $R_f=0.27$

EXAMPLE 4/8
4-[N'-Methyl-N'-(3,5-bistrifluormethyl-benzoyl)-amino]-5-(4-chlorophenyl)-pentanoic acid N-[4-(N"-methylcarbamoyl)-phenylsulfon]-amide A solution of 0.1 g 4-[N'-Methyl-N'-(3,5-bistrifluormethyl-benzoyl)-amino]-5-(4-chlorophenyl)-pentanoic acid N-[4-carboxy-phenylsulfon]-amide, 0.01 g methylamine-hydrochloride, 0.038 g N',N'-3-dimethyl-aminopropyl-N-ethyl-carbodiimide-hydrochloride and 0.048 g 4-dimethylaminopyridine in 8 ml of methylene chloride is stirred at room temperature for 18 h. After that the reaction mixture is concentrated in vacuo and then purified by chromatography on silicagel (ethyl acetate) to give the title compound as an amorphous white solid; TLC: ethyl acetate $R_f$=0.14

(a) Preparation of the starting material: 4-[N'-Methyl-N'-(3,5-bistrifluormethyl-benzoyl)-amino]-5-(4-chlorophenyl)-pentanoic acid N-[4-carboxy-phenylsulfon]-amide is prepared by treating a solution of 2.5 g 4-[N'-Methyl-N'-(3,5-bistrifluormethyl-benzoyl)-amino]-5-(4-chlorophenyl)-pentanoic acid N-[4-(ethoxycarbonyl)-phenylsulfon]-amide (this is the compound of example 4/2) in 60 ml THF/methanol (1:1) with a solution of 2.2 g lithium hydroxide (in 15 ml $H_2O$) for 1 h at room temperature. Then the reaction mixture is diluted with 200 ml 0.05N HCl and extracted two times with ethyl acetate. The combined organic layers are washed with water, saturated NaCl-soln. and dried ($MgSO_4$). After evaporation of the solvents the title compound is obtained as an amorphous white solid. TLC: ethyl acetate $R_f$=0.05.

Analogously to example 4/8—by reacting the carboxylic acid of example 4/8(a) with the corresponding amines—the following compounds are prepared:

EXAMPLE 4/9

4-[N'-Methyl-N'-(3,5-bistrifluormethyl-benzoyl)-amino]-5-(4-chlorophenyl)-pentanoic acid N-[4-(N'',N''-dimethylcarbamoyl)-phenylsulfon]-amide; TLC: ethyl acetate $R_f$=0.12

EXAMPLE 4/10

4-[N'-Methyl-N'-(3,5-bistrifluormethyl-benzoyl)-amino]-5-(4-chlorophenyl)-pentanoic acid N-[[4{N''-[2-(2-pyridyl)-ethyl]-carbamoyl}-phenylsulfon]]-amide; TLC: methylene chloride/methanol (9:1) $R_f$=0.4

EXAMPLE 4/11

4-[N'-Methyl-N'-(3,5-bistrifluormethyl-benzoyl)-amino]-5-(4-chlorophenyl)-pentanoic acid N-[4-(N''-benzyl-N''-methylcarbamoyl)-phenylsulfon]-amide; TLC: ethyl acetate $R_f$=0.26

EXAMPLE 4/12

4-[N'-Methyl-N'-(3,5-bistrifluormethyl-benzoyl)-amino]-5-(4-chlorophenyl)-pentanoic acid N-{4-[N''-(2-methoxybenzyl)-carbamoyl]-phenylsulfon}-amide; TLC: ethyl acetate $R_f$=0.43

EXAMPLE 39

4-[N'-Methyl-N'-(3,5-bistrifluormethyl-benzoyl)-amino]-5-(4-chlorophenyl)-2-methyl-pent-2-enoic acid N-[2-(2-pyridyl)-ethyl]-amide The title compound is prepared using exactly the same methodology as described in example 1/2, except that in step 1d) triethyl-2-phosphono-propionate is used instead of phosphonoacetic acid triethylester. The title compound is obtained as an amorphous white solid. TLC: ethyl acetate $R_f$=0.09.

EXAMPLE 39/1

4-[N'-Methyl-N'-(3,5-bistrifluormethyl-benzoyl)-amino]-5-(4-chlorophenyl)-2-methyl-pent-2-enoic acid N-(D,L-epsilon-caprolactam-3-yl)-amide; TLC: ethyl acetate $R_f$=0.16, is prepared analogously to example 39

EXAMPLE 39/2

4-[N'-Methyl-N'-(3,5bistrifluormethyl-benzoyl)-amino]-5-(4-chlorophenyl)-2-methyl-pent-2-enoic acid N-cyclohexyl-amide; TLC: hexane/ethyl acetate (1:1) $R_f$=0.34, is prepared analogously to example 39

EXAMPLE 40

4-[N'-Methyl-N'-(3,5-bistrifluormethyl-benzoyl)-amino]-5-(4-chlorophenyl)-2-methyl-pentanoic acid N-[2-(2-pyridyl)-ethyl]-amide The title compound is prepared using exactly the same methodology as described in examples 1 and 3,except that in step 1d) triethyl-2-phosphono-propionate is used instead of phosphonoacetic-acid-triethylester. The title compound is obtained as an amorphous white solid. TLC: ethyl acetate $R_f$=0.07

EXAMPLE 1

Continued

The Following Examples are Synthesized Analogously to Example 1

Instead of 3,5-bistrifluoromethyl-benzoyl chloride the corresponding benzoyl chloride or pyridinecarboxylic acid chloride respectively is used.

EXAMPLE 1/18

4-[N'-Methyl-N'-(3,5-dichloro-benzoyl)-amino]5-(4-chlorophenyl)-pent-2-enoic acid N-(2-methoxy-benzyl)-amide; white crystals, m.p. 189–191° C.

EXAMPLE 1/19

4-[N'-Methyl-N'-(3-methoxy-benzoyl)-amino]-5-(4-chlorophenyl)-pent-2-enoic acid N-(2-methoxy-benzyl)-amide; TLC: ethyl acetate $R_f$=0.39

EXAMPLE 1/20

4-[N'-Methyl-N'-(3,5-dimethyl-benzoyl)-amino]5-(4-chlorophenyl)-pent-2-enoic acid N-(2-methoxy-benzyl)-amide; white crystals, m.p. 180–182° C.

EXAMPLE 1/21

4-[N'-Methyl-N'-(2,4-dimethyl-benzoyl)-amino]5-(4-chlorophenyl)-pent-2-enoic acid N-(2-methoxy-benzyl)-amide; TLC: hexane/ethyl acetate (1:1) $R_f$=0.2

EXAMPLE 1/22

4-[N'-Methyl-N'-(3-nitro-benzoyl)-amino]-5-(4-chlorophenyl)-pent-2-enoic acid N-(2-methoxy-benzyl)-amide; white crystals, m.p. 166–168° C.

EXAMPLE 1/23

4-[N'-Methyl-N'-(2-pyridylcarbonyl)-amino]-5(4-chlorophenyl)-pent-2-enoic acid N-(2-methoxy-benzyl)-amide; TLC: ethyl acetate $R_f$=0.16

EXAMPLE 18

Continued

The Following Examples are Synthesized Analogously to Example 18

EXAMPLE 18/28

4-[N'-Methyl-N'-(3,5-bistrifluormethyl-benzoyl)-amino]-5-(1-methyl-indol-3-yl)-pentanoic acid N-(D-leucinol)-amide, $R_f$ (ethyl acetate)=0.17; starting amine used: D-leucinol [=(R)-2-amino-4-methyl-1-pentanol]

EXAMPLE 18/29
4-[N'-Methyl-N'-(3,5-bistrifluormethyl-benzoyl)-amino]-5-(1-methyl-indol-3-yl)-pentanoic acid N-(2-phenyl-ethyl)-amide, $R_f$ (ethyl acetate)=0.40

EXAMPLE 18/30
4-[N'-Methyl-N'-(3,5-bistrifluormethyl-benzoyl)-amino]-5-(1-methyl-indol-3-yl)-pentanoic acid N-[1,3,4,5-tetrahydrobenzo-azepin-2-on-3-yl]-amide, $R_f$ (ethyl acetate)=0.025

EXAMPLE 19
Continued

The Following Examples are Synthesized Analogously to Example 19

EXAMPLE 19/9
4-[N'-Methyl-N'-(3,5-bistrifluormethyl-benzoyl)-amino]-5-(1-methyl-indol-3-yl)-pent-2-enoic-acid N-benzyl-amide, $R_f$ (ethyl acetate/hexane 3:1)=0.46

EXAMPLE 19/10
4-[N'-Methyl-N'-(3,5-bistrifluormethyl-benzoyl)-amino]-5-(1-methyl-indol-3-yl)-pent-2-enoic acid N-(2-phenyl-ethyl)-amide, $R_f$ (ethyl acetate)=0.38

EXAMPLE 19/11
4-[N'-Methyl-N'-(3,5-bistrifluormethyl-benzoyl)-amino]-5-(1-methyl-indol-3-yl)-pent-2-enoic acid N-[1,3,4,5-tetrahydrobenzo-azepin-2-on-3-yl] amide, $R_f$ (ethyl acetate)=0.425

EXAMPLE 19/12
4-[N'-Methyl-N'-(3,5-bistrifluormethyl-benzoyl)-amino]-5-(1-methyl-indol-3-yl)-pent-2-enoic acid N-benzoylmethyl-amide, $R_f$ (ethyl acetate)=0.38; starting amine used: phenacylamine

EXAMPLE 19/13
4-[N'-Methyl-N'-(3,5-bistrifluormethyl-benzoyl)-amino]-5-(1methyl-indol-3-yl)-pent-2-enoic acid N-(D,L-epsilon-caprolactam-3-yl)-amide, $R_f$ (ethyl acetate)=0.29; starting amine used: D,L-3-amino-epsilon-caprolactam [=(R,S)-3-amino-hexahydro-azepin-2-one]

EXAMPLE 19/14
4-[N'-Methyl-N'-(3,5-bistrifluormethyl-benzoyl)-amino]-5-(1-methyl-indol-3-yl)-pent-2-enoic acid N-(1-naphthylmethyl)-amide, $R_f$ (ethyl acetate)=0.41

EXAMPLE 19/15
4-[N'-Methyl-N'-(3,5-bistrifluormethyl-benzoyl)-amino]-5-(1-methyl-indol-3-yl)-pent-2-enoic acid N-(2-methoxy-benzyl)-amide, $R_f$ (ethyl acetate)=0.47

EXAMPLE 19/16
4-[N'-Methyl-N'-(3,5-bistrifluormethyl-benzoyl)-amino]-5-(1-methyl-indol-3-yl)-pent-2-enoic acid N-cyclohexyl-amide, $R_f$ (ethyl acetate)=0.39

EXAMPLE 26
Continued

The Following Examples are Synthesized Analogously to Example 26

EXAMPLE 26/10
4-[N'-Methyl-N'-(3,5-bistrifluormethyl-benzoyl)-amino]-5-(1-H-indol-3-yl)-pentanoic-acid N-(D,L-epsilon-caprolactam-3-yl)-amide {=4-[N'-Methyl-N'-(3,5-bistrifluormethyl-benzoyl)-amino]-5-(1-H-indol-3-yl)-pentanoic-acid N-(hexahydro-azepin-2-on-3-yl)-amide}, $R_f$ (ethyl acetate)=0.19

EXAMPLE 26/11
4-[N'-Methyl-N'-(3,5-bistrifluormethyl-benzoyl)-amino]-5-(1-H-indol-3-yl)-pentanoic acid N-[1,3,4,5-tetrahydrobenzo-azepin-2-on-3-yl] amide, $R_f$ (ethyl acetate)=0.42

EXAMPLE 26/12
4-[N'-Methyl-N'-(3,5-bistrifluormethyl-benzoyl)-amino]-5-(1-H-indol-3-yl)-pentanoic-acid N-cyclohexyl-amide, $R_f$ (ethyl acetate)=0.44

EXAMPLE 26/13
4-[N'-Methyl-N'-(3,5-bistrifluormethyl-benzoyl)-amino]-5-(1-H-indol-3-yl)-pentanoic acid N-(D-leucinol)-amide, $R_f$ (ethyl acetate)=0.26

EXAMPLE 26/14
4-[N'-Methyl-N'-(3,5-bistrifluormethyl-benzoyl)-amino]-5-(1-H-indol-3-yl)-pentanoic-acid N-(3-N",N"-dimethylamino-propyl)-amide, $R_f$ (ethyl acetate)=0.025

EXAMPLE 26/15
4-[N'-Methyl-N'-(3,5-bistrifluormethyl-benzoyl)-amino]-5-(1-H-indol-3-yl)-pentanoic-acid N-(2-methoxy-benzyl)-amide, $R_f$ (ethyl acetate)=0.48

EXAMPLE 26/16
4-[N'-Methyl-N'-(3,5-bistrifluormethyl-benzoyl)-amino]-5-(1-H-indol-3-yl)-pentanoic-acid N-benzyl-amide, $R_f$ (ethyl acetate)=0.61

EXAMPLE 26/17
4-[N'-Methyl-N'-(3,5-bistrifluormethyl-benzoyl)-amino]-5-(1-H-indol-3-yl)-pentanoic acid N-(2-phenyl-ethyl)-amide, $R_f$ (ethyl acetate)=0.61

EXAMPLE 26/18
4-[N'-Methyl-N'-(3,5-bistrifluormethyl-benzoyl)-amino]-5-(1-H-indol-3-yl)-pentanoic acid N-[1-(1-naphthyl)-ethyl]-amide, $R_f$ (ethyl acetate)=0.595; starting amine used: 1-(1-aminoethyl)-naphthalin

EXAMPLE 26/19
4-[N'-Methyl-N'-(3,5-bistrifluormethyl-benzoyl)-amino]-5-(1-H-indol-3-yl)-pentanoic acid N,N-dimethyl-amide, $R_f$ (ethyl acetate)=0.30

EXAMPLE 27
Continued

The Following Examples are Synthesized Analogously to Example 27

EXAMPLE 27/10
4-[N'-Methyl-N'-(3,5-bistrifluormethyl-benzoyl)-amino]-5-(1-H-indol-3-yl)-pent-2-enoic acid N-(D,L-epsilon-caprolactam-3-yl)-amide, $R_f$ (methylene chloride/methanol 19:1)=0.29

EXAMPLE 27/11
4-[N'-Methyl-N'-(3,5-bistrifluormethyl-benzoyl)-amino]-5-(1-H-indol-3-yl)-pent-2-enoic acid N-[1,3,4,5-tetrahydrobenzo-azepin-2-on-3-yl] amide, $R_f$ (ethyl acetate)=0.33

EXAMPLE 27/12
4-[N'-Methyl-N'-(3,5-bistrifluormethyl-benzoyl)-amino]-5-(1-H-indol-3-yl)-pent-2-enoic-acid N-benzyl-amide, $R_f$ (ethyl acetate)=0.45

EXAMPLE 27/13
4-[N'-Methyl-N'-(3,5-bistrifluormethyl-benzoyl)-amino]-5-(1-H-indol-3-yl)-pent-2-enoic acid N-(2-phenyl-ethyl)-amide, $R_f$ (ethyl acetate)=0.52

EXAMPLE 27/14
4-[N'-Methyl-N'-(3,5-bistrifluormethyl-benzoyl)-amino]-5-(1-H-indol-3yl)-pent-2-enoic acid N-(2-methoxy-benzyl)-amide, $R_f$ (ethyl acetate)=0.51

EXAMPLE 27/15
4-[N'-Methyl-N'-(3,5-bistrifluormethyl-benzoyl)-amino]-5-(1-H-indol-3yl)-pent-2-enoic acid N-cyclohexyl-amide, $R_f$ (ethyl acetate)=0.42

EXAMPLE 27/16
4-[N'-Methyl-N'-(3,5-bistrifluormethyl-benzoyl)-amino]-5-(1-H-indol-3-yl)-pent-2-enoic acid (4-acetylamino-4-phenyl-piperidineamide), $R_f$ (methylene chloride/methanol 5:1)=0.725

EXAMPLE 27/17
4-[N'-Methyl-N'-(3,5-bistrifluormethyl-benzoyl)-amino]-5-(1-H-indol-3-yl)-pent-2-enoic acid N-(3-N",N"-dimethylamino-propyl)-amide, $R_f$ (ethyl acetate)=0.015

EXAMPLE 27/18
4-[N'-Methyl-N'-(3,5-bistrifluormethyl-benzoyl)-amino]-5-(1-H-indol-3-yl)-pent-2-enoic acid N-(D-leucinol)-amide, $R_f$ (ethyl acetate)=0.125 and 0.20 (diastereomer)

EXAMPLE 27/19
4-[N'-Methyl-N'-(3,5-bistrifluormethyl-benzoyl)-amino]-5-(1-H-indol-3-yl)-pent-2-enoic acid N-(L-leucinol)-amide, $R_f$ (ethyl acetate)=0.14 and 0.24 (diastereomer)

EXAMPLE 27/20
4-[N'-Methyl-N'-(3,5-bistrifluormethyl-benzoyl)-amino]-5-(1-H-indol-3-yl)-pent-2-enoic acid N-ethyl-amide, $R_f$ (ethyl acetate)=0.29

EXAMPLE 27/21
4-[N'-Methyl-N'-(3,5-bistrifluormethyl-benzoyl)-amino]-5-(1-H-indol-3-yl)-pent-2-enoic acid N-butyl-amide, $R_f$ (ethyl acetate)=0.35

EXAMPLE 27/22
4-[N'-Methyl-N'-(3,5-bistrifluormethyl-benzoyl)-amino]-5-(1-H-indol-3-yl)-pent-2-enoic acid N,N-diethyl-amide, $R_f$ (ethyl acetate)=0.27

EXAMPLE 27/23
4-[N'-Methyl-N'-(3,5-bistrifluormethyl-benzoyl)-amino]-5-(1-H-indol-3-yl)-pent-2-enoic acid (4-dimethylamino-piperidineamide), $R_f$ (ethyl acetate)=0.015

EXAMPLE 27/24
4-[N'-Methyl-N'-(3,5-bistrifluormethyl-benzoyl)-amino]-5-(1-H-indol-3-yl)-pent-2-enoic acid N-[1-(1-naphthyl)-ethyl]-amide, $R_f$ (ethyl acetate)=0.49 and 0.56 (diastereomers)

EXAMPLE 20
Continued
The Following Examples are Synthesized Analogously to Example 20

EXAMPLE 20/10
4-[N'-Methyl-N'-(3,5-bistrifluormethyl-benzoyl)-amino]-5-(naphth-2-yl)-pentanoic acid N-[1,3,4,5-tetrahydrobenzoazepin-2-on-3-yl] amide, $R_f$ (methylene chloride/methanol 15:1)=0.20

EXAMPLE 20/11
4-[N'-Methyl-N'-(3,5-bistrifluormethyl-benzoyl)-amino]-5-(naphth-2-yl)-pentanoic-acid N-(D,L-epsilon-caprolactam-3-yl-)-amide, $R_f$ (methylene chloride/methanol 19:1)=0.20

EXAMPLE 20/12
4-[N'-Methyl-N'-(3,5-bistrifluormethyl-benzoyl)-amino]-5-(naphth-2-yl)-pentanoic-acid N-cyanomethyl-amide, $R_f$ (methylene chloride/methanol 15:1)=0.53

EXAMPLE 20/13
4-[N'-Methyl-N'-(3,5-bistrifluormethyl-benzoyl)-amino]-5-(naphth-2-yl)-pentanoic-acid [4-(2-methoxy-phenyl)-piperazineamide], $R_f$ (ethyl acetate/hexane 4:1)=0.43

EXAMPLE 20/14
4-[N'-Methyl-N'-(3,5-bistrifluormethyl-benzoyl)-amino]-5-(naphth-2-yl)-pentanoic-acid N-(2-methoxy-benzyl)-amide, $R_f$ (ethyl acetate/hexane 1:1)=0.16

EXAMPLE 20/15
4-[N'-Methyl-N'-(3,5-bistrifluormethyl-benzoyl)-amino]-5-(naphth-2-yl)-pentanoic-acid (4-phenylsulfinylmethyl-4-methoxy-piperidineamide), $R_f$ (methylene chloride/methanol 15:1)=0.68

EXAMPLE 20/16
4-[N'-Methyl-N'-(3,5-bistrifluormethyl-benzoyl)-amino]-5-(naphth-2-yl)-pentanoic-acid N-(1-benzyl-4-methoxycarbonyl-piperidin-4-yl)-amide, $R_f$ (methylene chloride/methanol 15:1)=0.08

EXAMPLE 20/17
4-[N'-Methyl-N'-(3,5-bistrifluormethyl-benzoyl)-amino]-5-(naphth-2-yl)-pentanoic-acid N-[2-(N"-methylcarbamoyl)-propyl]-amide, $R_f$ (methylene chloride/methanol 15:1)=0.14; starting amine used: 3-amino-2,N-dimethyl-propionamide

EXAMPLE 20/18
4-[N'-Methyl-N'-(3,5bistrifluormethyl-benzoyl)-amino]-5-(naphth-2-yl)-pentanoic-acid N-(1,1-dimethyl-1-carbamoyl-methyl) amide, $R_f$ (ethyl acetate)=0.15; starting amine used: 2-amino-2-methyl-propionamide

EXAMPLE 20/19
4-[N'-Methyl-N'-(3,5-bistrifluormethyl-benzoyl)-amino]-5-(naphth-2-yl)-pentanoic-acid N-cyclohexyl-amide, $R_f$ (methylene chloride/methanol 19:1)=0.44

EXAMPLE 20/20
4-[N'-Methyl-N'-(3,5-bistrifluormethyl-benzoyl)-amino]-5-(naphth-2-yl)-pentanoic-acid N-cyclopentyl-amide, $R_f$ (methylene chloride/methanol 19:1)=0.44

EXAMPLE 20/21
4-[N'-Methyl-N'-(3,5-bistrifluormethyl-benzoyl)-amino]-5-(naphth-2-yl)-pentanoic-acid N-cyclopropyl-amide, $R_f$ (methylene chloride/methanol 19:1)=0.33

EXAMPLE 20/22
4-[N'-Methyl-N'-(3,5-bistrifluormethyl-benzoyl)-amino]-5-(naphth-2-yl)-pentanoic-acid N-(2-methyl-phenylsulfon)-amide, $R_f$ (methylene chloride/methanol 15:1)=0.42

EXAMPLE 21

Continued

The Following Examples are Synthesized Analogously to Example 21

EXAMPLE 21/10
4-[N'-Methyl-N'-(3,5-bistrifluormethyl-benzoyl)-amino]-5-(naphth-2-yl)-pent-2-enoic acid N-[1,3,4,5-tetrahydrobenzo-azepin-2-on-3-yl]-amide, $R_f$ (ethyl acetate/hexane 4:1)=0.18

EXAMPLE 21/11
4-[N'-Methyl-N'-(3,5-bistrifluormethyl-benzoyl)-amino]-5-(naphth-2-yl)-pent-2-enoic-acid N-(D,L-epsilon-caprolactam-3-yl)-amide, $R_f$ (ethyl acetate/hexane 4:1)=0.12

EXAMPLE 21/12
4-[N'-Methyl-N'-(3,5-bistrifluormethyl-benzoyl)-amino]-5-(naphth-2-yl)-pent-2-enoic-acid N-cyclohexyl-amide, $R_f$ (ethyl acetate/hexane 1:1)=0.30

EXAMPLE 21/13
4-[N'-Methyl-N'-(3,5-bistrifluormethyl-benzoyl)-amino]-5-(naphth-2-yl)-pent-2-enoic-acid N-cycloheptyl-amide, $R_f$ (ethyl acetate/hexane 1:1)=0.23

EXAMPLE 21/14
4-[N'-Methyl-N'-(3,5-bistrifluormethyl-benzoyl)-amino]-5-(naphth-2-yl)-pent-2-enoic-acid N-cyclopentyl-amide, $R_f$ (methylene chloride/methanol 19:1)=0.125

EXAMPLE 21/15
4-[N'-Methyl-N'-(3,5-bistrifluormethyl-benzoyl)-amino]-5-(naphth-2-yl)-pent-2-enoic-acid N-cyclobutyl-amide, $R_f$ (ethyl acetate/hexane 1:1) 0.40

EXAMPLE 21/16
4-[N'-Methyl-N'-(3,5-bistrifluormethyl-benzoyl)-amino]-5-(naphth-2-yl)-pent-2-enoic-acid N-cyclopropyl-amide, $R_f$ (methylene chloride/methanol 19:1)=0.195

EXAMPLE 21/17
4-[N'-Methyl-N'-(3,5-bistrifluormethyl-benzoyl)-amino]-5-(naphth-2-yl)-pent-2-enoic-acid N-(chromon-3-ylmethyl)-amide, $R_f$ (methylene chloride/methanol 15:1)=0.27; starting amine used: 3-aminomethyl-1-benzopyran-4-one

EXAMPLE 21/18
4-[N'-Methyl-N'-(3,5-bistrifluormethyl-benzoyl)-amino]-5-(naphth-2-yl)-pent-2-enoic-acid [4-(2-pyrimidyl)-piperazineamide], $R_f$ (methylene chloride/methanol 19:1)=0.44.

EXAMPLE 41
4-[N'-Methyl-N'-(3,5-bistrifluormethyl-benzoyl)-amino]-5-(1-methyl-indol-3-yl)-2-methyl-pent-2-enoic acid-N-(D,L-epsilon-caprolactam-3-yl)-amide, $R_f$ (ethylacetate)=0.31

The title compound is prepared using exactly the same methodology as described in example 19, except that in step (f) of example 18 triethyl-2-phosphono-propionate is used instead of phosphonoacetic acid triethylester.

EXAMPLE 42
4-[N'-Methyl-N'-(3,5-bistrifluormethyl-benzoyl)-amino]-5-(1-methyl-indol-3-yl)-2-methyl-pent-2-enoic acid-N-cyclohexyl-amide, $R_f$ (ethylacetate)=0.45

The title compound is prepared using exactly the same methodology as described in example 19, except that in step (f) of example 18 triethyl-2-phosphono-propionate is used instead of phosphonoacetic acid triethylester.

EXAMPLE 43
4-[N'-Methyl-N'-(3,5-bistrifluormethyl-benzoyl)-amino]-5-(1-H-indol-3-yl)-2-methyl-pent-2-enoic acid-N-(D,L-epsilon-caprolactam-3-yl)-amide, $R_f$ (methylene chloride/methanol 19:1)=0.33

The title compound is prepared using exactly the same methodology as described in example 27, except that in step (f) of example 26 triethyl-2-phosphono-propionate is used instead of phosphonoacetic acid triethylester.

EXAMPLE 44
4-[N'-Methyl-N'-(3,5-bistrifluormethyl-benzoyl)-amino]-5 (1-H-indol-3-yl)-2-methyl-pent-2-enoic acid-N-cyclohexyl-amide, $R_f$ (ethylacetate)=0.46

The title compound is prepared using exactly the same methodology as described in example 27, except that in step (f) of example 26 triethyl-2-phosphono-propionate is used instead of phosphonoacetic acid triethylester.

EXAMPLE 45
4-[N'-Methyl-N'-(3,5-bistrifluormethyl-benzoyl)-amino]-5-(naphth-2-yl)-2-methyl-pent-2-enoic acid-N-(D,L-epsilon-caprolactam-3yl)-amide, $R_f$ (ethyl acetate/hexane 4:1)=0.15

The title compound is prepared using exactly the same methodology as described in example 21, except that in step (f) of example 20 triethyl-2-phosphono-propionate is used instead of phosphonoacetic acid triethylester.

EXAMPLE 46
4-[N'-Methyl-N'-(3,5-bistrifluormethyl-benzoyl)-amino]-5-(naphth-2-yl)-2-methyl-pent-2-enoic acid-N-cyclohexyl-amide, $R_f$ (ethylacetate/hexane 1:1)=0.36

The title compound is prepared using exactly the same methodology as described in example 21, except that in step (f) of example 20 triethyl-2-phosphono-propionate is used instead of phosphonoacetic acid triethylester.

Examples A to E

Pharmaceutical Compositions

Example A

Tablets, each comprising 50 mg of active ingredient:

| Composition (10000 tablets) | |
| --- | --- |
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 9 of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 145.0 mg and comprising 50.0 mg of active ingredient; if desired the tablets may be provided with dividing notches for finer adaptation of the dose.

Example B

Film-coated tablets, each comprising 100 mg of active ingredient:

| Composition (1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed together and the mixture is moistened with a paste prepared from 15 g of corn starch and water (with heating), and granulated. The granules are dried and the remainder of the corn starch, the talc and the calcium stearate are mixed with the granules. The mixture is compressed to form tablets (weight: each 280 mg) which are then film-coated with a solution of the hydroxypropylmethylcellulose and the shellac in dichloromethane (final weight of each film-coated tablet: 283 mg).

Example C

Hard gelatin capsules, each comprising 100 mg of active ingredient:

| Composition (1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. All four components are then intimately mixed for 10 minutes. Finally, the magnesium stearate is added through a sieve of 0.8 mm mesh size. After further mixing (3 minutes), 390 mg portions of the resulting formulation are introduced into size 0 hard gelatin capsules.

Example D

An injection or infusion solution, comprising 5 mg of active ingredient per 2.5 ml ampoule.

| Composition (1000 ampoules) | |
|---|---|
| active ingredient | 5.0 g |
| sodium chloride | 22.5 g |
| phosphate buffer solution (pH: 7.4) | 300.0 g |
| demineralised water | ad 2500.0 ml |

The active ingredient and the sodium chloride are dissolved in 1000 ml of demineralised water and the solution is filtered through a microfilter. The phosphate buffer solution is added to the filtrate and the mixture is made up to 2500 ml with demineralised water. For the preparation of unit dose forms, 2.5 ml portions of the mixture are introduced into glass ampoules which then each comprise 5 mg of active ingredient.

Example E

An inhalation suspension, comprising propellant and forming a solid aerosol, that comprises 0.1% by weight active ingredient:

| Composition | % by weight |
|---|---|
| active ingredient, micronised | 0.1 |
| sorbitan trioleate | 0.5 |
| propellant A (trichlorotrifluoroethane) | 4.4 |
| propellant B (dichlorodifluoromethane and 1,2-dichlorotetrafluoroethane) | 15.0 80.0 |

With the exclusion of moisture, the active ingredient is suspended in trichlorotrifluoroethane, with the addition of the sorbitan trioleate, using a conventional homogeniser and the suspension in introduced into an aerosol container equipped with a metering valve. The container is closed and filled up with propellant B under pressure.

What is claimed is:

1. A compound of formula I

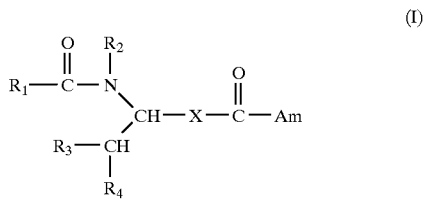

wherein $R_1$ is aryl or heteroaryl;

$R_2$ is hydrogen, lower alkyl or aryl-lower alkyl;

$R_3$ is hydrogen, lower alkyl, aryl or heteroaryl;

$R_4$ is aryl or heteroaryl;

X is straight chain $C_1$–$C_7$alkylene, $C_2$–$C_7$alkenylene or $C_4$–$C_7$alkanedienylene; and Am is NH caprolactam, or a salt thereof.

2. 4-[N'-Methyl-N'-(3,5-bistrifluoromethyl-benzoyl)-amino]-5-(4-chlorophenyl)-pent-2-enoic acid N-[2-(2-pyridyl)-ethyl]-amide according to claim 1 or a pharmaceutically acceptable salt thereof.

3. 4-[N'-Methyl-N'-(3,5-bistrifluormethyl-benzoyl)-amino]-5-(4-chlorophenyl)-pent-2-enoic acid N-(D,L-epsilon-caprolactam-3-yl)-amide according to claim 1 or a pharmaceutically acceptable salt thereof.

4. A compound of formula I according to claim 1, wherein $R_1$ is phenyl or pyridyl, each of which is unsubstituted or substituted by 1 or 2 substituents selected from the group consisting of lower alkyl, trifluoromethyl, halogen, hydroxy, lower alkoxy and nitro;

$R_2$ is hydrogen, lower alkyl or phenyl-lower alkyl wherein the phenyl group is unsubstituted or substituted by 1 or 2 substituents selected from the group consisting of lower alkyl, trifluoromethyl, halogen, hydroxy and lower alkoxy;

$R_3$ is hydrogen, lower alkyl, phenyl, naphthyl or indolyl, with phenyl, naphthyl and indolyl each being unsubstituted or substituted by 1 or 2 substituents selected from the group consisting of lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group consisting of lower alkyl, trifluoromethyl, halogen, hydroxy and lower alkoxy, or a salt thereof.

5. A compound of formula I according to claim 1, wherein $R_1$ is phenyl that is unsubstituted or substituted by 1 or 2 substituents selected from the group consisting of lower alkyl, trifluoromethyl, halogen, hydroxy and lower alkoxy;

$R_2$ is hydrogen, lower alkyl or phenyl-lower alkyl wherein the phenyl group is unsubstituted or substituted by 1 or 2 substituents selected from the group consisting of lower alkyl, trifluoromethyl, halogen, hydroxy and lower alkoxy;

$R_3$ is hydrogen, lower alkyl, phenyl, naphthyl or indolyl, with phenyl, naphthyl and indolyl each being unsubstituted or substituted by 1 or 2 substituents selected from the group consisting of lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group consisting of lower alkyl, trifluoromethyl, halogen, hydroxy and lower alkoxy;

X is straight chain $C_1$–$C_7$alkylene or $C_2$–$C_7$alkenylene,
or a salt thereof.

6. A compound of formula I according to claim 1, wherein $R_1$ is phenyl that is unsubstituted or substituted by 1 or 2 substituents selected from the group consisting of lower alkyl, trifluoromethyl, halogen, hydroxy, lower alkoxy and nitro, or $R_1$ is pyridyl;

$R_2$ is hydrogen or lower alkyl;

$R_3$ is hydrogen, lower alkyl, phenyl or naphthyl, with phenyl and, naphthyl each being unsubstituted or substituted by 1 or 2 substituents selected from the group consisting of lower alkyl, trifluoromethyl, halogen, hydroxy and lower alkoxy;

$R_4$ is phenyl, naphthyl or indolyl, each of those radicals being unsubstituted or substituted by 1 or 2 substituents selected from the group consisting of lower alkyl, trifluoromethyl, halogen, hydroxy and lower alkoxy;

X is straight chain $C_1$–$C_4$alkylene or $C_2$–$C_4$alkenylene,
or a pharmaceutically acceptable salt thereof.

7. A compound of formula I according to claim 1, wherein $R_1$ is 3,5-bistrifluoromethylphenyl;

$R_2$ is methyl;

the group —$CHR_3R_4$ is benzyl, 4-chlorobenzyl, 2-naphthylmethyl, diphenylmethyl, 1H-indol-3-ylmethyl;

X is 1,2-ethylene, or 1,2-ethenylene,
or a pharmaceutically acceptable salt thereof.

8. A pharmaceutical composition comprising a compound according to claim 1 and at least one pharmaceutically acceptable carrier.

9. A method for the treatment of diseases of the animal or human body that are responsive to antagonization of the NK1-receptor comprising administering to an animal or human having any one of such diseases a compound according to claim 1.

10. A process for the preparation of a compound of formula I according to claim 1, which process comprises (A) N-acylating a compound of formula II

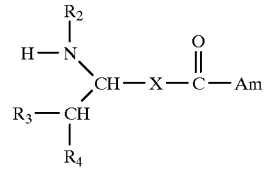

(II)

with a carboxylic acid, $R_1$—C(=O)—OH, or with a reactive derivative thereof, or (B) condensing a carboxylic acid of formula III

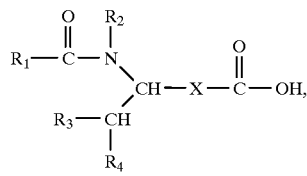

(III)

or a reactive derivative thereof, with ammonia or with a mono- or disubstituted amine, or (C) for the preparation of a compound of formula I wherein X is $C_{2-7}$alkylene or $C_{4-7}$alkanedienylene, as a last step, forming the double bond or one of the double bonds by means of a Wittig reaction or Wittig-Hozner reaction, and optionally, converting a resulting salt into the free compound or a different salt, and further, optionally, converting a resulting free compound of formula I having salt-forming properties into a salt and further, optionally, separating a resulting mixture of stereoisomers, diastereoisomers or enantiomers into the individual stereoisomers, diastereoisomers or enantiomers.

* * * * *